(12) United States Patent
Pier et al.

(10) Patent No.: US 7,723,087 B2
(45) Date of Patent: May 25, 2010

(54) NUCLEIC ACID MOLECULES FOR ENHANCED PRODUCTION OF A BACTERIAL POLYSACCHARIDE AND METHODS OF USE THEREOF

(75) Inventors: Gerald B. Pier, Brookline, MA (US); Kimberly Jefferson, Dedham, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 542 days.

(21) Appl. No.: 10/712,391

(22) Filed: Nov. 12, 2003

(65) Prior Publication Data

US 2004/0175731 A1  Sep. 9, 2004

Related U.S. Application Data

(60) Provisional application No. 60/425,569, filed on Nov. 12, 2002.

(51) Int. Cl.
*C12N 9/00* (2006.01)
*C12N 1/20* (2006.01)
*C12N 15/00* (2006.01)
*C07H 21/02* (2006.01)
*C07H 21/04* (2006.01)

(52) U.S. Cl. ............... 435/183; 435/252.3; 435/320.1; 536/23.1; 536/23.2

(58) Field of Classification Search ............... 435/183, 435/252.3, 320.1; 536/23.1, 23.2
See application file for complete search history.

(56) References Cited

U.S. PATENT DOCUMENTS

| | | | |
|---|---|---|---|
| 4,197,290 A | 4/1980 | Yoshida | |
| 4,285,936 A | 8/1981 | Pier et al. | |
| 4,443,549 A | 4/1984 | Sadowski | |
| 4,464,799 A | 8/1984 | Nava | |
| 4,578,458 A | 3/1986 | Pier | |
| 4,652,448 A | 3/1987 | Sadowski | |
| 4,786,592 A | 11/1988 | Deal et al. | |
| 4,789,735 A | 12/1988 | Frank et al. | |
| 4,795,803 A | 1/1989 | Lindberg et al. | |
| 4,830,852 A | 5/1989 | Marburg et al. | |
| 4,859,449 A | 8/1989 | Mattes | |
| 4,879,272 A | 11/1989 | Shimoda et al. | |
| 4,902,616 A | 2/1990 | Fournier et al. | |
| 5,055,455 A | 10/1991 | Pier | |
| 5,362,754 A | 11/1994 | Raad et al. | |
| 5,366,505 A | 11/1994 | Farber | |
| 5,571,511 A | 11/1996 | Fischer | |
| 5,589,591 A | 12/1996 | Lewis | |
| 5,688,516 A | 11/1997 | Raad et al. | |
| 5,718,694 A | 2/1998 | Rupp | |
| 5,830,539 A | 11/1998 | Yan et al. | |
| 5,858,350 A | 1/1999 | Vournakis et al. | |
| 5,866,140 A | 2/1999 | Fattom et al. | |
| 5,980,910 A | 11/1999 | Pier | |
| 5,989,542 A | 11/1999 | Pier et al. | |
| 6,245,735 B1 | 6/2001 | Pier | |
| 6,399,066 B1 | 6/2002 | Pier | |
| 6,743,431 B2 | 6/2004 | Pier | |
| 7,157,443 B2 | 1/2007 | Joyce et al. | |
| 7,252,828 B2 | 8/2007 | Pier et al. | |
| 2002/0119166 A1 | 8/2002 | Pier et al. | |
| 2003/0124631 A1 | 7/2003 | Pier et al. | |
| 2004/0091494 A1 | 5/2004 | Pier et al. | |
| 2004/0175731 A1 | 9/2004 | Pier et al. | |
| 2005/0025775 A1 | 2/2005 | Pier et al. | |
| 2005/0118198 A1 | 6/2005 | Pier et al. | |
| 2006/0115486 A1 | 6/2006 | Pier et al. | |

FOREIGN PATENT DOCUMENTS

| | | |
|---|---|---|
| EP | 0 302 781 A1 | 2/1989 |
| EP | 0 694 309 A2 | 10/1996 |
| EP | 03783450.4 | 2/2006 |
| FR | 2 410 043 A1 | 6/1979 |
| FR | 2 581 877 A1 | 11/1986 |
| FR | 2 640 628 A1 | 12/1988 |
| GB | 2 009 771 A | 6/1979 |
| WO | WO 85/05037 A1 | 11/1985 |
| WO | WO 86/02358 A1 | 4/1986 |
| WO | WO 88/02028 A1 | 3/1988 |
| WO | WO 89/04873 A1 | 6/1989 |
| WO | WO 90/03398 A1 | 4/1990 |
| WO | WO 90/06696 A2 | 6/1990 |
| WO | WO 93/01276 A1 | 1/1993 |
| WO | WO 93/09811 A1 | 5/1993 |
| WO | WO 93/19373 A1 | 9/1993 |

(Continued)

OTHER PUBLICATIONS

Pier et al. Accession AAZ87998. May 31, 2000.*

(Continued)

*Primary Examiner*—Christian L Fronda
(74) *Attorney, Agent, or Firm*—Wolf, Greenfield & Sacks, P.C.

(57) ABSTRACT

The invention relates to nucleic acid sequences and related compositions for producing over-expression of the polysaccharide PNAG of *Staphylococci*. PNAG may be isolated and formulated into vaccines or used to generate antibodies. Binding agents of the nucleic acids are also described. The invention also relates to diagnostic and therapeutic methods using the compositions.

17 Claims, 8 Drawing Sheets

FOREIGN PATENT DOCUMENTS

| | | |
|---|---|---|
| WO | WO 94/15640 A1 | 7/1994 |
| WO | WO 98/52605 A1 | 11/1998 |
| WO | WO 99/40440 A1 | 8/1999 |
| WO | WO 00/03745 * | 1/2000 |
| WO | WO 00/03745 A2 | 1/2000 |
| WO | WO 00/35504 A1 | 6/2000 |
| WO | WO 03/053462 A2 | 7/2003 |
| WO | WO 03/085093 A2 | 10/2003 |
| WO | WO 2004/043405 A2 | 5/2004 |
| WO | WO 2004/043407 A2 | 5/2004 |
| WO | WO 2005/103084 | 11/2005 |

OTHER PUBLICATIONS

Cramton et al. Accession AF086783. Oct. 1, 1999.*
Maira-Litran et al., Immunochemical properties of the staphylococcal poly-N-acetylglucosamine surface polysaccharide. Infect Immun. Aug. 2002;70(8):4433-40.
McKenney et al., The ica locus of *Staphylococcus epidermidis* encodes production of the capsular polysaccharide/adhesin. Infect Immun. Oct. 1998;66(10):4711-20.
Mack et al., The intercellular adhesin involved in biofilm accumulation of *Staphylococcus epidermidis* is a linear beta-1,6-linked glucosaminoglycan: purification and structural analysis. J Bacteriol. Jan. 1996;178(1):175-83.
Baldassarri et al., Purification and characterization of the staphylococcal slime-associated antigen and its occurrence among *Staphylococcus epidermis* clinical isolates. Infect Immun. Aug. 1996;64(8):3410-5.
Genbank Submission; NIH/NCBI, Accession No. BA000018; Kuroda et al.; Oct. 22, 2004 (last submission).
[No Author Listed] ATCC Catalogue website 2001; ATCC No. 35984.
[No Author Listed] ATCC Catalogue: Bacteria and Bacteriophages; 1992; 18th Edition; p. 301.
Ammendolia et al., Slime production and expression of the slime-associated antigen by staphylococcal clinical isolates. J Clin Microbiol. Oct. 1999;37(10):3235-8.
Barsham et al., Detection of antibodies of *Staphylococcus epidermidis* in infected total hip replacements by an enzyme linked immunosorbent assay. J Clin Pathol. Jul. 1985;38(7):839-40.
Bernstein, et al., Antibody coated bacteria in otitis media with effusions. Ann Otol Rhinol Laryngol Suppl. May-Jun. 1980;89(3 Pt 2):104-9. Abstract only.
Capek et al., Chapters 22: Carbohydrates and Chapter 23: Polysaccharides. in Journal of Chromatography Journal Library—vol. 3: Liquid Column Chromatography, A Survey of Modern Techniques and Applications. Deyl et al., eds. Elsevier Scientific Publishing Company: New York, 1975. p. 465-528.
Chanter, Partial purification and characterization of two non K99 mannose-resistant haemagglutinins of *Escherichia coli* B41. J Gen Microbiol. Jan. 1983;129(1):235-43.
Chen et al., Characterization and biological properties of chemically deglycosylated human chorionic gonadotropin. Role of carbohydrate moieties in adenylate cyclase activation. J Biol Chem. Dec. 10, 1982;257(23):14446-52.
Christensen et al., Adherence of slime-producing strains of *Staphylococcus epidermidis* to smooth surfaces. Infect Immun. Jul. 1982;37(1):318-26.
Chu et al., Preparation, characterization, and immunogenicity of conjugates composed of the O-specific polysaccharide of *Shigella dysenteriae* type 1 (Shiga's bacillus) bound to tetanus toxoid. Infect Immun. Dec. 1991;59(12):4450-8.
Conlon et al., icaR encodes a transcriptional repressor involved in environmental regulation of ica operon expression and biofilm formation in *Staphylococcus epidermidis*. J Bacteriol. Aug. 2002;184;(16):4400-8.
Conlon et al., Regulation of icaR gene expression in *Staphylococcus epidermidis*. FEMS Microbiol Lett. Nov. 2002;216(2):171-7.
Cramton et al., The intercellular adhesion (ica) locus is present in *Staphylococcus aureus* and is required for biofilm formation. Infect Immun. Oct. 1999;67(10):5427-33.
Dobrin, et al., The role of complement, immunoglobulin and bacterial antigen in coagulase-negative staphylococcal shunt nephritis. Am J Med. Nov. 1975;59(5):660-73. Abstract only.
Elder et al., Characterization of monoclonal antibodies specific for adhesion: isolation of an adhesin of *Streptococcus sanguis* FW213. Infect Immun. Nov. 1986;54(2):421-7.
Espersen, et al., Solid-phase radioimmunoassay for IgG antibodies to *Staphylococcus epidermidis*. Use in serious coagulase-negative staphylococcal infections. Arch Intern Med. Apr. 1987;147(4):689-93. Abstract only.
Espersen, et al., Enzyme-linked immunosorbent assay for detection of *Staphylococcus epidermidis* antibody in experimental *S. epidermidis* endocarditis. J Clin Microbiol. Feb. 1986;23(2):339-42.
Fattom et al., Synthesis and immunologic properties in mice of vaccines composed of *Staphylococcus aureus* type 5 and type 8 capsular polysaccharides conjugated to *Pseudomonas aeruginosa* exotoxin A. Infect Immun. Jul. 1990;58(7):2367-74.
Fattom et al., Effect of conjugation methodology, carrier protein, and adjuvants on the immune response to *Staphylococcus aureus* capsular polysaccharides. Vaccine. Oct. 1995;13(14):1288-93.
Ferreiros et al., Purification and partial characterization of a K99-antigen associated adhesin in *Escherichia coli* (637 strain). Rev Esp Fisiol. Mar. 1983;39(1):45-50.
Fournier et al., Purification and characterization of *Staphylococcus aureus* type 8 capsular polysaccharide. Infect Immun. Jul. 1984;45(1):87-93.
Gerke et al., Characterization of the N-acetylglucosaminyltransferase activity involved in the biosynthesis of the *Staphylococcus epidermidis* polysaccharide intercellular adhesin. J Biol Chem. Jul. 17, 1998;273(29):18586-93.
Gray et al., Effect of extracellular slime substance from *Staphylococcus epidermidis* on the human cellular immune response. Lancet. Feb. 18, 1984;1(8373):365-7.
Heilmann et al., Molecular basis of intercellular adhesion in the biofilm-forming *Staphylococcus epidermidis*. Mol Microbiol. Jun. 1996;20(5):1083-91.
Heilmann et al., Characterization of Tn917 insertion mutants of *Staphylococcus epidermidis* affected in biofilm formation. Infect Immun. Jan. 1996;64(1):277-82.
Hogt et al., Cell surface characteristics of coagulase-negative *Staphylococci* and their adherence to fluorinated poly(ethylenepropylene). Infect Immun. Jan. 1986;51(1):294-301.
Ichiman et al., The relationship of capsular-type of *Staphylococcus epidermidis* to virulence and induction of resistance in the mouse. J Appl Bacteriol. Oct. 1981;51(2):229-41.
Ichiman et al., Induction of resistance with heat-killed unencapsulated strains of *Staphylococcus epidermidis* against challenge with encapsulated strains of *Staphylococcus epidermidis*. Microbiol Immunol. 1989;33(4):277-86.
Ichiman et al., Relation of human serum antibody against *Staphylococcus epidermidis* cell surface polysaccharide detected by enzyme-linked immunosorbent assay to passive protection in the mouse. J Appl Bacteriol. Aug. 1991;7(2):176-81.
Ichiman et al., Specificity of monclonal antibodies against an encapsulated strain of *Staphylococcus epidermids*. in The *Staphylococci*, Zbl Bakt. 1991;Suppl 21:150-2.
Jefferson et al., Identification of a 5-nucleotide sequence that controls expression of the ica locus in *Staphylococcus aureus* and characterization of the DNA-binding properties of IcaR. Mol Microbiol. May 2003;48(4):889-99.
Jefferson et al., The teicoplanin-associated locus regulator (TcaR) and the intercellular adhesin locus regulator (IcaR) are transcriptional inhibitors of the ica locus in *Staphylococcus aureus*. J Bacteriol. Apr. 2004;186(8):2449-56.
Johnson et al., Interference with granulocyte function by *Staphylococcus epidermidis* slime. Infect Immun. Oct. 1986;54(1):13-20.
Kelly-Quintos et al., Biological Characterization of Fully Human Monoclonal Antibodies to Staphylococcal Surface Polysaccharide PNAG. Abstracts of the 104th General Meeting of the American Society for Microbiology. Am Soc Microbiol. May 2004;abstract A-63. Abstract and corresponding presentation.

Keutmann et al., Evidence for a conformational change in deglycosylated glycoprotein hormones. FEBS Lett. Jun. 1985;185(2):333-8.

Kohler, Derivation and diversification of monoclonal antibodies. Science. Sep. 19, 1986;233(4770):1281-6.

Kojima et al., Antibody to the capsular polysaccharide/adhesin protects rabbits against catheter-related bacteremia due to coagulase-negative Staphylococci. J Infect Dis. Aug. 1990;162(2):435-41.

Kuroda et al., Whole genome sequencing of meticillin-resistant Staphylococcus aureus. Lancet. Apr. 21, 2001;357(9264):1225-40.

Lee et al., Chemical characterization and immunogenicity of capsular polysaccharide isolated from mucoid Staphylococcus aureus. Infect Immun. Sep. 1987;55(9):2191-7.

Lee et al., Protective efficacy of antibodies to the Staphylococcus aureus type 5 capsular polysaccharide in a modified model of endocarditis in rats. Infect Immun. Oct. 1997;65(10):4146-51.

Leith et al., Purification of a Mycoplasma pneumoniae adhesin by monoclonal antibody affinity chromatography. J Bacteriol. Feb. 1984;157(2):678-80.

Locksley, Chapter 94: Staphylococcal Infections. in Harrison's Principles of Internal Medicine, Eleventh Edition. Braunwald et al., eds. McGraw-Hill Book Company, Inc.: New York, 1950. p. 537-43.

Ludwicka et al., Investigation on extracellular slime substance produced by Staphylococcus epidermidis. Zentralbl Bakteriol Mikrobiol Hyg [A]. Dec. 1984;258(2-3):256-67.

Mack et al., Association of biofilm production of coagulase-negative Staphylococci with expression of a specific polysaccharide intercellular adhesin. J Infect Dis. Oct. 1996;174(4):881-4.

Mack et al., Characterization of transposon mutants of biofilm-producing Staphylococcus epidermidis impaired in the accumulative phase of biofilm production: genetic identification of a hexosamine-containing polysaccharide intercellular adhesin. Infect Immun. Aug. 1994;62(8):3244-53.

Mack et al., Parallel induction by glucose of adherence and a polysaccharide antigen specific for plastic-adherent Staphylococcus epidermidis: evidence for functional relation to intercellular adhesion. Infect Immun. May 1992;60(5):2048-57.

Mack et al., Essential functional role of the polysaccharide intracellular adhesin of Staphylococcus epidermidis in hemagglutination. Infect Immun. Feb. 1999;67(2):1004-8.

Mack et al., Identification of three essential regulatory gene loci governing expression of Staphylococcus epidermidis polysaccharide intercellular adhesin and biofilm formation. Infect Immun. Jul. 2000;68(7):3799-807.

Maira-Litran et al., Deacetylated-poly-N-acetyl Glucosamine (dPNAG) Polysaccharide Conjugated to Diphtheria Toxoid (DT) Confers Protection Against Multiple Strains of Staphylococcus aureus in a Murine Model of Bacteremia. Abstracts of the 104th General Meeting of the American Society for Microbiology. Am Soc Microbiol. May 2004;abstract D-130. Abstract and corresponding presentation.

Maira-Litran et al., Synthesis and Immunological Properties of a Staphylococcal Deacetylated-poly-N-acetyl Glucosamine (dPNAG) Polysaccharide and Clumping Factor A (ClfA) Protein Conjugate Vaccine. Abstracts of the 104th General Meeting of the American Society for Microbiology. Am Soc Microbiol. May 2004;abstract E-062. Abstract and corresponding presentation.

McKenney et al., Broadly protective vaccine for Staphylococcus aureus based on an in vivo-expressed antigen. Science. May 28, 1999;284(5419): 1523-7.

McKenney et al., Vaccine potential of poly-1-6 beta-D-N-succinylglucosamine, an immunoprotective surface polysaccharide of Staphylococcus aureus and Staphylococcus epidermidis. J Biotechnol. Sep. 29, 2000;83(1-2):37-44.

Melean et al., Toward the automated solid-phase synthesis of oligoglucosamines: systematic evaluation of glycosyl phosphate and glycosyl trichloroacetimidate building blocks. Carbohydr Res. Nov. 19, 2002;337(21-23): 1893-916.

Milstein, From antibody structure to immunological diversification of immune response. Science. Mar. 14, 1986;231(4743): 1261-8.

Moch et al., Isolation and characterization of the alpha-sialyl-beta-2,3-galactosyl-specific adhesin from fimbriated Escherichia coli. Proc Natl Acad Sci U S A. May 1987;84(10):3462-6.

Moreau et al., Structure of the type 5 capsular polysaccharide of Staphylococcus aureus. Carbohydr Res. Jul. 1, 1990;201(2):285-97.

Muller et al., Occurrence of capsular polysaccharide/adhesin among clinical isolates of coagulase-negative Staphylococci. J Infect Dis. Nov. 1993;168(5):1211-8.

Nagy et al., Multi-adhesin vaccines for the protection of the neonatal piglet against "E. coli" infections. Dev Biol Stand. 1983;53:189-97.

Nakano, et al., Polyclonal antibody production in murine spleen cells induced by Staphylococcus. Microbiol Immunol. 1980;24(10):981-94. Abstract only.

Ohshima et al., Cell surface antigen of encapsulated Staphylococcus epidermidis ATCC 31432. J Clin Microbiol. Jul. 1987;25(7):1338-40.

Ohshima et al., Protection inducing antigen of an encapsulated Staphylococcus epidermis SE-10. in The Staphylococci, Zbl Bakt. 1991;Suppl 21:279-80.

Orskov et al., An adhesive protein capsule of Escherichia coli. Infect Immun. Jan. 1985;47(1):191-200.

Peters et al., Biology of S.epidermidis extracellular slime, in The Staphylococci, Zbl Bakt . 1987;Suppl 16:15-33.

Quie et al., Coagulase-negative staphylococcal adherence and persistence. J Infect Dis. Oct. 1987;156(4):543-7.

Rogemond et al., Lectinlike adhesins in the Bacteroides fragilis group. Infect Immun. Jul. 1986;53(1):99-102.

Rupp et al., Characterization of the importance of polysaccharide intercellular adhesin/hemagglutinin of Staphylococcus epidermidis in the pathogenesis of biomaterial-based infection in a mouse foreign body infection model. Infect Immun. May 1999;67(5):2627-32.

Rupp et al., Characterization of Staphylococcus epidermidis polysaccharide intercellular adhesin/hemagglutinin in the pathogenesis of intravascular catheter-associated infection in a rat model. Infect Immun. May 1999;67(5):2656-9.

Sanford et al., Detection of staphylococcal membrane receptors on virus-infected cells by direct adhesin overlay. Infect Immun. Jun. 1986;52(3):671-5.

Schumacher-Perdreau et al., Comparative analysis of a biofilm-forming Staphylococcus epidermidis strain and its adhesion-positive, accumulation-negative mutant M7. FEMS Microbiol Lett. Mar. 15, 1994;117(1):71-8.

Sompolinsky et al., Encapsulated and capsular types in isolates of Staphylococcus aureus from different sources and relationship to phage types. J Clin Microbiol. Nov. 1985;22(5):828-34.

Takeda et al., Protection against endocarditis due to Staphylococcus epidermidis by immunization with capsular polysaccharide/adhesin. Circulation. Dec. 1991;84(6):2539-46.

Thomas et al., Enzyme-linked lectinsorbent assay measures N-acetyl-D-glucosamine in matrix of biofilm produced by Staphylococcus epidermidis. Curr Microbiol. Oct. 1997;35(4):249-54.

Tojo et al., Isolation and characterization of a capsular polysaccharide adhesin from Staphylococcus epidermidis. J Infect Dis. Apr. 1988;157(4):713-22.

Tollersrud et al., Genetic and serologic evaluation of capsule production by bovine mammary isolates of Staphylococcus aureus and other Staphylococcus spp. from Europe and the United States. J Clin Microbiol. Aug. 2000;38(8):2998-3003.

Vershigora et al., Secretory antibodies to homologous and heterologous staphylococcal strains in the colostrum of rabbits. Zh Mikrobiol Epidemiol Immunobiol. 1980;88-90. Russian.

Vuong et al., A crucial role for exopolysaccharide modification in bacterial biofilm formation, immune evasion, and virulence. J Biol Chem. Dec. 24, 2004;279(52):54881-6. Epub Oct. 22, 2004.

Wang et al., The pgaABCD locus of Escherichia coli promotes the synthesis of a polysaccharide adhesin required for biofilm formation. J Bacteriol. May 2004;186(9):2724-34.

Wessels et al., Isolation and characterization of type IV group B Streptococcus capsular polysaccharide. Infect Immun. Apr. 1989;57(4):1089-94.

Wray et al., Identification and characterization of a uroepithelial cell adhesin from a uropathogenic isolate of *Proteus mirabilis*. Infect Immun. Oct. 1986;54(1):43-9.

Yamada, et al., Possible common biological and immunological properties for detecting encapsulated strains of *Staphylococcus epidermidis*. J Clin Microbiol. Oct. 1988;26(10):2167-72.

Yoshida et al., Mouse virulent strain of *Staphylococcus epidermidis*. Relation of antiphagocytic activity to the protection-inducing antigen. Jpn J Microbiol. Jun. 1976;20(3):209-17.

Yoshida et al., Immunological response to a strain of *Staphylococcus epidermidis* in the rabbit: production of protective antibody. J Med Microbiol. Nov. 1978;11(4):371-7. Abstract only.

Yoshida et al., Cross protection between a strain of *Staphylococcus epidermidis* and eight other species of coagulase-negative staphylococci. Can J Microbiol. Jul. 1988;34(7):913-5.

Youmans, *Staphylococci*, Staphylococcal Disease, and Toxic Shock Syndrome. in The Biologic and Clinical Basis of Infectious Diseases, Third Edition.. Youmans et al., eds. W.B. Saunders Company: Philadelphia, 1985. p. 618-29 and 738-9.

Ziebuhr et al., Detection of the intercellular adhesion gene cluster (ica) and phase variation in *Staphylococcus epidermidis* blood culture strains and mucosal isolates. Infect Immun. Mar. 1997;65(3):890-6.

Ziebuhr et al., A novel mechanism of phase variation of virulence in *Staphylococcus epidermidis*: evidence for control of the polysaccharide intercellular adhesin synthesis by alternating insertion and excision of the insertion sequence element IS256. Mol Microbiol. Apr. 1999;32(2):345-56.

Götz et al., *Staphylococcus* and biofilms. Mol Microbiol. Mar. 2002;43(6):1367-78.

Gerke et al., Experimental *Pseudomonas aeruginosa* infection of the mouse cornea. Infection and Immunity. 1971;3(2):209-16.

Maira-Litran et al., Comparative opsonic and protective activities of *Staphylococcus aureus* conjugate vaccines containing native or deacetylated Staphylococcal Poly-N-acetyl-beta-(1-6)-glucosamine. Infect Immun. Oct. 2005;73(10):6752-62. Abstract Only.

Pier et al., Isolation and characterization of a high-molecular-weight polysaccharide from the slime of *Pseudomonas aeruginosa*. Infect Immun. Dec. 1978;22(3):908-18.

Pier et al., Protective immunity induced in mice by immunization with high-molecular-weight polysaccharide from *Pseudomonas aeruginosa*. Infect Immun. Dec. 1978;22(3):919-25.

Pier et al., Further purification and characterization of high-molecular-weight polysaccharide from *Pseudomonas aeruginosa*. Infect Immun. Dec. 1983;42(3):936-41.

Allignet et al., Tracking adhesion factors in *Staphylococcus caprae* strains responsible for human bone infections following implantation of orthopaedic material. Microbiology. Aug. 1999;145 ( Pt 8):2033-42.

Arciola et al., In catheter infections by *Staphylococcus epidermidis* the intercellular adhesion (ica) locus is a molecular marker of the virulent slime-producing strains. J Biomed Mater Res. Mar. 5, 2002;59(3):557-62. Abstract Only.

Bhasin et al., Identification of a gene essential for O-acetylation of the *Staphylococcus aureus* type 5 capsular polysaccharide. Mol Microbiol. Jan. 1998;27(1):9-21. Abstract Only.

Cramton et al., Anaerobic conditions induced expression of polysaccharide intercellular adhesin in *Staphylococcus aureus* and *Staphylococcus epidermidis*. Infect Immun. Jun. 2001;69(6):4079-85.

Dobinsky et al., Influence of Tn917 insertion on transcription of the icaADBC operon in six biofilm-negative transposon mutants of *Staphylococcus epidermidis*. Plasmid. Jan. 2002;47(1):10-7. Abstract Only.

Fattom et al., Antigenic determinants of *Staphylococcus aureus* type 5 and type 8 capsular polysaccharide vaccines. Infect Immun. Oct. 1998;66(10):4588-92.

Fey et al., Characterization of the relationship between polysaccharide intercellular adhesin and hemagglutination in *Staphylococcus epidermidis*. J Infect Dis. Jun. 1999;179(6):1561-4. Abstract Only.

Fowler et al., The intercellular adhesin locus ica is present in clinical isolates of *Staphylococcus aureus* from bacteremic patients with infected and uninfected prosthetic joints. Med Microbiol Immunol (Berl). Apr. 2001;189(3):127-31. Abstract Only.

Frebourg et al., PCR-Based assay for discrimination between invasive and contaminating *Staphylococcus epidermidis* strains. J Clin Microbiol. Feb. 2000;38(2):877-80.

Gelosia et al., Phenotypic and genotypic markers of *Staphylococcus epidermidis* virulence. Clin Microbiol Infect. Apr. 2001;7(4):193-9. Abstract Only.

Heilmann et al., Further characterization of *Staphylococcus epidermidis* transposon mutants deficient in primary attachment or intercellular adhesion. Zentralbl Bakteriol. Jan. 1998;287(1-2):69-83. Abstract Only.

Ji et al., Regulated antisense RNA eliminates alpha-toxin virulence in *Staphylococcus aureus* infection. J Bacteriol. Nov. 1999;181(21):6585-90.

Ji et al., Identification of critical staphylococcal genes using conditional phenotypes generated by antisense RNA. Science. Sep. 21, 2001;293(5538):2266-9.

Kolberg et al., Monoclonal antibodies with specificities for *Streptococcus pneumoniae* group 9 capsular polysaccharides. FEMS Immunol Med Microbiol. Apr. 1998;20(4):249-55. Abstract Only.

Longworth et al., O-Acetylation status of the capsular-polysaccharides of serogroup Y and W135 *Meningococci* isolated in the UK. FEMS Immunol Med Microbiol. Jan. 14, 2002;32(2):119-23. Abstract Only.

Mack et al., Molecular mechanisms of *Staphylococcus epidermidis* biofilm formation. J Hosp Infect. Dec. 1999;43 Suppl:S113-25. Abstract Only.

Mack et al., Genetic and biochemical analysis of *Staphylococcus epidermidis* biofilm accumulation. Methods Enzymol. 2001;336:215-39.

McNeely et al., Antibody responses to capsular polysaccharide backbone and O-acetate side groups of *Streptococcus pneumoniae* type 9V in humans and rhesus macaques. Infect Immun. Aug. 1998;66(8):3705-10.

Michon et al., Structure activity studies on group C meningococcal polysaccharide-protein conjugate vaccines: effect of O-acetylation on the nature of the protective epitope. Dev Biol (Basel). 2000;103:151-160. Abstract Only.

Muller et al., Capsular polysaccharide/adhesin (PS/A) production by coagulase-negative *Staphylococci* (CNS) is associated with adherence to silastic tubing, 1989. p. 49. Abstract B-111.

Kelly-Quintos et al., Characterization of the opsonic and protective activity against *Staphylococcus aureus* of fully human monoclonal antibodies specific for the bacterial surface polysaccharide poly-N-acetylglucosamine. Infect Immun. May 2006;74(5):2742-50.

Joyce et al., Isolation, structural characterization, and immunological evaluation of a high-molecular-weight exopolysaccharide from *Staphylococcus aureus*. Carbohydr Res. Apr. 22, 2003;338(9):903-22.

Kossaczka et al., Synthesis and immunological properties of Vi and di-O-acetyl pectin protein conjugates with adipic acid dihydrazide as the linker. Infect Immun. Jun. 1997;65(6):2088-93.

Ohshima et al., Immunochemical characterization and biological properties of a cell surface antigen extracted from encapsulated *Staphylococcus epidermidis* strain SE-10. Zentralbl Bakteriol 1990;274:417-25.

GenBank Submission; NIH/NCBI; Accession No. DQ231549; Kelly-Quintos et al.; Printed May 9, 2006.

GenBank Submission; NIH/NCBI; Accession No. DQ231550; Kelly-Quintos et al.; Printed May 9, 2006.

GenBank Submission; NIH/NCBI; Accession No. DQ231551; Kelly-Quintos et al.; Printed May 9, 2006.

GenBank Submission; NIH/NCBI; Accession No. DQ231552; Kelly-Quintos et al.; Printed May 9, 2006.

GenBank Submission; NIH/NCBI; Accession No. DQ231553; Kelly-Quintos et al.; Printed May 9, 2006.

GenBank Submission; NIH/NCBI; Accession No. DQ231554; Kelly-Quintos et al.; Printed May 9, 2006.

Kelly-Quintos et al., Characterization of the opsonic and protective activity against *Staphylococcus aureus* of fully human monoclonal antibodies specific for the bacterial surface polysaccharide poly-N-acetylglucosamine. Infect Immun. May 2006;74(5):2742-50.

Pollack et al., Functional properties of isotype-switched immunoglobulin M (IgM) and IgG monoclonal antibodies to *Pseudomonas aeruginosa* lipopolysaccharide. Infect Immun. Nov. 1995;63(11):4481-8.

Preston et al., Prophylactic and therapeutic efficacy of immunoglobulin G antibodies to *Pseudomonas aeruginosa* lipopolysaccharide against murine experimental corneal infection. Invest Ophthalmol Vis Sci. Jun. 1997;38(7):1418-25. Abstract Only.

Preston et al., Production and characterization of a set of mouse-human chimeric immunoglobulin G (IgG) subclass and IgA monoclonal antibodies with identical variable regions specific for *Pseudomonas aeruginosa* serogroup O6 lipopolysaccharide. Infect Immun. Sep. 1998;66(9):4137-42.

Maira-Litran et al., Biologic properties and vaccine potential of the staphylococcal poly-N-acetyl glucosamine surface polysaccharide. Vaccine. Feb. 17, 2004;22(7):872-9.

GenBank Submission; NIH/NCBI; Accession No. AF086783; Cramton et al.; Printed Oct 1, 1999.

Excerpt from GenBank Submission; NIH/NCBI; Accession No. BA000018 nucleotides 2770021-2771880; Kuroda et al., Oct. 22, 2004 (last submission).

EBI Dbfetch Submission; EMBL-EBI; Accession No. U43366; Heilmann et al., Apr. 17, 2005 (last submission).

Fitzpatrick et al., Environmental regulation of biofilm formation in intensive care unit isolates of *Staphylococcus epidermidis*. J Hosp Infect. Nov. 2002;52(3):212-8.

O'Gara et al., *Staphylococcus epidermidis* biofilms: importance and implications. J Med Microbiol. Jul. 2001;50(7):582-7.

Maira-Litran et al., Relationship between the polysaccharide intercellular adhesin (PIA) and poly-n-succinyl b-1-6 glucosamine (PNSG) molecules produced by pathogenic *Staphylococi*. Abstract of the General meeting of the American Society for Microbiology. Orlando, Florida. May 20-24, 2001; pp. 283-284. Abstract # D-42.

Wessels et al., Structural properties of group B streptococcal type III polysaccharide conjugate vaccines that influence immunogenicity and efficacy. Infect Immun. May 1998;66(5):2186-92.

New York Times, Editorial, Another Very Scary Germ. Nov. 20, 2007. Accessed Apr. 22, 2009. <http://www.nytimes.com/2007/11/20/opinion/20tue2.html?_r=2&oref=slogin&pagewanted...> 2 pages.

Cerca et al., Comparative antibody-mediated phagocytosis of *Staphylococcus epidermidis* cells grown in a biofilm or in the planktonic state. Infect Immun. Aug. 2006;74(8):4849-55.

Cerca et al., Influence of batch or fed-batch growth on *Staphylococcus epidermidis* biofilm formation. Lett Appl Microbiol. 2004;39(5):420-4.

Cerca et al., Molecular basis for preferential protective efficacy of anitobidies directed to the poorly acetylated form of staphylococcal poly-N-acetyl-beta-(1-6)-glucosamine. Infect Immun. Jul. 2007;75(7):3406-13. Epub Apr. 30, 2007.

Cerca et al., Protection against *Escherichia coli* infection by antibody to the *Staphylococcus aureus* poly-N-acetylglucosamine surface polysaccharide. Proc Natl Acad Sci U S A. May 1, 2007;104(18):7528-33. Epub Apr. 19, 2007.

Huang et al., Risk of methicillin-resistant *Staphylococcus aureus* infection after previous infection or colonization. Clin Infect Dis. Feb. 1, 2003;36(3):281-5. Epub Jan. 17, 2003.

Kelly-Quintos et al., The role of epitope specificity in the human opsonic antibody response to the staphylococcal surface polysaccharide poly N-acetyl glucosamine. J Infect Dis. Dec. 1, 2005;192(11):2012-9. Epub Nov. 1, 2005.

Klevens et al., Invasive methicillin-resistant *Staphylococcus aureus* infections in the United States. JAMA. Oct. 17, 2007;298(15):1763-71.

Kropec et al., Poly-N-acetylglucosamine production in *Staphylococcus aureus* is essential for virulence in murine models of systemic infection. Infect Immun. Oct. 2005;73(10):6868-76.

Kuehnert et al., Methicillin-resistant-*Staphylococcus aureus* hospitalizations, United States. Emerg Infect Dis. Jun. 2005;11(6):868-72. Erratum in: Emerg Infect Dis. Sep. 2006;12(9):1472.

Maira-Litran et al., Comparative opsonic and protective activities of *Staphylococcus aureus* conjugate vaccines containing native or deacetylated Staphylococcal Poly-N-acetyl-beta-(1-6)-glucosamine. Infect Immun. Oct. 2005;73(10):6752-62. Erratum in: Infect Immun. Nov. 2005;73(11):7789.

Sack, Deadly Bacteria Found to Be More Common. New York Times. Oct. 17, 2007. Accessed Apr. 22, 2009. <http://www.nytimes.com/2007/10/17/health/17infect.html?pagewanted=print> 3 pages.

Zeller et al., JAMA patient page. MRSA infections. JAMA. Oct. 17, 2007;298(15):1826.

* cited by examiner

NUCLEIC ACID MOLECULES FOR ENHANCED PRODUCTION OF A BACTERIAL POLYSACCHARIDE AND METHODS OF USE THEREOF

RELATED APPLICATIONS

This application claims priority under 35 U.S.C. § 119(e) to U.S. Provisional Application No. Ser. No. 60/425,569, filed Nov. 12, 2002, and entitled "METHODS AND PRODUCTS FOR TREATING STAPHYLOCOCCAL INFECTIONS", the contents of which are herein incorporated by reference in their entirety.

GOVERNMENT SUPPORT

The present invention was supported in part by a grant from the United States National Institutes of Health AI46706, AI46707, 5T32AI07410, F32AI51892, and AI09626. The U.S. Government may retain certain rights in the invention.

FIELD OF THE INVENTION

The present invention relates to nucleic acid molecules and related compositions useful for altering production of polysaccharides from bacteria. The compositions are useful for producing polysaccharide as well as for therapeutics such as for the prevention and treatment of Staphylococcal infections. The invention also relates to methods of making and using polysaccharide based antigens, related antibodies and diagnostic kits and for inducing active and passive immunity using the polysaccharide material and antibodies thereto.

BACKGROUND OF THE INVENTION

Staphylococci are gram-positive bacteria which normally inhabit and colonize the skin and mucus membranes of humans. If the skin or mucus membrane becomes damaged during surgery or other trauma, the Staphylococci may gain access to internal tissues causing infection to develop. If the Staphylococci proliferate locally or enter the lymphatic or blood system, serious infectious complications such as those associated with Staphylococcal bacteremia may result. Complications associated with Staphylococcal bacteremia include septic shock, endocarditis, arthritis, osteomyelitis, pneumonia, and abscesses in various organs.

Staphylococci include both coagulase-positive organisms that produce a free coagulase and coagulase-negative organisms that do not produce this free coagulase. *Staphylococcus aureus* is the most common coagulase-positive form of Staphylococci. *S. aureus* generally causes infection at a local site, either extravascular or intravascular, which ultimately may result in bacteremia *S. aureus* is also a leading cause of acute osteomyelitis, and causes a small number of Staphylococcal pneumonia infections. Additionally, *S. aureus* is responsible for approximately 1-9% of the cases of bacterial meningitis and 10-15% of brain abscesses.

There are at least twenty-one known species of coagulase-negative Staphylococci, including *S. epidermidis, S. saprophyticus, S. hominis, S. warneri, S. haemolyticus, S. saprophiticus, S. cohnii, S. xylosus, S. simulans*, and *S. capitis. S. epidermidis* is the most frequent infection-causing agent associated with intravenous access devices, and the most frequent isolate in primary nosocomial bacteremias. *S. epidermidis* is also associated with prosthetic valve endocarditis.

*Staphylococcus* is also a common source of bacterial infection in animals. For instance, Staphylococcal mastitis is a common problem in ruminants including cattle, sheep, and goats. The disease is generally treated with antibiotics to reduce the infection but the treatment is a costly procedure and still results in a loss of milk production. The most effective vaccines identified to date are live, intact *S. aureus* vaccines administered subcutaneously. The administration of live vaccines, however, is associated with the risk of infection. For that reason, many researchers have attempted to produce killed *S. aureus* vaccines and/or to isolate capsular polysaccharides or cell wall components which will induce immunity to *S. aureus*. None of these attempts, however, has been successful.

SUMMARY OF THE INVENTION

The invention relates to the discovery of transcriptional control mechanisms of the ica locus. The invention is premised in part on the identification of a 5 nucleotide motif within the ica promoter region which has a functional role in transcriptional regulation of the ica locus. This motif may function independently of IcaR protein. The invention is further premised in part on the observation that IcaR protein binds to the promoter region of the ica locus and that disruption of the icaR coding region results in over-production of polysaccharide as well as resultant biofilm.

It has been discovered that modifications to the intercellular adhesion (ica) locus result in altered production of poly-N-acetyl glucosamine (PNAG). PNAG is a polysaccharide antigen present on the surface of virulent strains of Staphylococci. The present invention relates to methods and products useful for altering the production of polysaccharide thereby resulting in increased or decreased production of polysaccharide formed via the ica locus. The polysaccharide produced according to the methods described herein may be used to produce vaccines or antibodies that are useful in the immunization of humans and animals against infection by coagulase-negative and coagulase-positive Staphylococci.

In one aspect, the invention provides a method of producing a polysaccharide over-producing bacterium by introducing into a bacterium an ica nucleic acid operably linked to an ica regulatory nucleic acid, wherein the ica regulatory nucleic acid comprises (a) nucleic acid molecules which hybridize under stringent conditions to a nucleic acid molecule having a sequence of SEQ ID NO:2, have an addition, deletion or substitution in a region between and including nucleotides 9 and 43 of SEQ ID NO:2, and that enhance production of a polysaccharide from an ica locus, and (b) complements thereof.

In a related aspect, the invention provides a method of making a polysaccharide over-producing bacterium comprising recombinantly altering a specific TATTT nucleotide sequence in the ica promoter region. In one embodiment, the TATTT nucleotide sequence is deleted. In another embodiment, the TATTT nucleotide sequence is substituted with a five nucleotide non-wildtype nucleotide sequence. The five nucleotide non-wildtype substitution may have a sequence of ATAAA, but it is not so limited.

In another related aspect, the invention provides a recombinant polysaccharide over-producing bacterium that comprises an ica nucleic acid operably linked to an ica regulatory nucleic acid, wherein the ica regulatory nucleic acid comprises (a) nucleic acid molecules which hybridize under stringent conditions to a nucleic acid molecule having a sequence of SEQ ID NO:2, have an addition, deletion or substitution in a region between and including nucleotides 9 and 43 of SEQ ID NO:2, and that enhance production of a polysaccharide from an ica locus, and (b) complements thereof, wherein the bacterium is not MN8m.

Various embodiments apply equally to the aforementioned aspects (as well as other aspects of the invention). These are recited below.

In one embodiment, the ica regulatory nucleic acid comprises the nucleotide sequence of SEQ ID NO:1. In another embodiment, the ica regulatory nucleic acid comprises the nucleotide sequence between and including nucleotides 9 and 38 of SEQ ID NO: 1. This 30 nucleotide sequence flanks the 5 nucleotide deletion from MN8m.

In yet another embodiment, the ica regulatory nucleic acid comprises a deletion, addition or substitution in the region between and including nucleotides 24 and 28 of SEQ ID NO:2 (i.e., the 5 nucleotide span that is deleted in MN8m). In other embodiments, the ica regulatory nucleic acid comprises a five nucleotide non-wildtype substitution between and including nucleotides 24 and 28 of SEQ ID NO:2. In a related embodiment, the five nucleotide non-wildtype substitution has a sequence of ATAAA. It is to be understood that other non-wildtype substitutions can also be introduced into SEQ ID NO:2 in place of the TATTT sequence.

In this and other aspects of the invention, the bacterium is a Staphylococcus bacterium, such as Staphylococcus epidermidis, Staphylococcus aureus, Staphylococcus capitis, Staphylococcus caprae, Staphylococcus hemolyticus, Staphylococcus auricularis, Staphylococcus intermedius, Staphylococcus lugdunensis, Staphylococcus pasteuri, or Staphylococcus piscifermentans.

Various aspects of the invention may also involve measuring polysaccharide production from the bacterium, wherein a high level of polysaccharide production is indicative of a polysaccharide over-producing bacterium. In preferred embodiments, the polysaccharide is PNAG.

In another aspect, the invention provides a method of making a polysaccharide over-producing bacterium comprising introducing into a bacterium an ica nucleic acid operably linked to an ica regulatory nucleic acid, wherein the ica regulatory nucleic acid comprises a mutant icaR nucleic acid, and measuring polysaccharide production from the bacterium, wherein a high level of polysaccharide production is indicative of a polysaccharide over-producing bacterium. The polysaccharide may be PNAG.

In a related aspect, the invention provides a method of making a polysaccharide over-producing bacterium comprising recombinantly down-regulating wildtype IcaR protein production, and selecting a polysaccharide over-producing bacterium.

In one embodiment, the wildtype IcaR protein production is at a level lower than in a wildtype bacterium. In another embodiment, the wildtype IcaR protein production in the bacterium is zero. The bacterium may produce a mutant IcaR protein, which optionally binds to a target less efficiently than wildtype IcaR protein. The mutant IcaR protein may alternatively be a truncated IcaR protein.

In a related aspect, the invention provides a recombinant polysaccharide over-producing bacterium comprising a mutant icaR nucleic acid.

In one embodiment, the mutant icaR nucleic acid does not encode a wildtype IcaR protein, and optionally it does not encode a mutant IcaR protein either. In another embodiment, the mutant icaR nucleic acid comprises a frameshift mutation relative to a wildtype icaR nucleic acid. In still another embodiment, the mutant icaR nucleic acid encodes a truncated IcaR protein. In another embodiment, the mutant icaR nucleic acid encodes a mutant IcaR protein that binds to a target less efficiently than wildtype IcaR protein.

In other aspects the invention relates to a method of producing a bacterial polysaccharide by culturing the polysaccharide over-producing bacterium described herein in a growth medium, and harvesting the bacterial polysaccharide from the culture. Optionally the bacterial polysaccharide may be isolated from the supernatant to form an isolated bacterial polysaccharide composed of beta ($\beta$) 1-6 linked glucosamine polysaccharides having 0-100% substitution with acetate. In some embodiments, the polysaccharide so produced is either screened for a low acetate form (i.e., less than 50% acetate substitutions) or is further treated to produce a low acetate form. The bacterial polysaccharide may also be formulated as a vaccine, wherein it may be combined with an adjuvant.

According to other aspects, the invention is a method of producing an antibody to a bacterial polysaccharide by administering the isolated bacterial polysaccharide of the invention to a subject to produce an antibody, and harvesting antibody from the subject. The antibody may be subsequently isolated. In one embodiment the subject is a non-human subject, such as a rabbit or a mouse. In other embodiments the antibody is a polyclonal or monoclonal antibody. The polysaccharide may be administered to the subject with an adjuvant. In still a further embodiment, the method further comprises harvesting an antibody-producing cell from the subject and harvesting the antibody from the antibody-producing cell. The antibody-producing cell may be manipulated prior to antibody harvest. In one embodiment, the isolated bacterial polysaccharide is composed of $\beta$1-6 linked glucosamine units, wherein 0-100% of the units are acetate substituted. In some important embodiments, less than 50% of the units are acetate substituted.

An isolated nucleic acid molecule is provided according to other aspects of the invention. The nucleic acid comprises (a) nucleic acid molecules which hybridize under stringent conditions to a nucleic acid molecule having a sequence of SEQ ID NO:2, have an addition, deletion or substitution in a region between and including nucleotides 9 and 43 of SEQ ID NO:2, and that enhance production of a polysaccharide from an ica locus, and (b) complements thereof.

An expression vector comprising the isolated nucleic acid molecule operably linked to an ica gene, or a fragment thereof is also provided. Additionally the invention encompasses a host cell transformed or transfected with the expression vector.

In another aspect, the invention provides an isolated nucleic acid molecule that hybridizes under stringent conditions to SEQ ID NO:1, and spans (i.e., comprises) an MN8m mutation. As used herein, an "MN8m mutation" refers to the five nucleotide deletion found in strain MN8m. In some embodiments, the isolated nucleic acid molecule enhances production of a polysaccharide from an ica locus when operably linked to an ica nucleic acid. In other embodiments, the nucleic acid molecule is a fragment of an ica promoter region from strain MN8m. The fragment may have a length of at least 10, at least 20, at least 30, at least 40, at least 50, at least 60, at least 70, at least 80, at least 90, at least 100, at least 110, at least 120, at least 130, at least 140, at least 150, or at least 160 nucleotides in length. The sequences flanking the MN8m mutation need not be equidistant (i.e., the MN8m mutation need not be centered in the fragment). In one embodiment, the fragment has a nucleotide sequence between and including nucleotides 9 and 38 of SEQ ID NO:1. In still other aspects, the invention embraces nucleic acid molecules that comprise a mutation of the partial MN8m sequence. That is, only part of the MN8m five nucleotide sequence needs to be mutated (e.g., 1, 2, 3 or 4 nucleotides out of the five nucleotides are mutated). As used herein, the term "mutated" embraces additions, deletions or substitutions.

In various aspects, the invention provides methods for identifying agents that bind differentially to the wild-type and mutant promoter regions. Agents that bind to the mutant promoter region but not to the wild-type region are useful as markers of the mutant promoter, and as markers of PNAG over-producing bacteria. Such mutant promoters can be used in the generation of further over-producing bacteria. Agents that bind to the wild-type promoter region but not to the mutant region are useful as potential targets that could be manipulated in order to modulate PNAG synthesis.

A method for identifying an isolated binding agent is provided according to other aspects of the invention. The method involves contacting a first nucleic acid molecule having the sequence of SEQ ID NO:2 or a functionally equivalent fragment thereof with a candidate molecule and determining whether the candidate molecule binds to the first nucleic acid molecule, and contacting a second nucleic acid molecule having the sequence of SEQ ID NO:1 or a functionally equivalent fragment thereof with the candidate molecule and determining whether the candidate molecule binds to the second nucleic acid molecule. A candidate molecule that binds to either the first or the second nucleic acid molecule but not both is indicative of a binding agent. In embodiments of the above methods, the binding agent may bind with higher affinity to SEQ ID NO:1 than to SEQ ID NO:2, or alternatively, it may bind with higher affinity to SEQ ID NO:2 than to SEQ ID NO:1.

The method may optionally involve contacting a reporter construct containing the nucleic acid molecule with the isolated binding agent to determine if the isolated binding agent is a polysaccharide synthesis modulator, wherein the isolated binding agent is a polysaccharide synthesis modulator if the isolated binding molecule alters expression from the reporter construct.

As used herein, a functionally equivalent fragment of SEQ ID NO:2 is any fragment of SEQ ID NO:2 that can be used in a comparison with SEQ ID NO:1, and preferably a fragment that comprises the five nucleotide sequence that is deleted in MN8m. As used herein, a functionally equivalent fragment of SEQ ID NO:1 is a fragment that comprises the MN8m mutation.

The invention further provides compositions comprising the aforementioned binding agents. In one aspect, the invention provides a composition comprising an isolated binding agent that binds with greater affinity to a nucleic acid having a sequence of SEQ ID NO:1 than to SEQ ID NO:2. In another aspect, the invention provides a composition comprising an isolated binding agent that binds with greater affinity to a nucleic acid having a sequence of SEQ ID NO:2 than to SEQ ID NO:1.

Several embodiments can be equally applied to aspects relating to isolated ica locus binding agents. These are recited below.

The isolated binding agent may be an ica regulatory binding agent. Thus, in one embodiment, the candidate molecule inhibits transcription of an ica nucleic acid molecule upon binding selectively to the nucleic acid molecule having a sequence of SEQ ID NO:2. In another embodiment, it inhibits transcription of an ica nucleic acid molecule upon binding selectively to the nucleic acid molecule having a nucleotide sequence of SEQ ID NO:1.

In one embodiment, the candidate molecule is a nucleic acid molecule. In another embodiment, the candidate molecule is a peptide. The candidate molecule may be a small molecule, and may be derived from a small molecule library (i.e., it is then a library member). In yet another embodiment, the candidate molecule is conjugated to a detectable label. The detectable label may be selected from the group consisting of a radioactive label, an enzyme, a biotin molecule, an avidin molecule or a fluorochrome, but it is not so limited. The candidate molecule may also be conjugated to a cytotoxic agent.

A method of identifying an ica promoter sequence associated with polysaccharide overproduction comprising detecting a nucleic acid molecule having a sequence alteration from wildtype in a region between and including nucleotides 9 and 43 of SEQ ID NO:2.

In one embodiment, the nucleic acid molecule is detected by contacting a candidate nucleic acid with a first and a second nucleic acid amplification primer, wherein at least one of the first or second nucleic acid amplification primers is capable of hybridizing to a sequence of SEQ ID NO:1 and not capable of hybridizing to a sequence of SEQ ID NO:2, amplifying a primed nucleic acid molecule which hybridizes to the first and the second nucleic acid amplification primers, and detecting the presence of an amplified nucleic acid molecule.

In another embodiment, the nucleic acid molecule is detected by contacting a candidate nucleic acid with a first and a second nucleic acid amplification primer, wherein the first and second nucleic acid amplification primers respectively hybridize to nucleotide sequences 5' and 3' to nucleotides 24 and 28 of SEQ ID NO:2, amplifying a primed nucleic acid molecule which hybridizes to the first and the second nucleic acid amplification primers, and measuring and comparing the length of the amplified nucleic acid molecule to a first control amplified nucleic acid molecule comprising SEQ ID NO:1 or a second control amplified nucleic acid molecule comprising SEQ ID NO:2, wherein an amplified nucleic acid molecule that is (a) identical in length to a first control amplified nucleic acid molecule or (b) shorter than the second control amplified nucleic acid molecule is indicative of the presence of an ica promoter sequence associated with polysaccharide over-production.

In yet another embodiment, the nucleic acid molecule is detected by contacting a candidate nucleic acid with a nucleic acid probe that selectively binds to SEQ ID NO:1 and does not bind to SEQ ID NO:2, and detecting the presence of the bound probe.

In one embodiment, the candidate nucleic acid is present in a bacterial isolate from a subject. In another embodiment, the candidate nucleic acid is present in a bacterial culture.

In still another aspect, the invention provides a method for identifying an ica regulatory nucleic acid molecule that enhances polysaccharide production comprising altering a nucleic acid molecule having a sequence of SEQ ID NO:2, and determining a level of reporter production by a bacterium that comprises the altered nucleic acid molecule operably linked to reporter nucleic acid, wherein a higher than wild-type level of reporter protein production is indicative of an ica regulatory nucleic acid molecule that enhances polysaccharide production.

In one embodiment, the reporter nucleic acid is an ica nucleic acid and reporter production is polysaccharide production. In another embodiment, the nucleic acid molecule is altered recombinantly. In still another embodiment, the nucleic acid molecule is altered naturally during bacterial culture.

In still other aspects, the invention provides methods for over-producing proteins from a bacterium that harbors an ica regulatory nucleic acid. In these embodiments, the ica regulatory nucleic acid comprises either a mutation of the five nucleotide motif which is mutated in MN8m (and preferably comprises a mutation of the five nucleotide motif) or a mutation in the icaR coding sequence.

Thus, the invention provides a method of over-producing a protein in a bacterium comprising introducing into a bacterium a nucleic acid operably linked to an ica regulatory nucleic acid, wherein the ica regulatory nucleic acid comprises (a) nucleic acid molecules which hybridize under stringent conditions to a nucleic acid molecule having a sequence of SEQ ID NO:2, have an addition, deletion or substitution in a region between and including nucleotides 9 and 43 of SEQ ID NO:2, and that enhance production of a polysaccharide from an ica locus, and (b) complements thereof. The nucleic acid encodes a protein to be over-produced.

In one embodiment, the ica regulatory nucleic acid comprises the nucleotide sequence of SEQ ID NO:1. In another embodiment, the ica regulatory nucleic acid comprises the nucleotide sequence between and including nucleotides 9 and 38 of SEQ ID NO:1. In still another embodiment, the ica regulatory nucleic acid comprises a deletion, addition or substitution in the region between and including nucleotides 24 and 28 of SEQ ID NO:2. The ica regulatory nucleic acid may comprise a five nucleotide non-wildtype substitution between and including nucleotides 24 and 28 of SEQ ID NO:2. In a related embodiment, the five nucleotide non-wildtype substitution has a sequence of ATAAA.

The invention provides a related method of over-producing a protein in a bacterium comprising introducing into a bacterium a nucleic acid operably linked to an ica regulatory nucleic acid, wherein the ica regulatory nucleic acid comprises a mutant icaR nucleic acid. The nucleic acid encodes the protein to be over-produced.

In one embodiment, the mutant icaR nucleic acid does not encode a wildtype IcaR protein. In another embodiment, the mutant icaR nucleic acid comprises a frameshift mutation relative to a wildtype icaR nucleic acid. In yet another embodiment, the mutant icaR nucleic acid encodes a truncated IcaR protein. In a further embodiment, the mutant icaR nucleic acid encodes a mutant IcaR protein that binds to a target less efficiently than wildtype IcaR protein.

In these and other aspects relating to the use of an ica regulatory nucleic acid and a mutant icaR coding sequence, the ica regulatory nucleic acid may further comprise a wildtype promoter.

Various embodiments apply equally to these protein production methods and these are recited below.

In one embodiment, the bacterium is a *Staphylococcus* bacterium. In a related embodiment, the *Staphylococcus* bacterium is selected from the group consisting of *Staphylococcus epidermidis, Staphylococcus aureus, Staphylococcus capitis, Staphylococcus caprae, Staphylococcus hemolyticus, Staphylococcus auricularis, Staphylococcus intermedius, Staphylococcus lugdunensis, Staphylococcus pasteuri*, and *Staphylococcus piscifermentans*.

The protein to be over-produced may be virtually any protein. For example, the protein may be a therapeutic protein to be used in human and veterinary protocols. An example of a therapeutic protein is fibrinogen-binding protein, as well as clotting factors. Other examples include growth hormones, growth factors, cytokines, antigens, peptides, and the like. The protein may also be used prophylactically in these same subjects. The protein may also be a protein routinely contained in a vaccine (i.e., a vaccine carrier protein) such as a protein with adjuvant activities. The protein may also be a hapten.

The protein may also be a protein useful as a substrate or analyte for assay purposes. Examples include IcaA, IcaD, IcaB and IcaC. The protein can also be a marker or reporter such as a fluorescent protein. Examples of fluorescent proteins include but are not limited to green fluorescent protein, yellow fluorescent protein and cyan fluorescent protein.

The protein may derive from any source including bacterial, viral, fungal, parasite, or mammalian sources. Examples of bacterial proteins include Staphylococcal clumping factor A, Staphylococcal clumping factor B, Staphylococcal protein A, or Streptococcal protein G.

The methods can further comprise harvesting the protein from the supernatant or from the bacteria themselves and optionally isolating or purifying the proteins. In some embodiments, protein production from the bacterium can be measured in order to identify over-producing bacteria.

The invention also intends to embrace the bacteria generated by these methods, and the nucleic acids used in the generation of such bacteria.

According to another aspect of the invention, a method is provided for treating a subject having an infection characterized by the presence of a nucleic acid molecule comprising a nucleotide sequence of SEQ ID NO:1 by administering the isolated binding agent that binds selectively to a nucleic acid molecule having a nucleotide sequence of SEQ ID NO:1 to a subject in need of such treatment in an amount effective to treat the subject. The infection is not an MN8m infection.

In one embodiment the disorder is a Staphylococcus infection, such as *Staphylococcus epidermidis* infection, *Staphylococcus aureus* infection, *Staphylococcus capitis* infection, *Staphylococcus caprae* infection, *Staphylococcus hemolyticus* infection, *Staphylococcus auricularis* infection, *Staphylococcus intermedius* infection, *Staphylococcus lugdunensis* infection, *Staphylococcus pasteuri* infection, and *Staphylococcus piscifermentans* infection Each of the limitations of the invention can encompass various embodiments of the invention. It is therefore anticipated that each of the limitations of the invention involving any one element or combinations of elements can be included in each aspect of the invention.

BRIEF DESCRIPTION OF THE SEQUENCE LISTING

SEQ ID NO:1 is the nucleotide sequence of the promoter region of the ica locus containing a 5 nucleotide deletion from MN8m.

SEQ ID NO:2 is the nucleotide sequence of the promoter region of the wild type ica locus from either SA113 or MN8.

SEQ ID NO:3 is the nucleotide sequence of wild type ica locus from *S. aureus* which has been deposited in GenBank under accession number AF086783.

SEQ ID NO:4 is the nucleotide sequence of the 5 nucleotide deletion in MN8m.

SEQ ID NO:5 is the nucleotide sequence of icaRF primer.
SEQ ID NO:6 is the nucleotide sequence of icaRR primer.
SEQ ID NO:7 is the nucleotide sequence of DelFwd primer.
SEQ ID NO:8 is the nucleotide sequence of DelRev primer.
SEQ ID NO:9 is the nucleotide sequence of SubFwd primer.
SEQ ID NO:10 is the nucleotide sequence of WTshort primer.
SEQ ID NO:11 is the nucleotide sequence of SUB primer.
SEQ ID NO:12 is the nucleotide sequence of MUC primer.
SEQ ID NO:13 is the nucleotide sequence of icaFWD primer.
SEQ ID NO:14 is the nucleotide sequence of icaREV primer.

SEQ ID NO:15 is the nucleotide sequence of a 198 bp wildtype probe used in gel shift analysis.

SEQ ID NO:16 is the nucleotide sequence of a 193 bp mutant probe used in gel shift analysis.

SEQ ID NO:17 is the nucleotide sequence of a 53 bp wildtype probe used for DNA affinity chromatography.

SEQ ID. NO:18 is the nucleotide sequence of a 48 bp mutant probe used for DNA affinity chromatography.

SEQ ID NO:19 is the nucleotide sequence of a wildtype icaR nucleic acid from S. aureus (GenBank Accession No. AF086783).

SEQ ID NO:20 is the amino acid sequence of a wildtype IcaR protein from S. aureus (GenBank Accession No. AF086783).

DETAILED DESCRIPTION OF THE INVENTION

Figure 1:
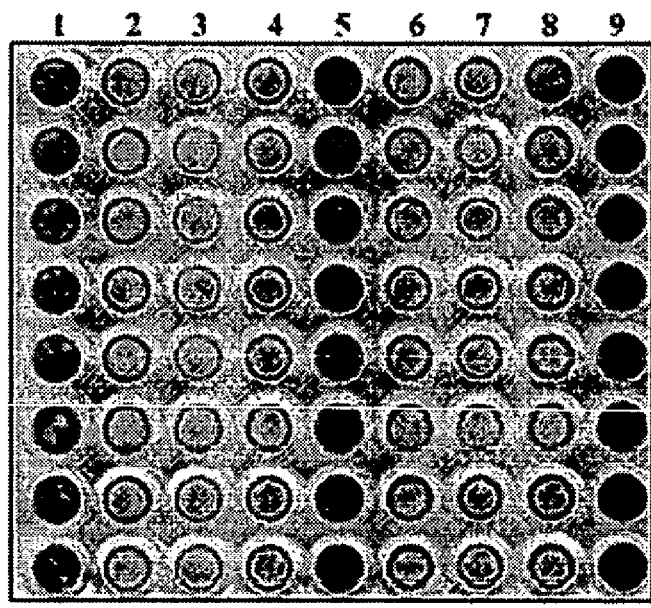
FIG. 1 shows biofilm elaboration by S. aureus strains expressing either the wild type ica locus from S. aureus strain MN8 (pWT) or the ica locus from strain MN8m (pMUC). Bacteria were grown in microtiter wells in TSB+1% glucose overnight. The wells were washed and stained with safranin. Strains expressing the ica locus from strain MN8m produced a strong biofilm. The Staphylococcal strains and plasmids they carry areas follows: Lane 1: MN8m; Lane 2: MN8; Lane 3: MN8Dica::tet; Lane 4: MN8Dica::tet/pWT; Lane 5: MN8Dica::tet/pMUC; Lane 6: 10833; Lane 7: 10833Dica:: tet; Lane 8: 10833Dica::tet/pWT; Lane 9: 10833Dica::tet/ pMUC. The biofilm assay was repeated a minimum of 3 times with similar results.

Communication between bacterial cells allows them to sense and adapt to their surroundings. One such method of adaptation is the formation of a complex, structured multicellular network called a biofilm. A major component required for biofilm formation is production of an extracellular glycocalyx, which is principally composed of polysaccharides of bacterial origin. *S. aureus* which is known for its genetic plasticity and ability to thrive under a variety of adverse conditions, is thought to regulate the production of this glycocalyx in response to its environment.

The major component of the *S. aureus* glycocalyx is polymeric beta ($\beta$)-1,6-linked N-acetyl glucosamine (PNAG). PNAG production and biofilm elaboration protect the bacteria from both the host immune system and antibiotics, and can therefore complicate the treatment of *S. aureus* infections. Once an *S. aureus* biofilm has been established on an implanted medical device, the infection can be difficult to treat and may require removal of the infected device and repair of damaged tissue.

Production of the polysaccharide is dependent upon the proteins encoded by the intercellular adhesion (ica) locus, originally detected in *Staphylococcus epidermidis* and later found by McKenney et al. and Cramton et al. to be present in *S. aureus* (Cramton et al, 1999; Heilmann et al., 1996; McKenney et al., 1998). The ica locus is made up of five genes: icaR, icaA, icaD, icaB and icaC. The icaR gene is transcribed divergently from the other 4 genes, and the icaA, B, C, and D genes appear to be translated from a single transcript.

The invention is based in part on a characterization of mechanisms through which transcription of the ica locus, and synthesis of the polysaccharide and biofilm are regulated. These findings are based on analysis of using isogenic *S. aureus* MN8 and MN8mucoid (MN8m) strains, the latter of which constitutively over-produces biofilm.

It was discovered according to the invention that transformation of the ica locus from MN8m to the ica knockout mutants of two strains, MN8 and NCTC 10833, conferred a strong biofilm producing phenotype. Sequence analysis revealed a 5-nucleotide deletion within the promoter region of the ica locus in MN8m compared with the sequence in the wild-type locus. Mutation of these 5 nucleotides, for example in the form of a deletion or a substitution, within the wildtype ica locus augmented transcription of the ica locus and induced the strong biofilm-producing phenotype.

Gel shift analysis demonstrated that one or more proteins within cell-free lysates from strain MN8 bound specifically to oligonucleotides representative of the wildtype ica promoter sequence but not to oligonucleotides in which the 5 nucleotides were either deleted or substituted.

Prior to the invention, the IcaR protein was postulated to be a regulatory factor controlling the ica locus. The amino-terminal third of IcaR exhibits 72% homology and 40% identity with other regulatory proteins of the TetR family. It was also shown according to the invention that purified IcaR binds to the ica promoter sequence independently of the deletion of the 5 nucleotide motif, suggesting that IcaR binding alone is not the determinative factor in biofilm over-production.

The invention is also premised on the finding that mutation of IcaR protein resulted in increased polysaccharide production from bacteria. This was surprising because mutation of other proteins that negatively regulate the ica operon does not necessarily correlate with increased polysaccharide production even if transcription from the ica locus is upregulated.

Thus, the invention relates to methods of altering the production of polysaccharides from bacteria, methods for generating polysaccharide over-producing bacteria, nucleic acids used to generate such bacteria, and the bacteria themselves. The polysaccharides are useful for inducing immunity to bacterial infection and also for producing antibodies for diagnostic and therapeutic purposes.

Naturally occurring PNAG was previously identified and characterized as a portion of the capsule of coagulase-negative Staphylococci (U.S. Pat. No. 5,055,455, issued to Gerald B. Pier). It was found that the PNAG of coagulase-negative *Staphylococcus* is a component of the cell surface and biofilm layer and is involved in protecting the bacterial cell from host defenses, such as opsonophagocytosis (Kojima, Y., et. al., (1990) *J Infect Dis.* 162:435. Tojo, M. et. al., (1988) *J Infect Dis.* 157:713. and Goldmann, D. A. and G. B. Pier. (1993) *Clin Microbiol Rev.* 6:176.) The chemical structure of the PNAG, however, was not identified because of the difficulty associated with purifying the isolated PNAG. It was only possible to achieve a preparation of approximately 90% purity. Subsequently, the PNAG antigen was isolated and purified to achieve a pure PNAG preparation (McKenney et al, *Science*, 1999, 284: 1523-1527). Production of large quantities of pure PNAG for therapeutic, diagnostic, or research purposes, however, has been difficult.

Figure 2:
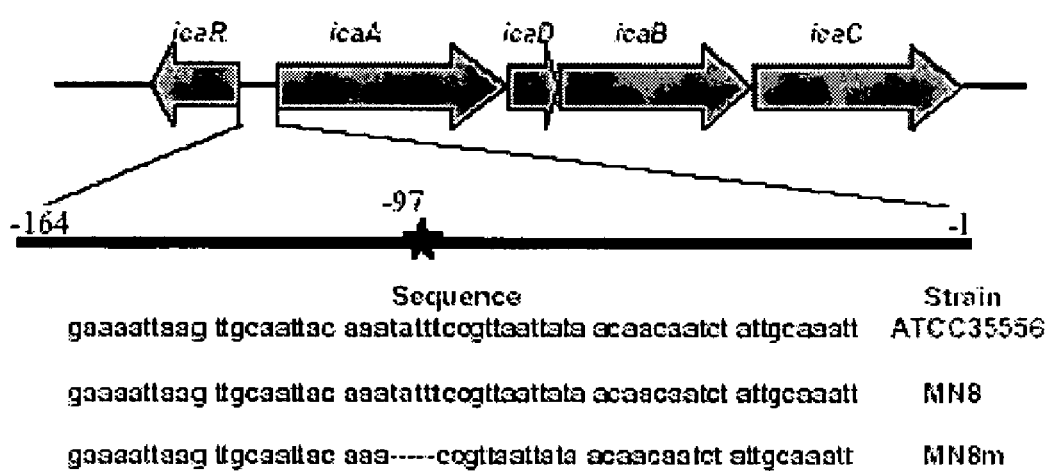
FIG. 2 shows the sequence comparison of the ica promoters of S. aureus strains MN8 and MN8m. This diagram illustrates the organization of the ica locus. The promoter region of the ica locus is located between icaR and icaA. This illustration compares the sequences of S. aureus strains ATCC 35556 (SA113) (published sequence for Accession number AF086783) (GAA AAT TAA GTT GCA ATT ACA AAT ATT TCC GTT AAT TAT AAC AAC AAT CTA TTG CAA ATT; SEQ ID NO:2), MN8 (GAA AAT TAA GTT GCA ATT ACA AAT ATT TCC GTT AAT TAT AAC AAC AAT CTA TTG CAA ATT; SEQ ID NO:2), and MN8m (GAA AAT TAA GTT GCA ATT ACA AA- --- -CC GTT AAT TAT AAC AAC AAT CTA TTG CAA ATT; SEQ ID NO:1). A 5-nucleotide deletion was found in the ica promoter region of the PNAG-overproducing strain MN8m (indicated by dashes).

A spontaneous over-producing strain of *S. aureus* termed MN8m derived from strain MN8 has been isolated and cultured (McKenney et al, *Science*, 1999, 284: 1523-1527). It has now been discovered, according to the invention, that a five base pair deletion in the nucleotide sequence of the promoter region of the ica locus of *S. aureus* strain MN8m is associated with the PNAG over-production capability of this strain. The mutation is shown in SEQ ID NO:1 which represents a 55 nucleotide fragment from the MN8m ica promoter. A schematic of the ica locus is shown in FIG. 2. Also shown in FIG. 2 is a comparison of the sequences of this region in *S. aureus* strain ATCC 35556 (published sequence: Accession number AF086783), MN8 and MN8m. In the Figure, the promoter region of ica is located between icaR and icaA. The 5 nucleotide deletion is located in this region, and has a sequence of TATTT (SEQ ID NO:4).

The identification of the genetic basis for PNAG over-production has broad implications for diagnostics and therapeutics in the field of Staphylococcal infection. For instance, bacteria may be manipulated to generate strains carrying the mutated ica promoter. Such bacteria can be used to generate large quantities of PNAG. One method for accomplishing this involves the introduction of a nucleic acid molecule comprising the ica locus containing the 5 base pair deletion into any bacteria and preferably Staphylococci strains. *Staphylococcus* bacteria include but are not limited to *Staphylococcus epidermidis, Staphylococcus aureus, Staphylococcus capitis, Staphylococcus caprae, Staphylococcus hemolyticus, Staphylococcus auricularis, Staphylococcus intermedius, Staphylococcus lugdunensis, Staphylococcus pasteuri* and *Staphylococcus piscifermentans*.

In one method provided herein, a polysaccharide over-producing bacterium is made by introducing into a bacterium, such as those listed above, an ica nucleic acid operably linked to an ica regulatory nucleic acid, wherein the ica regulatory nucleic acid comprises (a) nucleic acid molecules that hybridize under stringent conditions to a nucleic acid molecule having a sequence of SEQ ID NO:2, have an addition, deletion or substitution in a region between and including nucleotides 9 and 43 of SEQ ID NO:2, and enhance production of a polysaccharide from an ica locus, and (b) complements thereof. Preferably, the nucleic acid molecule harbors at least a mutation at the 5 nucleotide motif that is characteristic of the MN8m strain. Mutation at the 5 nucleotide motif embraces an addition, deletion or substitution of one or more nucleotide in the motif.

As used herein, an "ica nucleic acid" is a nucleic acid molecule coding for IcaA, D, B or C. In preferred embodiments, the ica nucleic acid encodes all four genes and is thus referred to as the ica operon. It comprises the structural genes required for PNAG synthesis. This nucleic acid molecule is located downstream of the promoter region of the ica locus. It does not include the icaR coding sequence which is located upstream of the promoter region. SEQ ID NO:3 is the nucleotide sequence of the entire ica locus, including the icaR coding sequence, the promoter and the ica operon.

As used herein, an "ica regulatory nucleic acid" is a nucleotide sequence involved in transcriptional regulation of the ica locus. An ica regulatory nucleic acid may function by coding regulatory factors, such as icaR nucleic acid, or it may be acted upon by regulatory factors, such as the ica promoter region. In some embodiments, an ica regulatory nucleic acid is operably linked to an ica nucleic acid. In other embodiments, the ica regulatory nucleic acid is operably linked to one but not all of the structural genes encoded by the ica operon (e.g., icaA but not icaADBC). It may also be operably linked to a reporter coding sequence or a coding sequence for a protein which is to be over-produced (e.g., a therapeutic protein).

The ica regulatory nucleic acid may be wildtype or mutant. In preferred embodiments, it is mutant and comprises mutations in the five nucleotide motif which is mutated in MN8m, or mutations in the icaR coding sequence (resulting in mutant IcaR protein synthesis), or both. In some embodiments, the ica regulatory nucleic acid comprises a mutation in the icaR coding sequence and the wildtype promoter, or vice versa.

For example, the ica regulatory nucleic acid may comprise the nucleotide sequence of SEQ ID NO:1. It may alternatively comprise fragments of SEQ ID NO:1 that themselves comprise the MN8m mutation. For example, the ica regulatory nucleic acid may comprise the nucleotide sequence between and including nucleotides 9 and 38 of SEQ ID NO:1. This 30 nucleotide sequence flanks the 5 nucleotide deletion from MN8m (i.e., there are 15 nucleotides upstream and downstream of the MN8m mutation). The fragment can be any length ranging, as an example, from 10 nucleotides to 160 nucleotides. The ica regulatory nucleic acid may also be a nucleic acid that comprises a mutation at the 5 nucleotide motif that is not a complete deletion as found in MN8m. Other mutations of the MN8m 5 nucleotide motif may also be part of the ica regulatory nucleic acid and these include additions and substitutions (as described herein).

The promoter region of the ica locus is approximately 163 nucleotides long (from the icaR transcriptional start site to the icaA transcriptional start site). In the MN8m strain, the promoter lacks a 5 nucleotide stretch of TATTT. A 55 nucleotide fragment of the MN8m promoter is provided as SEQ ID NO:1. A 60 nucleotide fragment of wildtype promoter is provided as SEQ ID NO:2. It is to be understood that any nucleic acid comprising a mutation at the 5 nucleotide motif may be used to enhance polysaccharide production from a bacterium. Thus, promoter sequences that comprise a mutation (e.g., a deletion, addition or substitution) at the 5 nucleotide motif can be any length up to the wildtype length of the promoter (e.g., approximately 163 nucleotides). The promoter fragments can thus be at least 10, at least 20, at least 30, at least 40, at least 50, at least 60, at least 70, at least 80, at least 90, at least 100, at least 110, at least 120, at least 130, at least 140, at least 150 or at least 160 nucleotides in length. These sequences and methods for delivery of these sequences into the cell are described in more detail below.

It is to be understood that SEQ ID NO:1 fragments to be used as ica regulatory nucleic acids do not necessarily comprise a mutation at the MN8m 5 nucleotide motif, but in important embodiments they do. For example, the mutation may occur in sequence flanking the 5 nucleotide motif, and will still have the same effect on transcription of the operably linked locus (e.g., ica locus, reporter gene, etc.). As stated previously, the mutation may be an addition, a deletion or a substitution of wildtype sequence. Deletions and substitutions, particularly those relating to the MN8m 5 nucleotide motif may be complete (i.e., affecting all 5 nucleotides) or partial (affecting fewer than all five nucleotides).

In another method, the polysaccharide over-producing bacterium is made by recombinantly altering the TATTT nucleotide sequence in the ica promoter region. The TATTT nucleotide sequence may be deleted, in whole or in part, or it may be substituted in whole or in part to generate a non-wildtype sequence. An example of a five nucleotide non-wildtype substitution is replacement of the wildtype TATTT sequence with an ATAAA sequence. The substituting sequence may be AT-rich, but it is not so limited. Other examples of 5 nucleotide substitutions include ACGTA, TATCG, TGCTG, AAACC, CGATC, GCTAT, TATGG, TATAA, AAAAA, TTTTT, CCCCC, GGGGG, and so on. Although not intending to be bound to any particular theory, it is possible that the sequence of the 5 nucleotide motif controls the conformation of the promoter in that region. That is, for the promoter to be bound by a negative regulatory factor, such as a repressor, it may need to adopt a particular conformation, such as a bend.

The polysaccharide over-producing bacteria can also be made by introducing into a bacterium an ica nucleic acid operably linked to an ica regulatory nucleic acid, wherein the ica regulatory nucleic acid comprises a mutant icaR nucleic acid. As used herein, an "icaR nucleic acid" is a nucleic acid molecule that hybridizes under stringent conditions to SEQ ID NO:19 and that codes for a wildtype IcaR protein. Wildtype IcaR protein is a protein capable of binding to the ica promoter region, preferably in a region encompassed by 42 nucleotides just upstream of the transcriptional start site of icaA, as described below, and thereby repressing transcription from the ica operon. "Mutant icaR nucleic acid" is a nucleic acid that fails to code for wildtype levels of wildtype IcaR protein. The mutant icaR nucleic acid may be a complete deletion of the icaR coding region. Alternatively, it may comprise a frameshift mutation, or a premature stop codon (resulting in a truncated IcaR protein), or an interruption to the reading frame of wildtype icaR. The mutant IcaR protein can be a truncated form of the wild type IcaR protein. Mutant IcaR proteins also include proteins that do not bind to IcaR targets as efficiently as do wild type IcaR proteins. An example of an IcaR target is the region defined by nucleotides 150-192 of the ica promoter region, wherein nucleotide 198 denotes the transcriptional start site for icaA and nucleotide 29 denotes the transcriptional start site for icaR. (See, for example, Jefferson et al. Molecular Microbiology, 48(4):889-899 (2003).)

The polysaccharide over-producing bacterium can also be made by recombinantly down-regulating wildtype IcaR protein production, and selecting a polysaccharide over-producing bacterium. "Down-regulating wildtype IcaR protein production" can be achieved by decreasing the levels of wildtype IcaR protein produced, or by producing a mutant IcaR protein in place of wildtype IcaR protein. For example, the wildtype IcaR protein production may be at a level lower than in a wildtype bacterium, and in some embodiments, it may be zero.

The ica regulatory nucleic acids (either wildtype or mutant), ica nucleic acids, reporter sequences and the like may be introduced into the bacterium using methods known in the art. For instance, the cell may be transfected, transduced or transformed with the nucleic acid.

The bacteria made according to the aforementioned methods can be screened and thereby selected based on their ability to over-produce polysaccharide such as PNAG. As used herein, "over-produce" refers to a production of a polysaccharide (preferably PNAG) at a level that exceeds polysaccharide production in a wildtype bacterium. Polysaccharide levels can be determined using the biofilm assays described in the Examples (e.g., PNAG slot blot assay). When the invention is used to over-produce proteins such as therapeutic proteins, "over-produce" refers to production of the protein at a level that exceeds the level of that protein in a wildtype bacterium. In some instances the protein to be produced is not a bacterial protein, and accordingly levels in excess of zero are representative of protein "over-production".

The invention further provides the bacteria made according to the above methods. In some embodiments, particularly those relating to bacterium harboring MN8m mutations or equivalents thereof, the bacterium is not MN8m. Preferably, the bacterium is a *Staphylococcus* bacterium, such as but not limited to *Staphylococcus* bacterium, such as *Staphylococcus epidermidis, Staphylococcus aureus, Staphylococcus capitis, Staphylococcus caprae, Staphylococcus hemolyticus, Staphylococcus auricularis, Staphylococcus intermedius, Staphylococcus lugdunensis, Staphylococcus pasteuri*, or *Staphylococcus piscifermentans*.

Once bacteria comprising the nucleic acid are generated, they can be grown in large quantities and cultured to allow production of the PNAG. The PNAG may then be isolated from the culture media or the bacteria themselves. The amount of polysaccharide produced by the bacterium can be assessed using methods described herein.

Over-producing bacteria may be cultured in any growth medium supporting the growth of the particular bacterial strains. A preferred growth medium for Staphylococci is a chemically defined medium (CDM) (Hussain, M. et. al., 1991. *J. Med. Microbiol* 34:143) composed of RPMI-1640 AUTO-MOD, an RPMI-1640 preparation modified to allow sterilization by autoclaving; (Sigma Chemical Co., St. Louis, Mo.) as a starting base. Phenol red may be omitted because it readily binds to purified PNAG. The CDM is supplemented with additional amino acids, vitamins, and nucleotides to give it a final composition similar to that described elsewhere (Hussain, M., et. al., 1991. *J. Med. Microbiol.* 34:143). The medium may be further supplemented with dextrose and sucrose at a final concentration of 1%. Preferred medium for growth of *S. aureus* is columbia broth or brain heart infusion broth supplemented with glucose at 0.25% (v/v).

In general, cultures may be inoculated with a single colony of bacteria transfected, transduced or transformed with the nucleic acids described herein and grown on an agar plate such as trypticase soy agar. Cultures are typically grown with vigorous mixing at 37° C., with 2 L of O₂/min bubbled through via a sparger and the pH maintained at around 7.0 by addition of a base such as 5 M NaOH with a pH titrator. Cultures are preferably grown until they cease to need addition of NaOH to maintain the pH at 7.0 (i.e., for 48-72 hours).

An impure PNAG can be prepared from the cultured bacteria by a variety of methods. Large quantities of impure material may be used directly or further purified to produce pure PNAG. An example of a method for isolating impure PNAG involves extracting a crude PNAG preparation from a bacterial culture, isolating a high molecular weight PNAG-enriched material from the crude PNAG preparation, and precipitating an impure PNAG containing the high molecular weight PNAG-enriched material with a solvent such as methanol, ethanol, acetone or any other organic solvent known to one skilled in the art as being capable of causing the precipitation of polysaccharides from aqueous solutions. The steps of extracting the crude PNAG preparation and isolating and precipitating the impure PNAG antigen preparation are performed by any methods known in the art, such as those including U.S. Pat. No. 5,055,455.

The purification steps are achieved by incubating the impure PNAG antigen with bacterial enzymes that can digest biological materials, including nucleases such as DNase and RNase to digest DNA and RNA, proteases such as proteinase K to digest proteins, addition of a solvent that will precipitate PNAG out of solution, collection of the precipitate and re-dissolution of PNAG in a base, such as NaOH or an acid such as HCl, followed by neutralization. The neutralization can be accomplished using a base if the incubation step was performed with an acid, or with an acid if the incubation step was performed with a base. The insoluble fraction from the neutral material is then treated, e.g., by incubation in hydrofluoric acid to produce a pure PNAG antigen or by re-dissolution in buffers with a pH<4.0 followed by molecular sieve and/or ion-exchange chromatography to achieve a pure PNAG preparation. PNAG in a crude impure form may also be extracted from the bacterial cells directly into the culture supernatant with use of extraction conditions such as divalent cations, low pH, and heat. An exemplary method involves the addition of MgCl₂ to the culture to a final concentration of 100 mM, followed by an adjustment of the pH to 5.0. The culture is then heated and stirred. A temperature of 65° C. for 90 min is generally satisfactory. The cell bodies are sedimented at 9000×g for 15 min. The supernatant is concentrated to ~1000 ml via tangential-flow filtration (10,000 molecular weight (MW) cutoff filter), and buffer exchanges and treatments are performed while the solution is still in the filtration device. The buffer is exchanged with deionized H₂O adjusted to a pH of 5.0 (to remove excesses of Mg²⁺ ions).

Exemplary methods for preparing the crude PNAG from the bacterial cells may vary depending on the type of host cell. For instance, methods for isolating PNAG from *S. aureus* will vary slightly from the methods described above. These types of variations are known in the art. For instance, when *S. aureus* is recovered from the culture it is sometimes desirable to incubate the cells with lysozyme and lysostaphin enzymes followed by a protease such as Proteinase K, Pronase E or trypsin and salt precipitations. Another method involves recovering the cell-free supernate of the bacterial culture and isolating the PNAG using membranes that retain molecules of different molecular weights. Once concentrated, a solvent such as methanol, ethanol, acetone or other material capable of causing PNAG to become insoluble is added in a sufficient volume to precipitate PNAG. The material is then subjected to the same enzymatic treatments as described above generally. Other methods for harvesting and isolating polysaccharide are known in the art. (See for example Maira et al. Infect. Immun. 2002; 70:4433-4440.)

It is also to be understood that the nucleic acids described herein (i.e., the ica regulatory nucleic acids) may be used in the production of polysaccharides other than PNAG, provided that the appropriate coding sequences are operably linked thereto.

Methods relating to the harvest, isolation and purification of other proteins which are produced according to the invention (e.g., therapeutic proteins and the like) will vary depending upon the protein. Such methods are known to those of ordinary skill in the art.

The polysaccharide produced from the over-producing bacteria has a beta (β) 1-6 linkage (i.e., glucosamine monomer units linked together by beta (β) 1-6 linkages). It can have 0-100% acetate substitutions, and can be as small as 2-3 monomer units, but is preferably 4-6 monomer units in length. The corresponding molecular weights for these polysaccharides are approximately 400, 600, 800, 1000 and 1200 Daltons.

In some aspects, the PNAG antigens have the following structure:

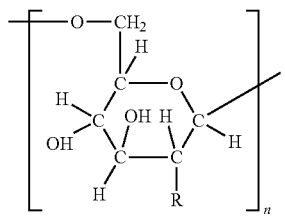

where n is an integer ranging from 2 to greater than or equal to 300, R is selected from the group consisting of —NH—CO—CH₃ and —NH₂. Preferably, less than 50% of the R groups are —NH—CO—CH₃. In some embodiments, the antigen has a molecular weight of at least 800 Daltons.

The size of the PNAG antigens varies greatly. In some aspects, the PNAG antigen is a high molecular weight homopolymer of greater than 100,000 Daltons. Polysaccharides between 500 and 20,000,000 Daltons will be typical. PNAG antigen having smaller molecular weight may be conjugated to carriers when used as therapeutic or diagnostic agents or may be used alone. Preferably, the PNAG has a molecular weight of at least 1,000 Daltons. In other embodiments, PNAG has a molecular weight of at least 2,000 Daltons, at least 5,000 Daltons, at least 10,000 Daltons, at least 30,000 Daltons, or at least 100,000 Daltons.

In some embodiments and preferably when PNAG is used therapeutically, the PNAG antigens are pure PNAG preparations. As used herein, a "pure PNAG preparation" is a PNAG preparation which has been isolated and which is greater than 90% free of contaminants. In some embodiments, the PNAG is greater than 91%, 92%, 93%, 94%, 95%, 96%, 97%, 98%, 99% or is 100% free of contaminants. The degree of purity of the PNAG antigen can be assessed by any means known in the art. For example, the purity can be assessed by chemical analysis assays as well as gas chromatography and nuclear magnetic resonance to verify structural aspects of the material.

The polysaccharides generated according to the methods of the invention are useful in a variety of different applications including in vitro, in situ and in vivo, diagnostics and therapeutics. For instance, these compositions may be used to immunize subjects in vivo to prevent or treat infection. The compositions may also be used to develop antibodies and other binding peptides which are specific for PNAG, and which can be used in the diagnosis and treatment of infectious diseases as well as research applications.

The over-producing bacteria can be used to generate antibodies to the polysaccharide. The antibodies may be monoclonal antibodies or polyclonal antibodies.

Many methods for preparing polyclonal antibodies are known. One example involves the combination of the PNAG antigen (or fragment thereof) or antigen conjugate with an adjuvant such as Freund's complete adjuvant or other adjuvant (e.g., 100 μg of conjugate for rabbits or mice in 3 volumes of Freund's has been found to be useful) and injected intradermally at multiple sites. Approximately one month later, the animals are boosted with 1/5-1/10 of the original amount of antigen or antigen conjugate in adjuvant by subcutaneous injection at multiple sites. One to two weeks later the animals are bled, and the serum is assayed for the presence of antibody. The animals may be repeatedly boosted until the antibody titer plateaus. The animal may be boosted with the PNAG antigen alone, the PNAG antigen conjugate, or PNAG conjugated to a different carrier compound with or without an adjuvant.

In addition to supplying a source of polyclonal antibodies, the immunized animals can be used to generate PNAG antigen specific monoclonal antibodies. As used herein the term "monoclonal antibody" refers to a homogenous population of immunoglobulins which specifically bind to the same epitope (i.e. antigenic determinant) of PNAG. Monoclonal antibodies can be prepared by any method known in the art such as by immortalizing spleen cells isolated from the immunized animal by e.g., fusion with myeloma cells or by Epstein Barr Virus transformation and screening for clones expressing the desired antibody. Other methods involve isolation of polyclonal antibodies and generating monoclonal antibodies using immortalized cell lines. Methods for preparing and using monoclonal antibodies are well known in the art.

Murine anti-PNAG monoclonal antibodies may be made by any of these methods utilizing PNAG as an immunogen. The following description of a method for developing an anti-PNAG monoclonal antibody is exemplary and is provided for illustrative purposes only. Balb/c mice are immunized intraperitoneally with approximately 75-100 μg of purified PNAG in an complete Freund's adjuvant. Booster injections of approximately 25-50 μg PNAG in incomplete Freund's are administered on approximately days 15 and 35 after the initial injection. On day 60-65, the mice receive booster injections of approximately 25 μg PNAG in the absence of adjuvant. Three days later, the mice are killed and the isolated spleen cells fused to murine myeloma NS-1 cells using polyethylene glycol by a procedure such as that described by Oi(Oi VT: Immunoglobulin-producing hybrid cell lines in Herzenberg LA (ed): Selected Methods in Cellular Biology, San Francisco, Calif., Freeman, (1980)). Hybridoma cells are selected using hypoxanthine, aminopterin, and thymidine (HAT) and grown in culture. Fourteen to fifteen days after fusion, hybridoma cells producing anti-PNAG monoclonal antibodies are identified using a solid-phase radioimmunoassay by capturing anti-PNAG antibodies from conditioned media with immobilized goat anti-mouse IgG followed by quantitation of specifically bound $^{125}$I-labeled PNAG. Hybridomas testing positive for antibodies against PNAG are subcloned by limiting dilution and re-tested. Ascites for the hybridomas is then prepared in pristane-primed BALB/c mice by injecting approximately $1 \times 10^6$ cells/mouse. Concentrates enriched in the selected monoclonal antibodies are produced from ascites fluid by gel filtration on S-200 and concentrated with $NH_4SO_4$. The pellets are dissolved in an appropriate storage solution such as 50% glycerol/$H_2O$ and are stored at 4° C.

An "anti-PNAG antibody" as used herein includes humanized antibodies and antibody fragments as well as intact monoclonal and polyclonal antibodies. A "humanized monoclonal antibody" as used herein is a human monoclonal antibody or functionally active fragment thereof having at least human constant regions and a PNAG binding region (e.g., a CDR) from a mammal of a species other than a human.

Human monoclonal antibodies may be made by any of the methods known in the art, such as those disclosed in U.S. Pat. No. 5,567,610, issued to Borrebaeck et al., U.S. Pat. No. 565,354, issued to Ostberg, U.S. Pat. No. 5,571,893, issued to Baker et al, Kozber, *J. Immunol.* 133: 3001 (1984), Brodeur, et al., *Monoclonal Antibody Production Techniques and Applications*, p. 51-63 (Marcel Dekker, Inc, new York, 1987), and Boerner et al., *J. Immunol.*, 147: 86-95 (1991). In addition to the conventional methods for preparing human monoclonal antibodies, such antibodies may also be prepared by immunizing transgenic animals that are capable of producing human antibodies (e.g., Jakobovits et al., *PNAS USA,* 90:2551 (1993), Jakobovits et al., *Nature,* 362: 255-258 (1993), Bruggermann et al., *Year in Immunol.,* 7:33 (1993) and U.S. Pat. No. 5,569,825 issued to Lonberg).

The following examples of methods for preparing humanized monoclonal antibodies that interact with PNAG are exemplary and are provided for illustrative purposes only. Humanized monoclonal antibodies, for example, may be constructed by replacing the non-CDR regions of a non-human mammalian antibody with similar regions of human antibodies while retaining the epitopic specificity of the original antibody. For example, non-human CDRs and optionally some of the framework regions may be covalently joined to human FR and/or Fc/pFc' regions to produce a functional antibody. There are entities in the United States which will synthesize humanized antibodies from specific murine antibody regions commercially, such as Protein Design Labs (Mountain View California), Abgenix (Fremont, Calif.), and Medarex (Princeton N.J.).

European Patent Application 0239400, the entire contents of which is hereby incorporated by reference, provides an exemplary teaching of the production and use of humanized monoclonal antibodies in which at least the CDR portion of a murine (or other non-human mammal) antibody is included in the humanized antibody. Briefly, the following methods are useful for constructing a humanized CDR monoclonal antibody including at least a portion of a mouse CDR. A first replicable expression vector including a suitable promoter operably linked to a DNA sequence encoding at least a variable domain of an Ig heavy or light chain and the variable domain comprising framework regions from a human antibody and a CDR region of a murine antibody is prepared. Optionally a second replicable expression vector is prepared which includes a suitable promoter operably linked to a DNA sequence encoding at least the variable domain of a complementary human Ig light or heavy chain respectively. A cell line is then transformed with the vectors. Preferably the cell line is an immortalized mammalian cell line of lymphoid origin, such as a myeloma, hybridoma, trioma, or quadroma cell line, or is a normal lymphoid cell which has been immortalized by transformation with a virus. The transformed cell line is then cultured under conditions known to those of skill in the art to produce the humanized antibody.

As set forth in European Patent Application 0239400 several techniques are well known in the art for creating the particular antibody domains to be inserted into the replicable vector. (Preferred vectors and recombinant techniques are discussed in greater detail below.) For example, the DNA sequence encoding the domain may be prepared by oligonucleotide synthesis. Alternatively a synthetic gene lacking the CDR regions in which four framework regions are fused together with suitable restriction sites at the junctions, such that double stranded synthetic or restricted subcloned CDR cassettes with sticky ends could be ligated at the junctions of the framework regions. Another method involves the preparation of the DNA sequence encoding the variable CDR containing domain by oligonucleotides site-directed mutagenesis. Each of these methods is well known in the art. Therefore, those skilled in the art may construct humanized antibodies containing a murine or other type of CDR region without destroying the specificity of the antibody for its epitope. See, e.g., L. Riechmann et al., Nature 332, 323 (1988); M. S. Neuberger et al., Nature 314, 268 (1985) and EPA 0 239 400 (published Sep. 30, 1987). Humanized antibodies have particular clinical utility in that they specifically recognize PNAG but will not evoke an immune response in humans against the antibody itself.

Human antibodies may also be obtained by recovering antibody-producing lymphocytes from the blood or other tissues of humans producing antibody to PNAG, e.g., a human vaccinated with the antigens described herein. These lymphocytes can be treated to produce cells that grow on their own in the laboratory under appropriate culture conditions. The cell cultures can be screened for those making antibody to PNAG, such cultures subjected to cloning to achieve cultures starting from a single cell, and the cloned cultures screened again to identify those producing PNAG. Such cultures themselves could be used to produce human monoclonal antibodies to PNAG or the genetic elements encoding the variable portions of the heavy and light chain of the antibody can be cloned and inserted into genetic vectors for production of antibody of different types.

PNAG binding antibody fragments are also encompassed by the invention. As is well-known in the art, only a small portion of an antibody molecule, the paratope, is involved in the binding of the antibody to its epitope (see, in general, Clark, W. R. (1986) The Experimental Foundations of Modern Immunology Wiley & Sons, Inc., New York; Roitt, I. (1991) Essential Immunology, 7th Ed., Blackwell Scientific Publications, Oxford). The pFc' and Fc regions of the antibody, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. An isolated $F(ab')_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', $F(ab')_2$ and Fv are employed with either standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)]. Well-known functionally active antibody fragments include but are not limited to $F(ab')_2$, Fab, Fv and Fd fragments of antibodies. These fragments which lack the Fc fragment of intact antibody, clear more rapidly from the circulation, and may have less non-specific tissue binding than an intact antibody (Wahl et al., J. Nucl. Med. 24:316-325 (1983)). For example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., Nature 341:644-646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevieer, Amsterdam, 1985)), Fv fragments (Hochman et al., Biochemistry 12: 1130 (1973); Sharon et al., Biochemistry 15: 1591 (1976); Ehrlch et al., U.S. Pat. No. 4,355,023) and portions of antibody molecules (Audilore-Hargreaves, U.S. Pat. No. 4,470, 925). Thus, those skilled in the art may construct antibody fragments from various portions of intact antibodies without destroying the specificity of the antibodies for the PNAG epitope.

The antibody fragments also encompass "humanized antibody fragments." As one skilled in the art will recognize, such fragments could be prepared by traditional enzymatic cleavage of intact humanized antibodies. If, however, intact antibodies are not susceptible to such cleavage, because of the nature of the construction involved, the noted constructions can be prepared with immunoglobulin fragments used as the starting materials or, if recombinant techniques are used, the DNA sequences, themselves, can be tailored to encode the desired "fragment" which, when expressed, can be combined in vivo or in vitro, by chemical or biological means, to prepare the final desired intact immunoglobulin fragment. Antibody fragments and other PNAG binding peptides having binding specificity for PNAG and prepared using the PNAG antigen preparations described herein are useful for e.g., diagnostic purposes.

To determine whether a peptide or antibody fragment binds to PNAG any known binding assay may be employed. For example, the peptide may be immobilized on a surface and then contacted with a labeled PNAG. The amount of PNAG which interacts with the peptide or the amount which does not bind to the peptide may then be quantitated to determine whether the peptide binds to PNAG. A surface having an anti-PNAG antibody immobilized thereto may serve as a positive control.

The PNAG of the invention can be used to protect a subject against infection with a bacteria which has a PNAG capsule on its surface by inducing active immunity to infection by Staphylococci in a subject. The method is accomplished by administering to the subject an effective amount for inducing an immune response against Staphylococci of the PNAG described above. This process is also referred to as active immunity.

A "subject" as used herein is a warm-blooded mammal and includes, for instance, humans, primates, horses, cows, swine, goats, sheep, dogs, cats and rodents. In some embodiments, the subject is a non-rodent subject. A non-rodent subject is any subject as defined above, but specifically excluding rodents such as mice, rats and rabbits.

PNAG is administered to the subject in an effective amount for inducing an immune response, such as an antibody response. An "effective amount for inducing an immune response" as used herein is an amount of PNAG which is sufficient to (i) assist the subject in producing its own immune protection by e.g. inducing the production of anti-PNAG antibodies in the subject, inducing the production of memory cells, and possibly a cytotoxic lymphocyte reaction etc. and/ or (ii) prevent infection by Staphylococci from occurring in a subject that is exposed to Staphylococci. An antigen-specific immune response is an immune response which involves immunological memory against a particular antigen.

An effective amount of a PNAG vaccine for stimulating an antibody response as used herein is an amount of PNAG vaccine that is capable of eliciting the production of antibodies that are specific for at least one and preferably at least two species of *Staphylococcus*, e.g., *S. aureus* and *S. epidermidis*.

The anti-PNAG antibodies generated according to the invention are useful for inducing passive immunization in a subject by preventing the development of infection in those subjects at risk of exposure to or having been infected with infectious agents. The method for inducing passive immunity to infection by Staphylococci is performed by administering to a subject an effective amount of an anti-PNAG antibody for inducing opsonization of Staphylococci. "Passive immunity" as used herein involves the administration of antibodies to a subject, wherein the antibodies are produced in a different subject (including subjects of the same and different species), such that the antibodies attach to the surface of the bacteria and cause the bacteria to be phagocytosed.

The anti-PNAG antibody of the invention may be administered to any subject at risk of developing a Staphylococcal infection to induce passive immunity. The anti-PNAG antibody can even be administered to a subject that is incapable of inducing an immune response to an antigen. Although vaccination with a PNAG antigen might not be effective in high risk immunocompromised subjects, these subjects will benefit from treatment with antibody preparations raised against Staphylococci. A subject that is incapable of inducing an immune response is an immunocompromised subject (e.g. patient undergoing chemotherapy, AIDS patient, etc.) or a subject that has not yet developed an immune system (e.g. pre-term neonate). The anti-PNAG antibody may be administered to a subject at risk of developing a Staphylococcal infection to prevent inhibit or slow the infectious agent from multiplying in the body or to kill the infectious agent. The anti-PNAG antibody may also be administered to a subject who already has an infection caused by Staphylococci to prevent, inhibit or slow the infectious agent from multiplying in the body or to kill the infectious agent.

The invention also encompasses isolated ica regulatory nucleic acid molecules. The nucleic acid may comprise (a) nucleic acid molecules which hybridize under stringent conditions to a nucleic acid molecule having a sequence of SEQ ID NO:2, have an addition, deletion or substitution in a region between and including nucleotides 9 and 43 of SEQ ID NO:2, and enhance production of a polysaccharide from an ica locus, and (b) complements thereof. The isolated nucleic acid may comprise SEQ ID NO:1, or it may comprise the nucleotide sequence between and including nucleotides 9 and 38 of SEQ ID NO:1. The isolated nucleic acid may comprise a deletion, addition or substitution in the region between and including nucleotides 24 and 28 of SEQ ID NO:2 (i.e., the 5 nucleotide motif mutated in MN8m). Such deletions, additions or substitutions may be complete or partial.

The invention also provides an isolated nucleic acid molecule selected from the group consisting of (a) a fragment of a nucleic acid molecule having a sequence of SEQ ID NO:1, and (b) complements of (a). Such fragments span a MN8m mutation and enhance production of a polysaccharide from an ica locus when operably linked to an ica nucleic acid. As used herein, an "MN8m mutation" refers to the five nucleotide deletion found in strain MN8m. In other embodiments, the nucleic acid molecule is a fragment of an ica promoter region from strain MN8m. The fragment may have a length of at least 10, at least 20, at least 30, at least 40, at least 50, at least 60, at least 70, at least 80, at least 90, at least 100, at least 110, at least 120, at least 130, at least 140, at least 150, or at least 160 nucleotides in length. The sequences flanking the MN8m mutation need not be equidistant (i.e., the MN8m mutation need not be centered in the fragment). In one embodiment, the fragment has a nucleotide sequence between and including nucleotides 9 and 38 of SEQ ID NO:1.

The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers to hybridization at 65° C. in hybridization buffer (3.5×SSC, 0.02% Ficoll, 0.02% Polyvinyl pyrolidone, 0.02% Bovine Serum Albumin, 25mM $NaH_2PO_4$ (pH7), 0.5% SDS, 2mM EDTA). SSC is 0.15 M Sodium Chloride/0.015 M Sodium Citrate, pH 7; SDS is Sodium Dodecyl Sulphate; and EDTA is Ethylene diaminetetraacetic acid. After hybridization, the membrane upon which the DNA is transferred is washed at 2×SSC at room temperature and then at 0.1-0.5×SSC/0.1× SDS at temperatures up to 68° C. Alternatively, stringent hybridization may be performed using a commercially available hybridization buffer, such as ExpressHyb™ buffer (Clontech) using hybridization and washing conditions described by the manufacturer.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of variants of the ica regulatory nucleic acids.

In screening for variant nucleic acids, a nucleic acid hybridization such as a Southern blot or a Northern blot may be performed using the foregoing conditions, together with a detectably labeled probe (e.g., radioactive such as $^{32}P$, chemiluminescent, fluorescent labels). After washing the membrane to which DNA was finally transferred, the membrane can be placed against X-ray film, phosphoimager or other detection device to detect the detectable label.

The compositions described herein may be isolated compositions. As used herein, the term "isolated" refers to a composition which is separated from the natural environment in which it is normally found. For instance an "isolated nucleic acid" is one which is (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated composition may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein encompasses a non-naturally occurring chromosome as well as total genomic DNA isolated from cells and tissues.

A nucleic acid that enhances production of a polysaccharide from an ica locus is a nucleic acid sequence which when inserted into an expression vector including an ica gene and/or a reporter gene causes an increase in expression in comparison to a wild type ica promoter region. For instance when the nucleic acid of SEQ ID NO:1 is inserted into an expression vector and is operably linked to an ica gene in the vector, it results in an increase in expression of the ica gene product over that of the nucleic acid of SEQ ID NO:2 inserted into the same vector. The skilled artisan is familiar with the methodology for screening cells and libraries for expression of molecules from such expression vectors which then are routinely isolated, followed by isolation of the pertinent nucleic acid molecule and sequencing.

Thus the invention also includes expression vectors comprising the isolated ica regulatory nucleic acid, operably linked to an ica gene or nucleic acid or a fragment thereof and/or a reporter gene or other coding sequence (e.g., that of a therapeutic protein). As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate autonomously or after integration into the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of the expression vector.

The invention also embraces so-called expression kits, which allow the artisan to prepare a desired expression vector or vectors. Such expression kits include at least separate portions of at least two of the previously discussed materials. Other components may be added, as desired.

The vector may optionally include another gene expression sequence which contributes to the expression of the gene with a host cell. A "gene expression sequence" is any regulatory nucleotide sequence, such as a promoter sequence or promoter-enhancer combination, which facilitates the efficient transcription and translation of a nucleic acid to which it is operably linked. The gene expression sequence may, for example, be a mammalian or viral promoter, such as a constitutive or inducible promoter. Constitutive mammalian promoters include, but are not limited to, the promoters for the following genes: hypoxanthine phosphoribosyl transferase (HPTR), adenosine deaminase, pyruvate kinase, and β-actin. Exemplary viral promoters which function constitutively in cells include, for example, promoters from the simian virus, papilloma virus, adenovirus, human immunodeficiency virus (HIV), Rous sarcoma virus, cytomegalovirus, the long terminal repeats (LTR) of moloney leukemia virus and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

The ica nucleic acid and the ica regulatory nucleic acid are said to be "operably linked" when they are covalently linked in such a way as to place the transcription and/or translation of the ica gene coding sequence under the influence or control of the ica regulatory nucleic acid. If it is desired that the ica sequence be translated into functional protein(s), two DNA sequences are said to be operably linked if induction of a promoter in the 5' gene expression sequence results in the transcription of the ica sequence and if the nature of the linkage between the two DNA sequences does not (1) result in the introduction of a frame-shift mutation, (2) interfere with the ability of the promoter region to direct the transcription of the ica sequence, or (3) interfere with the ability of the corresponding RNA transcript to be translated into a protein. Thus, a ica gene would be operably linked to a ica regulatory nucleic acid if the ica regulatory nucleic acid were capable of effecting transcription of that ica gene such that the resulting transcript might be translated into the desired protein or polypeptide.

The expression vector is transfected, transduced or transformed into a host cell. The cell can be a eukaryotic or prokaryotic cell but preferably is a bacterial cell. More preferably the cell is a Staphylococcal bacterium, which may or may not ordinarily express PNAG.

The invention also encompasses methods for identifying an isolated binding agents that bind selectively or with differential affinities either to SEQ ID NO:1 or SEQ ID NO:2. The method involves contacting a first nucleic acid molecule having the sequence of SEQ ID NO:2 or a functionally equivalent fragment thereof with a candidate molecule and determining whether the candidate molecule binds to the first nucleic acid molecule, and contacting a second nucleic acid molecule having the sequence of SEQ ID NO:1 or a functionally equivalent fragment thereof with the candidate molecule and determining whether the candidate molecule binds to the second nucleic acid molecule. A candidate molecule that binds to either the first or the second nucleic acid molecule but not both is indicative of a binding agent. Alternatively, a candidate molecule that binds to the sequences with differential affinities is also indicative of a suitable binding agent. For example, the binding agent may bind with higher affinity to SEQ ID NO:1 than to SEQ ID NO:2, or alternatively, it may bind with higher affinity to SEQ ID NO:2 than to SEQ ID NO:1.

As used herein, a functionally equivalent fragment of SEQ ID NO:2 is any fragment of SEQ ID NO:2 that can be used in a comparison with SEQ ID NO:1, and preferably a fragment that comprises the five nucleotide sequence that is deleted in MN8m. As used herein, a functionally equivalent fragment of SEQ ID NO:1 is a fragment that comprises the MN8m mutation.

The candidate molecule can be further screened for its ability to modulate transcription from the ica locus. Binding agents that modulate transcription from the ica locus are referred to as ica regulatory binding agents, and may be polysaccharide synthesis modulators. Transcription assays may involve the use of reporter constructs.

The candidate molecules can be nucleic acid or peptide in nature, but they are not so limited. They may be derived from naturally occurring (e.g., a bacterial lysate) or synthetic (e.g., a recombinant library) sources. The candidate molecule may be a small molecule, and may be derived from a small molecule library (i.e., it is then a library member). The candidate molecule is conjugated to a detectable label. The detectable label may be selected from the group consisting of a radioactive label, an enzyme, a biotin molecule, an avidin molecule or a fluorochrome, but it is not so limited. The candidate molecule may also be conjugated to a cytotoxic agent.

The invention further provides compositions comprising the aforementioned binding agents. In one aspect, the invention provides a composition comprising an isolated binding agent that binds with greater affinity to a nucleic acid having a sequence of SEQ ID NO:1 than to SEQ ID NO:2. In another aspect, the invention provides a composition comprising an isolated binding agent that binds with greater affinity to a nucleic acid having a sequence of SEQ ID NO:2 than to SEQ ID NO:1.

The isolated binding agents may be identified using methods known in the art for assessing binding. An example of a DNA affinity chromatography method is provided in the Examples.

Binding agents may be rationally designed based on known nucleic acid molecular interactions or may simply be identified by conventional screening methods, such as phage display procedures (e.g. methods described in Hart et al., *J. Biol. Chem.* 269:12468 (1994)) or screening of libraries such as combinatorial libraries. Many types of combinatorial libraries have been described. For instance, U.S. Pat. No. 5,712,171 (which describes methods for constructing arrays of synthetic molecular constructs by forming a plurality of molecular constructs having the scaffold backbone of the chemical molecule and modifying at least one location on the molecule in a logically-ordered array); U.S. Pat. No. 5,962,412 (which describes methods for making polymers having specific physiochemical properties); and U.S. Pat. No. 5,962,736 (which describes specific arrayed compounds).

The isolated binding agent may be conjugated to compounds such as a detectable label or a cytotoxic agent. The label used can be any detectable functionality that does not interfere with the binding of analyte and its binding partner. Numerous labels are known for such use in immunoassays. For example, compounds that may be detected directly, such as fluorochrome, chemiluminescent, and radioactive labels, as well as compounds that can be detected through reaction or derivitization, such as enzymes. Examples of these types of labels include $^{32}P$, $^{14}C$, 125I, $^{3}H$, and $^{131}I$ radioisotopes, fluorophores such as rare earth chelates or fluorescein and its derivatives, rhodamine and its derivatives, dansyl, umbelliferone, luciferases, such as firefly luciferase and bacterial luciferase (U.S. Pat. No. 4,737,456), luciferin, 2,3-dihydrophthalavinediones, horseradish peroxidase (HRP), alkaline phosphatase, ⊖-galactosidase, glucoamylase, lysozyme, saccharide oxidases such as glucose oxidase, galactose oxidase, and glucose-6-phosphate dehydrogenase. Heterocyclic oxidases such as uricase and xanthine oxidase, coupled to an enzyme that uses hydrogen peroxide to oxidize a dye precursor such as HRP, lactoperoxidase, or microperoxidase, biotin avidin, spin labels, bacteriophage labels, and stable free radicals.

Compositions of the invention may be delivered in conjunction with another anti-bacterial drug or in the form of anti-bacterial cocktails or with other bacterial antigens or antibodies. An anti-bacterial cocktail is a mixture of agents useful in inhibiting or eliminating a bacterial infection. The use of antibiotics in the treatment of bacterial infection is routine. The use of antigens for inducing active immunization and antibodies to induce passive immunization is also routine. In this embodiment, a common administration vehicle (e.g., tablet, implant, injectable solution, etc.) could contain both the composition useful in this invention and the antibacterial drug and/or antigen/antibody. Alternatively, the anti-bacterial drug and/or antigen/antibody can be separately dosed.

Antibiotic drugs are well known and include: penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefmenoxine, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin. (See Goodman and Gilman's, Pharmacological Basics of Therapeutics, 8th Ed., 1993, McGraw Hill Inc.)

The invention further provides various diagnostic and screening methods. One such method is a method of identifying an ica promoter sequence associated with polysaccharide over-production. The method involves detecting a nucleic acid molecule having a sequence alteration from wildtype in a region between and including nucleotides 9 and 43 of SEQ ID NO:2. The sequence alteration may be an addition, a deletion or a substitution, or a combination thereof. There are various ways of detecting such sequence alterations, and those of ordinary skill in the art will be familiar with such methods. Some representative examples are provided here briefly. These detection methods may involve differential binding of probes such as nucleic acid probes, or antibodies, for example. The nucleic acid probes may bind to the MN8m mutation region directly, or alternatively they may bind sequences flanking the mutation. Readouts of such assays include presence or absence of binding of a probe, differential length of nucleic acids to which the probe binds, presence or absence of a PCR product, and differential length of PCR products.

In some PCR based methods, PCR primers may be used which fail to bind to either SEQ ID NO:1 or SEQ ID NO:2. In this way, a PCR product is only possible in the presence of one of these sequences but not the other. In other PCR based methods, the primers may bind to a target nucleic acid upstream and downstream of the MN8m mutation region. The length of the PCR product generated from a test nucleic acid (or sample containing the nucleic acid) is then compared to the length of PCR products from SEQ ID NO:1 and/or SEQ ID NO:2. A PCR product that is identical in length to a product amplified from SEQ ID NO:1 and/or shorter in length to a product amplified form SEQ ID NO:2 is indicative of a nucleic acid having an ica promoter sequence associated with polysaccharide over-production.

In non-PCR based methods, probes can be used that bind either selectively or with greater affinity to SEQ ID NO:1 relative to binding to SEQ ID NO:2.

The nucleic acids being analyzed can be derived from a bacterial isolate from a subject. Alternatively, they can derive from laboratory strains recombinantly or naturally altered.

The invention further provides a method for identifying an ica regulatory nucleic acid molecule that enhances polysaccharide production. The method involves altering a nucleic acid molecule having a sequence of SEQ ID NO:2, and determining a level of reporter production by a bacterium that comprises the altered nucleic acid molecule operably linked to reporter nucleic acid. A level of reporter protein production that exceeds wildtype is indicative of an ica regulatory nucleic acid molecule that enhances polysaccharide production. The reporter nucleic acid may be an ica nucleic acid and reporter production is polysaccharide production. The nucleic acid molecule may be altered recombinantly or it may be altered naturally during bacterial culture.

The following examples are included for purposes of illustration and are not intended to limit the scope of the invention.

EXAMPLES

Example 1

Materials and Methods

Staphylococcal strains: S. aureus strain MN8 is a clinical isolate obtained originally from Patrick Schlievert, Minneapolis, Minn. Strain MN8m was a spontaneous mutant isolated from a chemostat culture of strain MN8 (McKenney et al., 1999). Strain NCTC 10833 (ATCC 25904) is a clumping factor positive variant of a throat swab isolate. Partial deletion of the ica locus to produce strains 10833Δica::tet and MN8Δica::tet was performed as described (Cramton et al., 1999, Cramton et al, 2001a).

Plasmids, primers, and cloning and expression of genes in the ica locus: All plasmid purifications were performed with the QIAprep spin miniprep kit (Qiagen, Valencia, Calif.). All primers were custom synthesized by Qiagen Operon (Alameda, Calif.). Restriction enzymes and DNA modifying enzymes were purchased from New England Biolabs (Beverly, Mass.). The expression plasmid pCRT7-NT (Invitrogen) was used to clone the icaR gene and express recombinant IcaR protein. The gene was amplified using the primer pair icaRF: TTT CTT CAA AAA TAT ATT TAG TAG CGA ATA CAC (SEQ ID NO:5) and icaRR: AAG GAT AAG ATT ATT GAT AAC GCA ATA AC (SEQ ID NO:6). The icaR gene was cloned into the vector and expressed in E. coli BL21pLysS cells according to manufacturer's instructions. The pCRT7-NT vector adds a tag of 6 histidine residues to the amino-terminus of the protein. The IcaR protein and the vector expression control were purified using Probond nickel affinity chromatography resin (Invitrogen). Plasmid pBT9 is a temperature-sensitive plasmid derived from pBT2 which lacks the EcoRI restriction site (Bruckner, 1997). All plasmid constructs were initially transformed into the restriction-deficient S. aureus strain RN4220 according to the method of Lee (Lee, 1993). Constructs were transferred to other strains of S. aureus by transduction using phage 80 (Kasatiya and Baldwin, 1967; Novick, 1967). The ica loci from different strains were amplified by PCR using previously described primers SA11 and SA12 (Cramton et al., 1999) and the Elongase kit (Invitrogen, Carlsbad, Calif.). PCR products were gel purified using Ultrafree DA spin columns (Millipore, Bedford, Mass.), digested with KpnI and ligated into the KpnI site of pBT9. PCR-based site-directed deletion mutagenesis was performed using the following primer pair: DelFwd: CCG TTT AAT TAT AAC AAC AAT CTA TTG C (SEQ ID NO:7) and DelRev: TTT GTA ATT GCA ACT TAA TTT TCC TGT AAC (SEQ ID NO:8). PCR-based substitution mutagenesis was performed using the following primer pair: DelRev+SubFwd ATA AAC CGT TTA ATT ATA ACA ACA ATC TAA TTG C (SEQ ID NO:9). PCR was performed using the Elongase kit, template DNA was digested with DpnI for 30 min at 37° C., DNA ends were phosphorylated with T4 kinase, and the PCR products were blunt-end ligated. All mutations were confirmed by DNA sequencing which was carried out by the Microbiology Core Facility at Harvard Medical School (Boston, Mass.).

Biofilm assay: Microtiter plate assays for biofilm production were performed essentially as described by Christensen with minor modifications (Christensen et al., 1985). Cultures were grown overnight in 10 ml of tryptic soy broth (TSB)+1% glucose, diluted 1:200 in TSB+glucose, and aliquoted into 96-well polystyrene flat bottom microtiter plates from Corning (Corning, N.Y.). After 24 hr at 30° C. (the permissive temperature for the pBT9 vector that was present in strains used in the biofilm assays) the wells were emptied and washed twice with phosphate buffered saline (PBS). The plates were dried at ambient temperature, stained for 30 sec with safranin, washed under gently running tap water and scanned using a digital scanner.

RNA Slot-Blot Analysis: S. aureus cultures were grown in TSB+1% glucose at 37° C. for 16 hr. RNA was extracted from $10^9$ cells using the Rneasy miniprep kit (Qiagen) as described in the manufacturer's instructions except that 0.5 mg/ml lysostaphin was used in place of lysozyme to lyse the cells. RNA samples were treated with DNase, RNA concentrations were determined by absorbance at 260 nm and 4 mg of each sample was immobilized on a nylon membrane. The single icaA, icaD, icaB, and icaC transcript was detected by hybridization analysis essentially as described by Cramton et al. (Cramton et al, 2001b) except that the DNA probe was labeled using the ECL direct nucleic acid labeling and detection system (Amersham).

Preparation of S. aureus lysates for gel electrophoretic mobility shift assays. Five hundred milliliters of TSB were inoculated with 5 ml of an overnight culture of S. aureus MN8. Cultures were well aerated and grown at 37° C. for 5 hr (OD600=0.9). Cells were lysed essentially as described by Fournier (Fournier et al, 2000); they were first washed in 25 ml buffer A (20 mM Tris-HCl, 50 mM MgCl$_2$, 1 mM dithiothreitol (DTT), 0.1 mM EDTA, 5% glycerol), frozen for 2 hr at −80° C., and lysed in 5 ml buffer A containing 100 mg/ml lysostaphin and EDTA-free Complete Protease Inhibitors (Boehringer Mannheim) for 3.5 hr on ice. Three ml buffer A+1.3 M KCl was added and the incubation was continued on ice for 30 min. Lysates were cleared by centrifugation, filter-sterilized, and dialyzed through a 3,500 MWCO membrane (Pierce, Rockford, Ill.) overnight against 4 L 10 mM HEPES+1 mM MgCl$_2$+0.5 mM DTT at 4° C.

Oligonucleotide probes for electrophoretic mobility shift assay: Double-stranded oligonucleotides were generated by combining a primer with its reverse complement (10 pM each) in 50 mM Tris-HCl+50 mM NaCl, warming the reaction to 80° C., and allowing it to cool at 1° C./min to 25° C. The following three primers were used: WTshort: CTA TGT TAC AGG AAA ATT AAG TTG CAA TTA CAA ATA TTT CCG TTT AAT TAT AA (SEQ ID NO:10); SUB: CTA TGT TAC AGG AAA ATT AAG TTG CAA TTA CAA AAT AAA CCG TTT AAT TAT AA (SEQ ID NO:11); and MUC: CTA TGT TAC AGG AAA ATT AAG TTG CAA TTA CAA ACC GTT TAA TTA TAA (SEQ ID NO:12). A 198 bp probe was generated by PCR using genomic DNA as a template obtained from either S. aureus MN8 to yield the WT probe or S. aureus MN8m to yield the MUC probe using the following primer pair: icaFWD: 5'-ATT GCG TTA TCA ATA ATC TTA TCC TTC -3' (SEQ ID NO:13) and icaREV: 5'-TTG CAA TTT CTT TAC CTA CCT TTC -3' (SEQ ID NO:14). The PCR product was purified using the Qiagen PCR purification kit. For gel shift analysis the double-stranded probes were labeled with [γ-32P]ATP using T4 kinase.

The 198 bp (wildtype) probe used in the gel shift has the sequence of ATT GCG TTA TCA ATA ATC TTA TCC TTC AAT TTT TAT AAC CCC CTA CTG AAA ATT AAT CAC ACT ATG TTA CAG GAA AAT TAA GTT GCA ATT ACA AAT ATT TCC GTT TAA TTA TAA CAA CAA TCT ATT GCA AAT TAA AAT ACT ATC AAT TAC CAT ATG GCT TAC AAC CTA ACT AAC GAA AGG TAG GTA AAG AAA TTG CAA (SEQ ID NO:15). The 193 bp (mutant) probe used in the gel shift has the sequence of ATT GCG TTA TCA ATA ATC TTA TCC TTC AAT TTT TAT AAC CCC CTA CTG AAA ATT AAT CAC ACT ATG TTA CAG GAA AAT TAA GTT GCA ATT ACA AAC CGT TTA ATT ATA ACA ACA ATC TAT TGC AAA TTA AAA TAC TAT CAA TTA CCA TAT GGC TTA CAA CCT AAC TAA CGA AAG GTA GGT AAA GAA ATT GCA A (SEQ ID NO:16).

The 53 bp (wildtype) probe used for DNA affinity chromatography (i.e., used to isolate transcription factors that bind to the ica promoter) has the sequence CTA TGT TAC AGG AAA ATT AAG TTG CAA TTA CAA ATA TTT CCG TTT AAT TAT AA (SEQ ID NO:17). The 48 bp (mutant) probe used for DNA affinity chromatography (i.e., used to isolate transcription factors that bind to the ica promoter) has the sequence CTA TGT TAC AGG AAA ATT AAG TTG CAA TTA CAA ACC GTT TAA TTA TAA (SEQ ID NO:18). These latter probes were used to show the existence of a DNA binding protein having differential binding affinity for the mutated sequence.

Electrophoretic mobility shift: Gel shift assays were performed essentially as described by Fournier (Fournier et al., 2000). A 20 ml binding reaction containing 10 mg protein from the cell-free lysate, or 1 mg of purified recombinant IcaR, 1 mg sonicated salmon sperm DNA and 1 mg poly dI-dC in binding buffer (10 mM HEPES, 60 mM KCl, 4 mM MgCl$_2$, 0.1 mM EDTA, 0.1 mg/ml BSA, and 0.25 mM DTT) was incubated on ice for 10 min before adding 1 ml (20,000 cpm) radiolabeled probe. The reaction was incubated for an additional 15 min on ice and loaded onto a 5 % non-denaturing polyacrylamide gel and electrophoresed in 1×Tris/borate/EDTA (TBE) at 125V for 1.5 hours. Gels were dried and exposed to radiographic film overnight at −80° C.

Preparation of S. aureus lysate for DNA affinity chromatography. 5 liters of TSB was inoculated with 50 ml of an overnight culture of MN8. Cultures were well aerated and grown at 37° C. for 5 hr (OD600=0.9). Cells were washed in phospate buffered saline (PBS) and frozen at −80° C. overnight. The cells were thawed and lysed in 15 ml buffer A (20 mM Tris-HCl, 50 mM MgCl$_2$, 1 mM dithiothreitol (DTT), 0.1 mM EDTA, 5% glycerol) containing EDTA-free Complete protease inhibitors (Boehringer Mannheim) and 100 micrograms/ml lysostaphin on ice for 3 hours. 9 ml buffer A+1.3 M KCl was added and the incubation was continued on ice for 30 min. Proteins were precipitated in 50% ammonium sulfate for 1 hr. at 4° C. and removed from solution by centrifugation (14,000 rpm for 30 min). The proteins were resuspended in 2 ml PBS and dialyzed overnight (3,500 MWCO membrane) against 4 L HEPES at 4° C.

DNA affinity chromatography: 2 nmol double stranded probe (CTA TGT TAC AGG AAA ATT AAG TTG CAA TTA CAA ATA TTT CCG TTT AAT TAT AA (SEQ ID NO:17)) was immobilized on 10 mg of Dynabeads (Dynal) according to manufacturer's instructions. The beads were equilibrated with binding buffer (10 mM HEPES, 60 mM KCl, 4 mM MgCl$_2$, 0.1 mM EDTA, 0.1 mg/ml BSA, and 0.25 mM DTT). The cell-free lysate from 5L culture of MN8 was combined with 6 mL binding buffer and 1.5 mg sonicated salmon sperm DNA (SSS) and chilled on ice for 10 min. The lysate mixture was added to the beads and incubated on ice for 10 min. The beads were washed once with BB+200mg/ml sonicated and twice with BB without BSA or SSS. DNA-binding proteins were eluted with 1 ml 10 mM HEPES+0.25 M KCl. The eluate was concentrated and desalted using Microcon YM-3.5 centrifugal concentrators (Millipore). The concentrated sample was subjected to SDS PAGE using Nu-PAGE 4-15% gradient gels and MOPS buffer (Invitrogen). The SDS PAGE gel was stained with Coomassie blue and protein bands were excised with a razor blade and sequenced by mass spectral analysis.

Results

The phenotype of a PNAG-hyperproducing strain is due to changes within the ica locus. The initial hypothesis of this study was that PNAG-overproduction by S. aureus strain MN8m was due to a mutation within the ica locus itself and that the phenotype could be transferred to other strains by a plasmid-born copy of the MN8m ica locus. To test this, the entire ica locus from S. aureus MN8 or S. aureus MN8m was cloned into the temperature-sensitive plasmid pBT9 to create pWT (from strain MN8) and pMUC (from strain MN8m). The plasmids were electroporated into S. aureus RN4220 then transduced using phage 80 into two S. aureus strains in which the chromosomal copy of icaADBC was replaced with a tetracycline resistance cassette (Cramton et al., 1999). The pWT construct restored the wild type biofilm phenotype (i.e., a modest biofilm was produced but only in the presence of 1% glucose in the growth medium) (FIG. 1). The pMUC construct conferred the PNAG over-producing phenotype to both of the S. aureus ica knockout strains (FIG. 1). Strains 10833Dica::tet/pMUC and MN8Dica::tet/pMUC elaborated a thick biofilm with macroscopic aggregates of bacterial cells visible on the plastic wells. These results supported the hypothesis that the mucoid phenotype of MN8m results from mutations within the ica locus itself.

Figure 3:
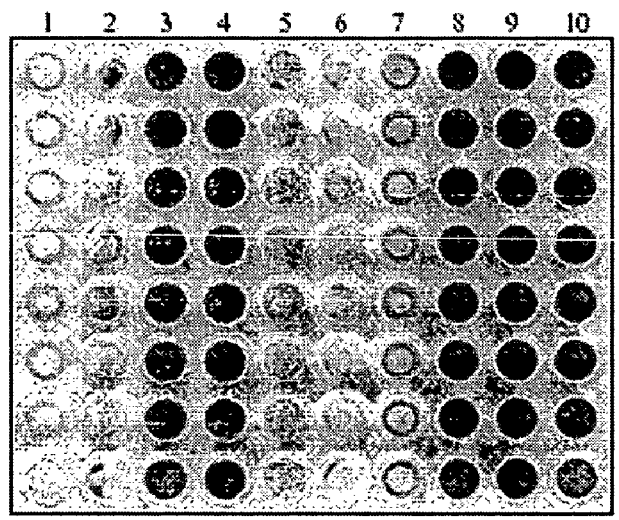
FIG. 3 shows the effect on biofilm production following deletion or substitution of a 5-bp motif in the ica promoter is sufficient to induce the strong biofilm-producing phenotype in S. aureus. Site-directed mutagenesis was performed on the pWT plasmid containing the ica locus from S. aureus MN8 to either delete (pDEL) or substitute (pSUB) the 5-bp TATTT motif within the ica promoter. The microtiter assay was then used to measure biofilm formation. The Staphylococcal strains and the plasmids each carries are as follows: Lane 1: MN8Dica::tet; Lane 2: MN8Dica::tet/pWT; Lane 3: MN8Dica::tet/pMUC; Lane 4: MN8Dica::tet/pDEL; Lane 5: MN8Dica::tet/pSUB; Lane 6: 10833Dica::tet; Lane 7: 10833Dica::tet/pWT; Lane 8: 10833Dica::tet/pMUC; Lane 9: 10833Dica::tet/pDEL; Lane 10: 10833Dica::tet/pSUB. The experiment was repeated 3 times with similar results.

A 5-nucleotide deletion in the ica promoter region augments transcription of the ica locus and induces constitutive hyperproduction of PNAG. A sequence analysis was performed to search for mutations within the ica locus of *S. aureus* strain MN8m which could be responsible for the PNAG hyper-producing phenotype. A 5 bp deletion was found within the promoter region of the ica locus from strain MN8m when compared with the same sequence from strain MN8 (FIG. 2). Site-directed mutagenesis was then used to delete the 5 bp motif in the plasmid pWT to create plasmid pDEL. As FIG. 3 shows, pDEL induced heavy biofilm and cell cluster formation in *S. aureus* strains 10833Dica::tet/pDEL and MN8Dica::tet/pDEL indicating that the 5 bp deletion was sufficient to induce the constitutive PNAG-overproducing phenotype.

Figure 4:
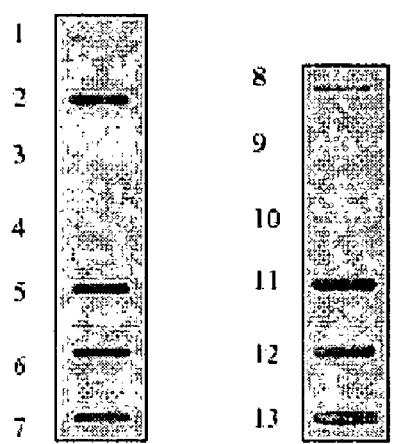
FIG. 4 shows a Northern slot-blot analysis of ica transcript levels in S. aureus strains carrying either the wild type (pWT) allele, the PNAG over-producing allele from strain MN8m lacking a 5-bp TATTT (SEQ ID NO:4) motif (pMUC), or the constructed alleles with a 5-bp deletion (pDEL) or substitution (pSUB) of the TATTT motif in the ica promoter. Slot-blot Northern analysis was performed to semi-quantitatively analyze the level of ica transcription in the recombinant staphylococcal strains. The Staphylococcal strains and the plasmids each carries areas follows: Lane 1: MN8; Lane 2: MN8m; Lane 3: MN8Dica::tet; Lane 4: MN8Dica::tet/pWT; Lane 5: MN8Dica::tet/pMUC; Lane 6: MN8Dica::tet/pDEL; Lane 7: MN8Dica::tet/pSUB; Lane 8: 10833; Lane 9: 10833Dica:: tet; Lane 10: 10833Dica::tet/pWT; Lane 11: 10833Dica::tet/ pMUC; Lane 12: 10833Dica::tet/pDEL; Lane 13: 10833Dica::tet/pSUB.

In order to determine whether the loss of the exact sequence or the change in length of DNA was responsible for the over-producing phenotype, site-directed mutagenesis was used to substitute the original sequence, TATTT (SEQ ID NO:4), with 5 complementary bases, ATAAA, within the ica promoter region of plasmid pWT to create plasmid pSUB. The substitution mutant plasmid, pSUB, also induced strong biofilm formation and cell cluster formation in 10833Dica::tet/pSUB and MN8Dica::tet/pSUB, although it was noted that the biofilm formed by MN8Dica::tet/pSUB was not as thick as the biofilm formed by MN8Dica::tet/pMUC or MN8Dica::tet/pDEL (FIG. 3). To confirm that the increase in biofilm elaboration in the recombinant *S. aureus* strains was due to an increase in transcription of the ica locus, Northern slot-blot analysis was performed. The pWT plasmid restored wild type levels of ica transcription to *S. aureus* strains MN8Dica and 10833Dica::tet whereas the pMUC, pDEL, and pSUB constructs induced levels of ica expression in the ica knock-out strains comparable to that detected in strain MN8m (FIG. 4). Together these results indicate that this particular TATTT motif within the ica promoter region plays a critical role in regulating ica transcription and subsequent biofilm-production.

Figure 5:
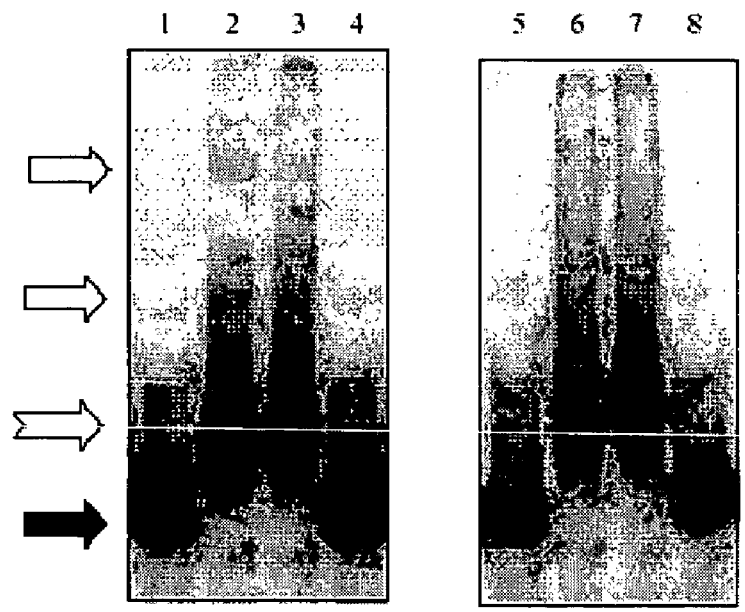
FIG. 5 shows an electrophoretic mobility shift assay to identify DNA-binding proteins in S. aureus MN8 cell-free lysates that bind to the ica promoter. Electrophoretic mobility shift assay shows that a protein(s) from cell-free MN8 lysate induces a shift in a radiolabeled 198-bp stretch of DNA from the ica promoter region. Lanes 1-4 show mobility shift analysis of WT, the probe from the wild type strain MN8 ica promoter whereas lanes 5-8 contain MUC, the probe from the PNAG-over-producing strain MN8m ica promoter. The following components were added to the labeled probe: Lane 1: nothing (free WT probe only); Lane 2: lysate from strain MN8; Lane 3: lysate from strain MN8+100-fold excess of nonspecific unlabeled competitor DNA; Lane 4: lysate from strain MN8+100-fold excess of specific competitor DNA; Lane 5: nothing (free probe from strain MN8m ica promoter); Lane 6: lysate from strain MN8; Lane 7: lysate from strain MN8+100-fold excess of nonspecific unlabeled competitor DNA; Lane 8: lysate from strain MN8+100-fold excess of specific competitor DNA. The solid arrow indicates free probe. The three open arrows point to three distinct shifts induced in the WT probe. The two upper shifts do not occur upon analysis of the MUC probe; only the lower shift, indicated by a notched open arrow, can be seen.
Figure 6:
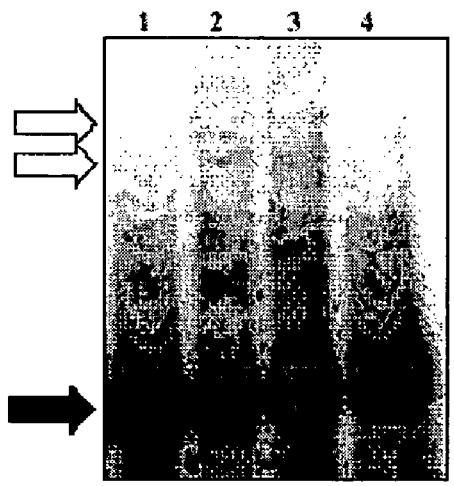
FIG. 6 shows a 53-bp oligonucleotide from the wild type ica promoter sequence undergoes mobility shift in the presence of a cell-free lysate from S. aureus. Wtshort, a radiolabeled 53-bp oligonucleotide probe from the wild type ica promoter was incubated in the absence or presence of cell-free extract from S. aureus strain MN8 with and without competitor DNA. All lanes contained the labeled probe. Added to the probe: Lane 1: nothing (free probe only); Lane 2: lysate from strain MN8; Lane 3: lysate from strain MN8+ 100-fold excess of unlabeled nonspecific competitor oligonucleotide; Lane 4: lysate from strain MN8+100-fold excess of unlabeled specific competitor oligonucleotide. The solid arrow points to free probe and the open arrows point to two specific mobility shifts.

Cell-free lysate from *S. aureus* induces shifts in the electrophoretic mobility of an oligonucleotide containing the TATTT motif. The results from the genetic analysis lead to the hypothesis that the 5 bp motif occurred within the binding site for a repressor of ica transcription. The promoter for the entire ica locus is believed to be located within the 164 bp region between the divergently-transcribed start codons of icaR and icaA. A 198 bp stretch of DNA containing the promoter plus the first few nucleotides of the icaR and icaA genes was generated from *S. aureus* strains MN8 or MN8m total DNA by PCR, radiolabeled, and combined with cell free lysate from *S. aureus* strain MN8 for gel shift analysis. Reproducible mobility shifts occurred with the WT probe (FIG. 5), and two prominent bands were consistently noted in the presence of MN8 cell-free lysates. FIG. 5 also shows that a non-labeled specific competitor competes for binding to the protein causing the mobility shift (lane 4) whereas a nonspecific competitor has no effect on the mobility shift of the target DNA sequence (lane 3). When analyzed for the ability to bind to a probe containing the 5 bp deletion in the *S. aureus* strain MN8m locus, it was found that the lower band was also detected by gel shift analysis with the MUC probe whereas the upper band could not be detected, even after prolonged exposure of the film (FIG. 5). A series of oligonucleotides was designed to identify the shortest sequence containing the 5 bp motif that was shifted by factors within the lysate of strain MN8. A 53 bp probe, WTshort, was the shortest oligonucleotide containing the 5 bp sequence to be shifted by the lysate from *S. aureus* strain MN8 (FIG. 6). The lysate caused two distinct shifts in the Wtshort probe which were competitively inhibited by unlabeled Wtshort but not by an unlabeled non-specific probe.

Figure 7:
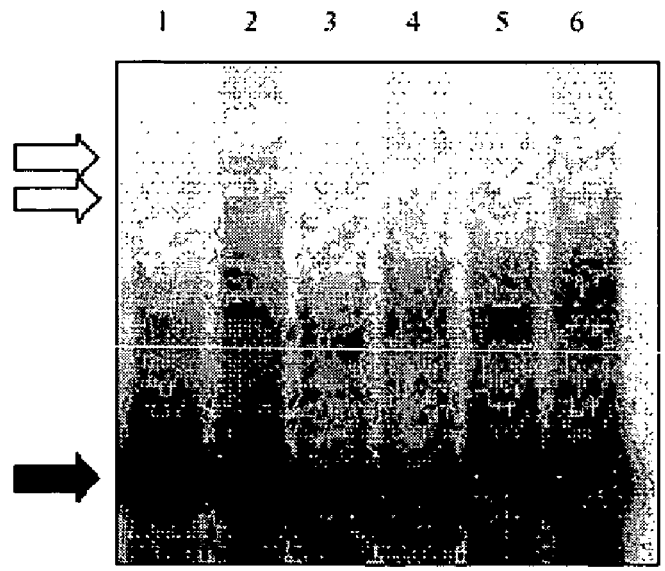
FIG. 7 shows that deleting or substituting a 5-bp TATTT motif within the promoter region of the ica locus abrogates mobility shift with cell-free lysates. Radiolabeled oligonucleotides representative of a 53-bp region of the ica promoter from wild type S. aureus(WTshort), a 48-bp sequence of the ica promoter from PNAG-overproducing S. aureusMN8m (DEL), or a 53-bp sequence wherein the wild type TATTT motif was changed to ATAAA (SUB) were used in gel shift assays to measure binding of proteins within a cell-free lysate of S. aureus strain MN8. The free probe is denoted by a solid arrow and the mobility shifts are denoted by open arrows. Lane 1: WTshort probe only (no lysate); Lane 2: WTshort probe+lysate from strain MN8; Lane 3: DEL probe only (no lysate); Lane 4: DEL probe+lysate from strain MN8; Lane 5: SUB probe only (no lysate); Lane 6: SUB probe+lysate from strain MN8.

The DNA-binding factor in *S. aureus* MN8 lysate has a higher affinity for the wildtype sequence. Short (53 bp) oligonucleotides were also generated which contained the 5 bp deletion (DEL) or the 5 bp substitution (SUB). FIG. 7 indicates that the DEL and SUB probes were not shifted by the factor(s) in the MN8 lysate as was the WT probe. These results demonstrate that the 5 bp motif is required for binding of at least one staphylococcal DNA binding protein. These findings thus support the conclusion that the DNA binding protein is a repressor and that the constitutive PNAG-over-production by strain MN8m and *S. aureus* strains transduced with the pMUC, pDEL, and pSUB constructs is due to the inability of this repressor to bind to the altered ica promoter.

Figure 8:
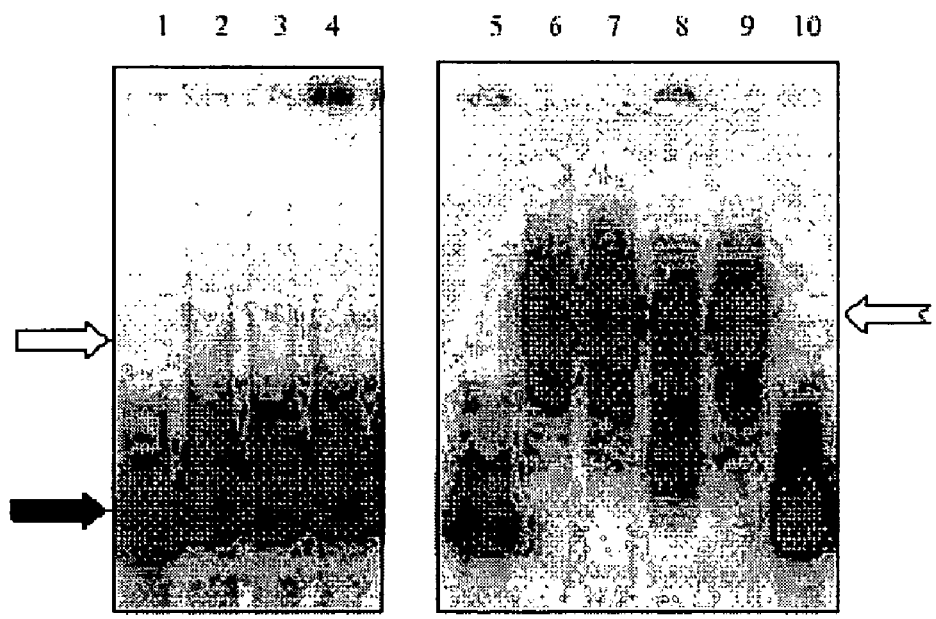
FIG. 8 shows that recombinant IcaR binds to the ica promoter DNA sequence located between the icaR and icaA genes. A radiolabeled oligonucleotide representative of a 198-bp region containing the ica promoter from wild type S. aureus was added to recombinant IcaR protein with either non-specific or specific unlabeled 198-bp oligonucleotide competitors. Solid arrow indicates free probe, open arrow is a minor nonspecific mobility shift induced by the recombinant protein expression control that is not inhibited by unlabeled, specific oligonucleotide, and open notched arrow (right side of Figure) is the mobility shift induced by IcaR. Lane 1: Free probe only (no recombinant protein); Lane 2: recombinant protein expression control; Lane 3: recombinant protein expression control+100× nonspecific cold competitor DNA; Lane 4: recombinant protein expression control+100× specific cold competitor; Lane 5: Free probe (no recombinant protein); Lane 6: recombinant IcaR; Lane 7: recombinant IcaR+10× nonspecific cold competitor DNA; Lane 8: IcaR+ 10× specific competitor DNA; Lane 9: IcaR+100× nonspecific cold competitor DNA; Lane 10: IcaR+100× specific competitor DNA.
Figure 9:
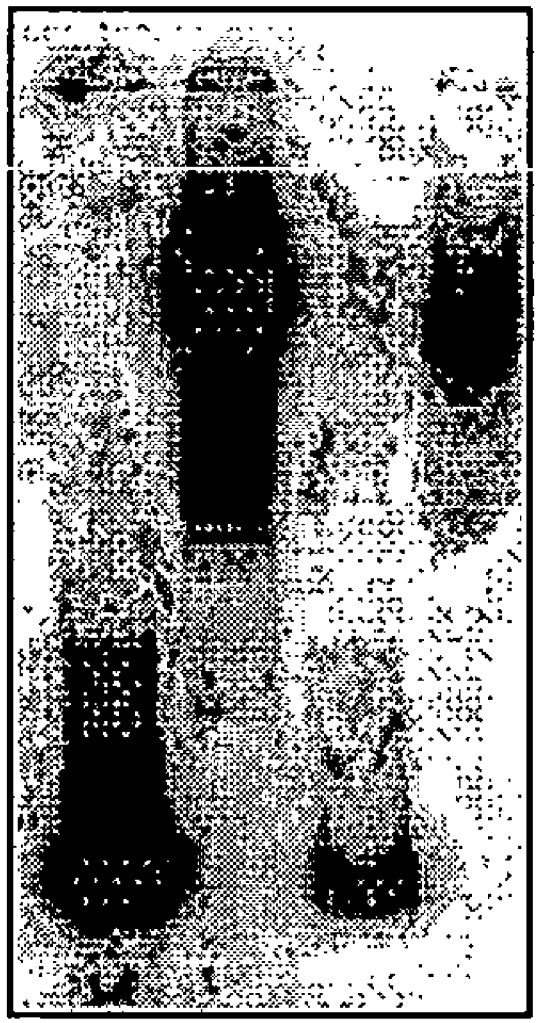
FIG. 9 shows that recombinant IcaR binds to the ica promoter from both *S. aureus* MN8 and *S. aureus* MN8m ica alleles. Electrophoretic mobility shift assay using a radiolabeled 198-bp oligonucleotide from the wild type strain MN8 (WT probe) or a 193-bp oligonucleotide from the MN8m strain (MUC probe) combined with recombinant IcaR protein. Recombinant IcaR binds to both promoters. Lane 1: free WT probe (no IcaR protein); Lane 2: IcaR protein+WT probe; Lane 3: free MUC probe (no IcaR protein); Lane 4: IcaR protein+MUC probe.

Recombinant IcaR induces a mobility shift in the wildtype and mutant probes. The protein encoded by the icaR gene exhibits homology to the TetR family of regulatory proteins. It was hypothesized that IcaR was the DNA binding protein detected in the mobility shift assays. Recombinant, histidine-tagged IcaR was expressed in *E. coli* and purified by nickel affinity chromatography. The purified protein was subjected to gel shift analysis using the 198 bp WT probe. Recombinant IcaR produced a shift in the mobility of the 198 bp WT probe (FIG. 8). The specificity of the mobility shift is indicated by the loss of the shifted band when a 100-fold excess of specific unlabeled competitor DNA was used. A nonspecific competitor, a 198 bp stretch of DNA from the icaA gene coding sequence, had no effect on the mobility shift (FIG. 8). The vector control induced a weak shift but this shift was not reduced by a 100-fold excess of specific competitor, indicating the non-specific nature of the minor shift observed. There was no detectable difference in the binding of recombinant IcaR to the WT and MUC probes (FIG. 9). When the 53 bp probe was used, WTshort (see FIG. 6) in a gel shift assay with IcaR no binding to the probe was seen (data not shown). This suggests that a DNA binding protein(s) other than IcaR is involved in regulation of ica transcription that is affected by the 5 bp deletion in the ica locus of strain MN8m.

Figure 10:
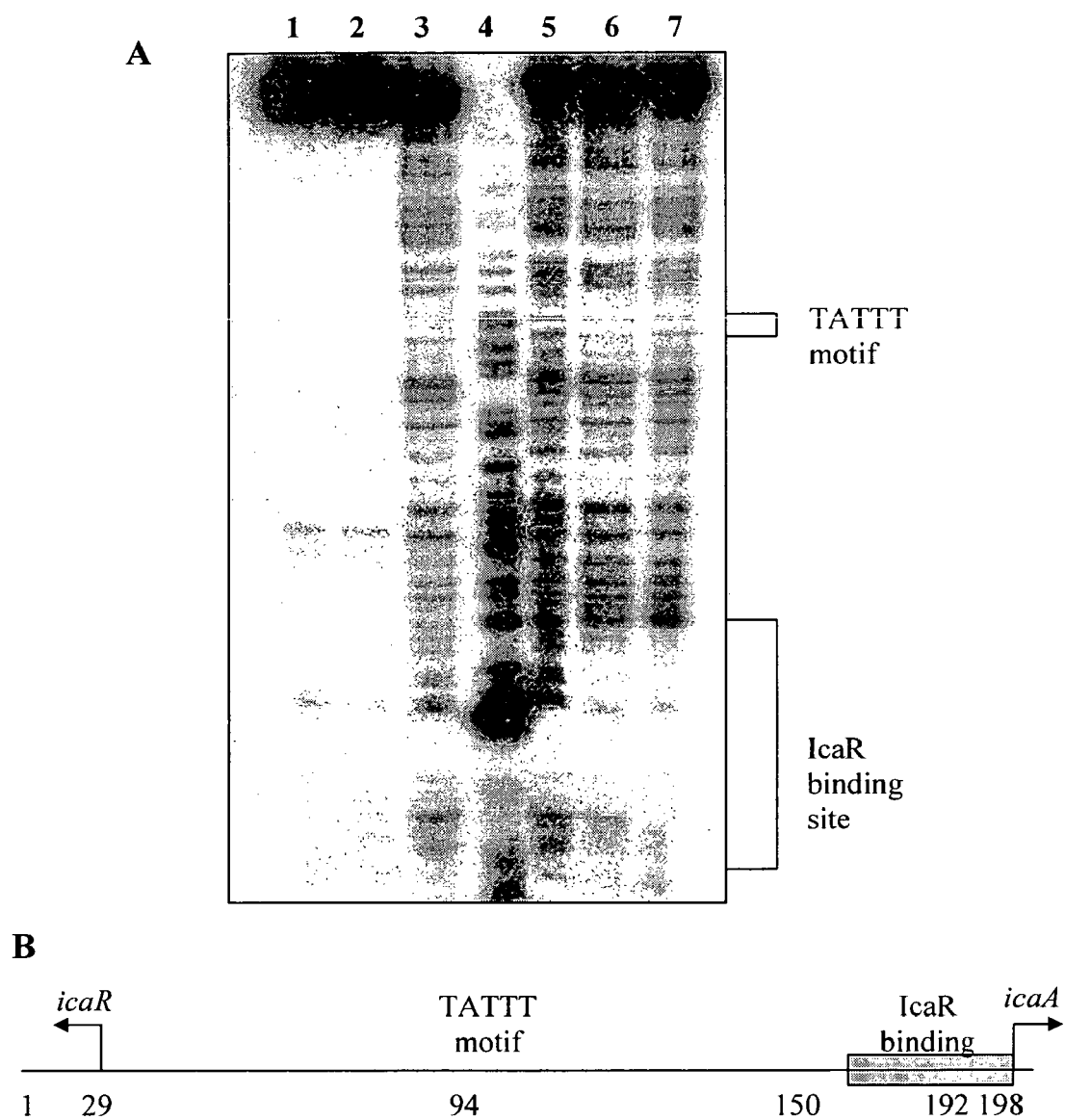
FIG. 10A shows that recombinant IcaR binds immediately upstream from icaA start site. DNaseI protection in the presence of recombinant IcaR was assayed using a radiolabeled 198-bp oligonucleotide from the wild type strain MN8 (WT probe). Lane 1: free DNA probe (no IcaR protein); Lane 2: DNA probe+10 μg IcaR; Lane 3: DNaseI-digested probe; Lane 4: sequencing control; Lane 5: DNaseI-digested probe+ 2.5 μg IcaR; Lane 6: DNaseI-digested probe+5 μg IcaR; Lane 7: DNaseI-digested probe+10 μg IcaR. The region protected by IcaR is indicated. The TATTT motif which is deleted in the mucoid strain is not protected by IcaR.
FIG. 10B is an illustration of the probe used in the assay shown in FIG. 10A. The numbers shown correspond to the nucleotides in the probe. The IcaR protein binds just upstream from the icaA start and does not bind in the region of the TATTT motif.

IcaR binds to the DNA sequence proximal to icaA. A a solid-phase DNaseI protection technique was used to locate the IcaR-binding domain within the ica promoter. Recombinant IcaR protected a 42-bp region immediately upstream from the icaA gene but did not bind in the region containing the 5-bp TATTT motif (FIG. 10). This finding supports the conclusion that the role of the 5-bp motif in transcriptional control of the ica locus is independent of IcaR and suggests that IcaR may function by sterically hindering the binding of the σ-factor of the RNA polymerase complex to the icaA promoter.

DNA Affinity Chromatography: Double-stranded, terminally-biotinylated DNA oligonucleotide with the following sequence CTA TGT TAC AGG AAA ATT AAG TTG CAA TTA CAA ATA TTT CCG TTT AAT TAT AA (SEQ ID NO:17) was coupled to streptavidin-coated magnetic beads (Dynabeads, Dynal). Lysate was made from *S. aureus* strain MN8 and added to the beads in the presence of non-specific carrier DNA so that specific oligo-binding proteins could bind to the beads. A magnet was used to pull the beads (and consequently the DNA-binding proteins) out of solution. The beads were washed and the proteins eluted in high salt. The proteins were then electrophoresed on a denaturing polyacrylamide gel, stained with Commassie blue, excised using a razor blade and sequence analyzed by mass spectral analysis.

This analysis demonstrated that IcaR bound to the ica wildtype promoter, but was not isolated by DNA affinity chromatography. IcaR corresponds to GenBank deposit having accession number BAB58827 (14248440). Proteins that were isolated by DNA affinity chromatography include DNA-binding protein II (nucleic acid sequence GenBank deposit having accession number NP_371997 (15924463)); TcaR transcription regulator (nucleic acid sequence GenBank deposit having accession number NP_372881 (15925347)); and sarA (Staphylococcal accessory regulator A) (nucleic acid sequence GenBank deposit having accession number NP_371140 (15923606)).

Discussion

Virtually all clinical isolates of *S. epidermidis* and *S. aureus* carry the ica genes (Muller et al., 1993; Ziebuhr et al, 1997). The ica locus has been shown to correlate with biomaterial adherence, a feature that differentiated commensal skin isolates of *S. epidermidis* from isolates recovered from prosthetic joint infections (Galdbart et al., 2000). Despite its importance in pathogenesis, very little is known about the regulation of transcription of the ica locus. Although a role for the alternative sigma factor sigma$^B$ has been suggested, the lack of a sigma$^B$ consensus binding site within the promoter sheds doubt on its direct involvement in the transcriptional activation of ica (Knobloch et al., 2001; Rachid et al., 2000a; Rachid et al., 2000b). The *S. aureus* strain MN8m was previously shown by immunochemical analysis to constitutively over-produce PNAG (McKenney et al., 1999). Using this strain to probe the regulation of ica transcription and biofilm formation, it has now been demonstrated according to the invention that a specific 5 bp motif in the ica promoter region plays an important role in the control of transcription of this locus and that the spontaneous loss of this putative binding site in *S. aureus* strain MN8m is the cause for the PNAG-over-producing phenotype. Transfer of the strain MN8m ica allele to two *S. aureus* strains deleted for the chromosomal ica locus also resulted in hyperproduction of PNAG as determined in the biofilm assay. Gel mobility shift studies showed the presence of cytoplasmic DNA binding proteins that bound to the wild-type but not mutant ica promoter. Further analysis of the IcaR protein also showed that it bound specifically to the ica promoter but that there was no difference in the binding of IcaR to wild-type or mutant promoter sequences.

The IcaR protein, which exhibits homology to the tetracycline regulatable (TetR) family of transcriptional regulators. The data presented herein show that IcaR is a DNA binding protein which attaches specifically to the ica promoter region. Gel mobility shifts with probes of varying lengths indicated that a relatively long (between 160-198 nucleotides) stretch of DNA is required for binding of IcaR. Within the sequence of DNA bound by IcaR is an 8 bp perfect inverted repeat. One repeat is proximal to the 5 bp motif that is deleted in the ica allele from strain MN8m, and the other is found at the start site of the icaA gene. The two repeats are separated by 100 nucleotides. The TetR family of DNA-binding proteins bind as dimers to such inverted repeats; it is therefore possible that IcaR inhibits transcription of ica by binding to the inverted repeats as a dimer and causing the intervening sequence to form a loop of DNA that prevents gene transcription. The finding that IcaR bound equally well to the full-length ica promoter regions from strains MN8 (WT) and MN8m (MUC) was unexpected given that the absence of the 5 nucleotide motif results in high levels of ica transcription. One protein, possibly IcaR, was found within crude cell-free extracts from strain MN8 that bound to both full-length WT and MUC promoter sequences equivalently and a second mobility shift occurred when the WT, but not the MUC promoter sequence, was used. In addition, a protein within the crude extracts was able to shift a 53-bp portion of the WT but not the MUC ica promoter sequence, whereas recombinant IcaR failed to bind to either of these short probes. Together these findings indicate that other DNA binding proteins are involved in interactions with the ica promoter and in regulating its transcription. These proteins include SarA, hu and TcrA.

One explanation for the failure of IcaR to discriminate between the WT and MUC promoter sequences is that the TATTT motif that is deleted in the MN8m ica promoter is normally required for precise bending of the ica locus and subsequent binding of IcaR, but that this bending is not affected to the same degree in a 198 bp recreation of the promoter. Stretches of adenosine and thymidine residues cause intrinsic bends in DNA. If IcaR does bind to the inverted repeat within the ica promoter then an intrinsic bend might be required to bring the two repeats close enough together to be bound by the IcaR protein. Using the program Model-it, it was found according to the invention, that deletion of TATTT reduces an intrinsic bend within the ica promoter and substitution of the motif with ATAAA causes the DNA to bend in the opposite direction (data not shown).

In summary, the TATTT motif located in the center of the ica promoter plays a critical role in the regulation of the ica locus. The IcaR protein is a DNA binding protein that attaches specifically to the DNA within the ica promoter region. At least one other staphylococcal DNA binding protein binds within the ica promoter and this binding is dependent upon the presence of the TATTT motif. These findings provide additional insight into understanding the mechanism of transcriptional regulation of the staphylococcal ica locus.

REFERENCES

Aki, T., and Adhya, S. (1997) Repressor Induced Site-Specific Binding of HU For Transcriptional Regulation. *EMBO J* 16: 3666-3674.

Bruckner, R. (1997) Gene replacement in *Staphylococcus carnosus* and *Staphylococcus xylosus*. *FEMS Micro Lett* 151: 1-8.

Christensen, G. D., Simpson, W. A., Younger, J. J., Baddour, L. M., Barrett, F. F., Melton, D. M., and Beachey, E. H. (1985) Adherence of coagulase-negative staphylococci to plastic tissue culture plates: a quantitative model for the adherence of staphylococci to medical devices. *J Clin Micro* 22: 996-1006.

Conlon, K. M., Humphreys, H., and O'Gara, J. P. (2002) icaR encodes a transcriptional repressor involved in environmental regulation of ica operon expression and biofilm formation in *Staphylococcus epidermidis*. *J. Bacteriol* 184: 4400-4408.

Cramton, S. E., Gerke, C., Schnell, N. F., Nichols, W. W., and Götz, F. (1999) The intercellular adhesion (ica) locus is present in *Staphylococcus aureus* and is required for biofilm formation. *Infect Immun* 67: 5427-5433.

Cramton, S. E., Gerke, C., and Götz, F. (2001a).In vitro methods to study staphylococcal biofilm formation. In Microbial Growth in Biofilms. Doyle R. J. (ed). New York: Academic Press. *Methods Enzymol* 336:239-255.

Cramton, S. E., Ulrich, M., Götz, F., and Döring, G. (2001b) Anaerobic conditions induce expression of polysaccharide intercellular adhesin in *Staphylococcus aureus* and *Staphylococcus epidermidis*. *Infect Immun* 69: 4079-4085.

Fournier, B., Aras, R., and Hooper, D. C. (2000) Expression of the multidrug resistance transporter NorA from *Staphy-*

*lococcus aureus* is modified by a two-component regulatory system. *J Bacteriol* 182: 664-671.

Galdbart, J. O., Allignet, J., Tung, H. S., Ryden, C., and El Solh, N. (2000) Screening for *Staphylococcus epidermidis* markers discriminating between skin-flora strains and those responsible for infections of joint prostheses. *J Infect Dis* 182: 351-355.

Götz, F. (2002) *Staphylococcus* and biofilms. *Mol Micro* 43:1367-1378. Heilmann, C., Schweitzer, O., Gerke, C., Vanittanakom, N., Mack, D., and Götz, F. (1996) Molecular basis of intercellular adhesion in the biofilm-forming *Staphylococcus epidermidis*. *Mol Micro* 20: 1083-1091.

Kar, S., and Adhya, S. (2001) Recruitment of HU by piggyback: a special role of GalR in repressosome assembly. *Genes & Development* 15: 2273-2281.

Kasatiya, S. S., and Baldwin, J. N. (1967) Nature of the determinant of tetracycline resistance in *Staphylococcus aureus*. *Canadian Journal of Microbiology* 13: 1079-1086.

Knobloch, J. K., Bartscht, K., Sabottke, A., Rohde, H., Feucht, H. H., and Mack, D. (2001) Biofilm formation by *Staphylococcus epidermidis* depends on functional RsbU, an activator of the sigB operon: differential activation mechanisms due to ethanol and salt stress. *J Bacteriol* 183: 2624-2633.

Lee, J. C. (1993) Electrotransformation of Staphylococci. In Methods in Molecular Biology. Nickloloff, J. A. (ed) Totowa: Humana Press Inc, pp.209-212.

Mack, D., Fischer, W., Krokotsch, A., Leopold, K., Hartmann, R., Egge, H., and Laufs, R. (1996) The intercellular adhesin involved in biofilm accumulation of *Staphylococcus epidermidis* is a linear beta-1,6-linked glucosaminoglycan: purification and structural analysis. *J Bacteriol* 178: 175-183.

McKenney, D., Hubner, J., Muller, E., Wang, Y., Goldmann, D. A., and Pier, G. B. (1998) The ica locus of *Staphylococcus epidermidis* encodes production of the capsular polysaccharide/adhesin. *Infect Immun* 66: 4711-4720.

McKenney, D., Pouliot, K. L., Wang, Y., Murthy, V., Ulrich, M., Döring, G., Lee, J. C., Goldmann, D. A., and Pier, G. B. (1999) Broadly protective vaccine for *Staphylococcus aureus* based on an in vivo-expressed antigen. *Science* 284: 1523-1527.

Muller, E., Takeda, S., Shiro, H., Goldmann, D., and Pier, G. B. (1993) Occurrence of capsular polysaccharide/adhesin among clinical isolates of coagulase-negative staphylococci. *J Infect Dis* 168: 1211-1218.

Munteanu, M. G., Vlahovicek, K., Parthasaraty, S., Simon, I. and Pongor, S. (1998) Rod models of DNA: sequence-dependent anisotropic elastic modelling of local bending phenomena. *Trends Biochem. Sci.* 23: 341-346.

Novick, R. (1967) Properties of a cryptic high-frequency transducing phage in *Staphylococcus aureus*. *Virology* 33: 155-166.

Orth, P., Schnappinger, D., Hillen, W., Saenger, W., and Hinrichs, W. (2000) Structural basis of gene regulation by the tetracycline inducible Tet repressor-operator system. *Nat Struct Biol* 7: 215-219.

Peacock, S. J., Moore C. E., Justice A., Kantzanou M., Story L., Mackie K., O'Neill G., Day N. P. (2002) Virulent Combinations of Adhesin and Toxin Genes in Natural Populations of *Staphylococcus aureus*. *Infect Immun* 70: 4987-4996.

Rachid, S., Cho, S., Ohlsen, K., Hacker, J., and Ziebuhr, W. (2000a).Induction.of *Staphylococcus epidermidis* biofilm formation by environmental factors: the possible involvement of the alternative transcription factor sigB. *Advances in Exp Med Biol* 485: 159-166.

Rachid, S., Ohlsen, K., Wallner, U., Hacker, J., Hecker, M., and Ziebuhr, W. (2000b) Alternative transcription factor Sigma(B) is involved in regulation of biofilm expression in a *Staphylococcus aureus* mucosal isolate. *J Bacteriol* 182: 6824-6826.

Rachid, S., Ohlsen, K., Witte, W., Hacker, J., and Ziebuhr, W. (2000c) Effect of subinhibitory antibiotic concentrations on polysaccharide intercellular adhesin expression in biofilm-forming *Staphylococcus epidermidis*. *Antimicrob Agents Chemother* 44: 3357-3363.

Ziebuhr, W., Heilmann, C., Götz, F., Meyer, P., Wilms, K., Straube, E., and Hacker, J. (1997) Detection of the intercellular adhesion gene cluster (ica) and phase variation in *Staphylococcus epidermidis* blood culture strains and mucosal isolates. *Infect Immun* 65: 890-896.

Example 2

Introduction:

A DNA affinity chromatography (DAC) system was developed to purify potential regulatory proteins that bind to the ica promoter region. Using this technique it was shown that the staphylococcal gene regulator. SarA, a MarR family transcriptional regulator of the teicoplanin associated locus, TcaR, DNA-binding protein II, and Topoisomerase IV bound to the ica promoter. Site-directed deletion mutagenesis of TcaR indicated that TcaR is a negative regulator of ica transcription but an effect on PNAG production was not detected in two clinical isolates. The role of IcaR was also studied. IcaR is encoded within the ica locus but divergently transcribed from the biosynthetic genes. It was shown that IcaR is also a negative regulator of the ica transcription, PNAG production, and biofilm formation. Overall, there are multiple ica-promoter binding proteins with potential regulatory functions, the activities of which may be manifest under the different conditions known to affect staphylococcal biofilm formation.

Materials & Methods

Stahylococcal strains and media. The same strains as described in Example 1 were used in these experiments. The strains were grown at 37° C. on tryptic soy agar plates containing the appropriate antibiotic. Liquid cultures were either in Tryptic Soy broth (TSB) lacking glucose (17 g/L peptone from casein, 3 g/L peptone from soymeal, 5 g/L NaCl, 2.5 g/L $K_2HPO_4$) or in TSB+1% glucose (TSBG).

Plasmids, primers, and cloning. Some plasmids are as described in Example 1. The expression plasmid pCRT7-NT (Invitrogen) was used to clone and express the tcaR gene. The tcaR gene was amplified using the primer pair tcaRF: (TTTCTTCAAAAATATATTTAGTAGCGAATACAC) and tcaRR: (AAGGATAAGATTATTGATAACGCAATAAC). The recombinant proteins were expressed in *E. coli* BL21pLysS cells according to manufacturer's instructions. The pCRT7-NT vector adds a tag of 6 histidine residues and an Xpress epitope to the amino-terminus of the protein. The IcaR and TcaR proteins and the vector expression control (the histidine tag and Xpress epitope alone) were sequentially purified using Probond nickel affinity chromatography resin (Invitrogen) and the strong cation exchange resin HiTrap SP XL (Amersham). The lac operon from *S. xylosus* was amplified by PCR (lacHfwd: GAGTGAGTGCTCATTGCTTG lacHrev: GCCCTAGTTGACTATCATTAG) and cloned into the EcoRV site of the temperature-sensitive plasmid pBT9 (2). The resulting plasmid was amplified with the primer pair (lacHmutfwd: GGACATGTTCCGACACTCGG lacHmutrev: TGATCTTCAAGATAGGTTCCATC) to delete the KpnI site within the LacH gene, and religated to create pLacH. All plasmid constructs were initially transformed into the restriction-deficient *S. aureus* strain RN4220 according to the method of Lee (14). Constructs were transferred to other strains of *S. aureus* by transduction using phage 80 (12). In order to create icaR and tcaR deletants, the region surrounding the gene was amplified by PCR from strain 10833 total DNA using one of the primer pairs (icaRdelfwd: and icardelrev: GGGGGTACCGGAAAC-CTTTTCGTTTTCATTGTGC or tcaRdelfwd: GGGGG-TACCCTTCAGTAACATCTACCGTTTCAGAATTAC and tcaRdelrev: GGGGGTACCGTGATATGGTGTATGACT-TCCGACACCATC) and cloned into pCR-TOPO (Invitrogen). The resulting plasmid was amplified with (icaR-xhofwd: CTCGAGCATCAAGTGTTGTACCGTCATACC and icaR-xhorev: CTCGAGTGGAGCAGTGGAAGAAAG-TAAAAGTC or tcaR-xhofwd: CTCGAGGTAAATGTTT-TACCATAATTATTTCTCCC and tcaR-xhorev: CTCGAG-GAAGATATTGAAAATGTAAGGCAAGTATTAGAAG), phosphorylated with T4 kinase, and re-ligated to produce a construct (pIcaRdel or pTcaRdel) with an XhoI restriction site in place of the coding region. The erythromycin resistance cassette was amplified from Tn917 by PCR (ermfwd: CTCGAGGCCTACGAGAAATTTGTATCG AND ermrev: CGTGTAACTTTCCAAATTTACAAAAGCG), digested with XhoI and ligated into the XhoI site of pIcaRdel-TOPO and pTcaRdel to create pIaR::erm-TOPO and pTcaR::erm-TOPO, respectively. The entire insert was then subcloned into the KpnI site of pLacH and transformed into RN4220 by electroporation. Transformants were cultured overnight at 30° C. in the presence of 10 µg erythromycin/ml and 10 µg chloramphenicol/ml, diluted 1:1000 and subcultured overnight at 42° C. without antibiotics. The cultures were diluted 1:10, plated on LB agar plates containing 10 µg erythromycin/ml and 200 µg Bluo-gal (Invitrogen)/ml, and grown for 48 hours at 42° C. White colonies were picked and screened for the double-crossover event, initially by PCR, and confirmed by DNA sequencing, which was carried out by the Microbiology Core Facility at Harvard Medical School (Boston, Mass.).

DNA affinity chromatography. 4L cultures of TSB were inoculated with 40 ml of an overnight culture of *S. aureus* MN8. Cultures were well aerated and grown at 37° C. for 5 hr ($OD_{600}$=0.9). Cells were lysed essentially as described by Fournier et al. (7); they were first washed in 200 ml buffer A (20 mM Tris-HCl, 50 mM $MgCl_2$, 1 mM dithiothreitol (DTT), 0.1 mM EDTA, 5% glycerol), frozen for 2 hr at −80°, and lysed in 50 ml buffer A containing 100 µg/ml lysostaphin and EDTA-free Complete Protease Inhibitors (Boehringer Mannheim) for 3.5 hr on ice. 30 ml buffer A+1.3 M KCl was added and. the incubation was continued on ice for 30 min. Lysates were cleared by centrifugation, precipitated with 50% ammonium sulfate at 4° C. for 1 hr, resuspended in 2 ml PBS, and dialyzed through a 3,500 MWCO membrane (Pierce, Rockford, Ill.) overnight against 4 L 10 mM HEPES+1 mM $MgCl_2$+0.5 mM DTT at 4° C. 2 nmol double stranded probe was immobilized on 10 mg of streptavidin-coated M-280 Dynabeads (Dynal, Oslo, Norway) according to manufacturer's instructions. The beads were equilibrated with binding buffer-1 (BB-1: 10 mM HEPES, 60 mM KCl, 4 mM MgCl2, 0.1 mM EDTA, 0.1 mg/ml BSA, and 0.25 mM DTT). 1.5 mL cell-free lysate (approximately 20 mg of protein) was combined with 6 ml BB1 and 1.5 mg sonicated salmon sperm DNA (SSS) and chilled on ice for 10 min. The lysate mixture was added to the beads and incubated on ice for 10 min. The beads were washed once with BB1+200 □g/ml SSS and twice with BB1 without BSA or SSS. DNA-binding proteins were eluted with 1 ml 10 mM HEPES+0.25 M KCl. The eluate was concentrated and desalted using Microcon YM-3.5 centrifugal concentrators (Millipore). The concentrated sample was subjected to SDS PAGE using NuPAGE 4-15% gradient gels and MOPS buffer (Invitrogen). The gels were stained with Coomassie blue and protein bands were sliced from the gel and submitted to the Molecular Biology Core Facility (Dana-Farber Cancer Institute, Boston, Mass.) for sequencing by MALDI-TOF mass spectral analysis.

Electrophoretic mobility shift. The 198-bp probe was generated by PCR using genomic DNA from strain MN8 as a template obtained from either *S. aureus* MN8 to yield the WT probe or *S. aureus* MN8m to yield the MUC probe using the following primer pair: icaFWD: ATTGCGTTAT-CAATAATCTTATCCTTC and icaREV: TTGCAATTTCTT-TACCTACCTTTC. The nonspecific competitor used in gel-shift assays was also a 198-bp PCR product representing a sequence from the icaA gene and was amplified from MN8 total DNA using the following primer pair: icaA-FWD CCT-GTATTTATGTCTATTTACTGG and icaA-Rev CTTCTCG-TATTTGAGTGCAAG. The PCR products were purified using the Qiagen PCR purification kit. For gel shift analysis the double-stranded probes were labeled with $[\gamma\text{-}^{32}P]ATP$ using T4 kinase. Gel shift assays were performed essentially as described by Fournier (7). A 20 µl binding reaction containing 5-25 ng purified recombinant TcaR, 1 µg sonicated salmon sperm DNA and 1 µg polydIdC in BB1 was incubated at 21° C. for 10 min before adding 1 µl (20,000 cpm) radiolabeled probe. The reaction was incubated for an additional 15 min and loaded onto a 5% nondenaturing polyacrylamide gel and electrophoresed in pre-chilled 1× Tris/borate/EDTA (TBE) at 360V for 1 hour. Gels were dried and exposed to radiographic film overnight at −80° C.

DNase I footprint analysis. Footprinting was carried out essentially as described by Sandaltzopoulos and Becker (24). 10 pmol icaREV was end-labeled with γ-P32-ATP using T4 kinase. The labeled oligonucleotide was EtOH-precipitated and used in a 50 µl PCR reaction with 10 pmol 5'-biotinylated icaFWD and genomic DNA from MN8 as a template for the amplification of the 198-bp probe representing the ica promoter region. The biotinylated, radiolabeled PCR product was immobilized on 500 µg Dynabeads according to the manufacturer's instructions. The magnetic beads were resuspended in 100 µl binding buffer-2(BB-2: 10 mM Tris-Cl, 5mM MgCl2, 2 mM DTT, 50 µg/ml BSA, 2 µg/ml polydIdC, 0.5 µg/ml sonicated salmon sperm DNA, 100 mM KCl). 10 µl of oligonucleotide-coated beads, 100 ng purified recombinant TcaR in Tris buffer, and 25 µl BB-2 were combined and incubated for 10 min at 21° C. 5 µl of a DNaseI solution (10 mM Tris-Cl, 5 mM MgCl2, 2 mM DTT, 10 mM $CaCl_2$, 100 mM KCl, 2.5 U/ml DNaseI) was added and the reaction was carried out for 2 min at 21° C. before the addition of 50 µl 2× stop buffer (4M NaCl, 100 mM EDTA). A similar solid-phase technique was used for the sequencing control, whereby a 198-bp probe was generated by PCR using biotinylated icaFWD and cold icaREV primers. The PCR product was immobilized on Dynabeads. The beads were heated to 95° C. and washed with Tris-EDTA buffer to remove the antisense strand. $P^{32}$-labeled icaREV was annealed to the immobilized, single-stranded DNA and sequencing of the antisense strand was carried out using the dideoxyadenosine 5-triphosphate nucleotide mix included in the Sequenase Version 2.0 sequencing kit (USB, Cleveland, Ohio). The beads from the DNaseI protection and sequencing samples were resuspended in 95% formamide, 6 µg/ml bromophenol blue, heated to 76° C. for 5 minutes and loaded on a 6% pre-run sequencing gel at 55 W for 25 min. The gel was dried at 80° C. and analyzed by autoradiography.

RNA Slot-BlotAnalysis. *S. aureus* cultures were grown in TSB+1% glucose at 37° C. for 16 hr. RNA was extracted from $10^9$ cells using the RNeasy Protect miniprep kit and RNase-free DNase kit (Qiagen) as described in the manufacturer's instructions except that 0.1 mg/ml lysostaphin was used in place of lysozyme to lyse the cells. RNA concentrations were determined by absorbance at 260 nm and 10 µg of each sample was immobilized on a nylon membrane. The single icaADBC transcript was detected with a single-stranded DNA probe specific for icaAD that was generated by PCR (icaAfwd: GTATTTATGTCTATTTACTGGATTGTCG-GTTC and icaBrev: TCCGGCAATATGATCAAGATACT-CAACA) and labeled using the ECL direct nucleic acid labeling and detection system (Amersham). Blots were re-probed with a probe specific for the housekeeping gene DNA gyraseB which was also generated by PCR (gyrBFwd: TTATGGTGCTGGGCAAATACAAG and gyrBRev: ACCT-TCGAATTGAGGATCACC) to ensure equal loading.

Adherence assay. Microtiter well adherence assays for PNAG production were performed essentially as described by Valle et al with minor modifications (25). Cultures were grown overnight in tryptic soy broth (TSB)+1% glucose, diluted to $OD_{650}$ 2.0, and aliquoted into 96-well polystyrene flat bottom microtiter plates from Corning (Corning, N.Y.). For strain MN8m and its derivative strains the cultures were grown in TSB with 1% glucose and diluted to $OD_{650}$ 0.2 in TSB prior to plating. The plates were centrifuged 3,000 rpm for 10 min and incubated at 37° C. for 1 hour. The wells were emptied, washed twice with phosphate buffered saline (PBS), dried at ambient temperature, stained for 30 sec with safranin, and washed under gently running tap water. The stained bacteria were assessed visually for relative adherence and resuspended in 100 µl PBS by gentle sonication, transferred to new microtiter wells, and the $OD_{450}$ was determined using an ELISA reader.

PNAG slot blot analysis. PNAG slot blots were performed essentially as described previously (5) with minor modifications. Bacteria were grown overnight in TSB. The following morning cultures were diluted 1:100 in TSB+1% glucose and grown for 5 hr. $1 \times 10^9$ cells were pelleted, washed once with PBS, resuspended in 50 □l 5N NaOH, and vortexed for 30 sec. The extracts were cleared by centrifligation, diluted 1:5 in tris-buffered saline (TBS), and 100 µl of extract from *S. aureus* strains MN8 or 10833, or 1 µl from strain MN8m was serially diluted in TBS and immobilized on nitrocellulose using a vacuum manifold. Blots were blocked for 1 hr in 5% skim milk, probed with 1:10,000 rabbit antiserum specific for PNAG (17) for 2 hr at 21° C., washed, and probed with 1:10,000 goat anti-rabbit alkaline phosphatase conjugate for 1 hr at 21° C. Bands were visualized using the ECL kit (Amersham) and autoradiography.

Results

DNA Affinity Chromatoraphy. *S. aureus* strain MN8mucoid (MN8m) was originally isolated as a spontaneous PNAG-hyperproducing mutant of strain MN8. A deletion of a 5-nucleotide TATTT sequence located in the center of the ica promoter is sufficient for the PNAG-overproducing phenotype associated with strain MN8m. IcaR binds to a distinct region of the ica promoter and is unaffected by the deletion mutation. A DNA Affinity Chromatography (DAC) system was designed to isolate proteins with high affinity for a 58 bp oligonucleotide representing the region of the ica promoter surrounding the TATTT motif. The oligonucleotide was synthesized, biotinylated at one end, immobilized on streptavidin-coated magnetic particles, and used to purify specific DNA-binding proteins from *S. aureus* lysate. The purified proteins were separated by SDS-PAGE and sequenced. Mass spectral analysis identified two non-specific DNA binding proteins; DNA-binding protein II and Topoisomerase IV, and SarA. Mass spectral analysis also indicated that an approximately 20 kDa protein isolated from the DNA affinity beads was most likely TcaR, a protein that displays significant homology to the MarR family of regulatory factors. The tcaR gene is part of the three-cistron teicoplanin associated locus (tca), so named for the discovery that teicoplanin resistance increases in *S. aureus* when the locus is deleted or interrupted.

TcaR and the ica promoter. TcaR binds to the ica promoter specifically and with high affinity, and that binding is not dependent upon the 5-bp TATTT motif (data not shown). The footprinting pattern of TcaR binding indicates that TcaR binds to and protects the MUT ica promoter in much the same way that it binds to the WT promoter (data not shown). Overall, TcaR seems to protect multiple sites within the ica promoter. This could be a result of multiple TcaR recognition sites within the sequence or of oligomerization of the protein once it is bound to the promoter region.

The icaA,D,B,C genes are transcribed as a single transcript so detection of icaA,D mRNA is representative of the transcription of all four genes. Northern analysis indicated an approximately 5-fold increase in icaAD transcript level in all three strains in the absence of tcaR (data not shown). This increase was lost when the mutants were complemented in trans with a plasmid carrying tcaR under the control of an inducible promoter (ptcaR) indicating that the phenotype was due to the lack of tcaR. Thus, TcaR appears to be a negative regulator of ica transcription.

Deletion of tcaR did not have a significant effect on the ability of MN8 or 10833 to adhere to polystyrene, although binding of MN8m increased slightly.

Adherence to plastic is a good relative measure of PNAG production but it is possible for other surface proteins and polysaccharides to play a role in adherence. In order to measure PNAG production more directly, a PNAG slot-blot assay was performed using polyclonal antiserum specific for PNAG. Cell surface extracts were prepared from late log phase cultures grown in TSB+1% glucose, blotted onto nitrocellulose, and probed with a PNAG-specific polyclonal antiserum (17). As MN8m is a PNAG hyper-producer, extracts from this strain and MN8mΔtcaR::erm were diluted 100-fold before they were blotted onto nitrocellulose. Again, MN8Δica::tet and 10833Δica::tet were used as negative controls and did not react with the PNAG-specific antiserum. Surface extracts from MN8m produced a strong reaction with the antiserum and the extracts from the tcaR mutant were slightly more reactive, in agreement with the biofilm data. The tcaR mutants did not produce significantly more PNAG than the wild-type strains. Thus despite the increase in ica transcription in the absence of TcaR, there was no discernable effect on PNAG synthesis. The effects of the tcaR deletion might be manifest under different growth conditions. To test this, cultures were grown under various conditions that have been shown previously to affect biofilm formation including high osmolarity (4% NaCl), elevated temperature (45° C.), and the presence of a subinhibitory concentration of tetracycline (0.05 µg/ml) (22). The tcaR deletant did not exhibit significantly greater PNAG expression than the wild-type under any conditions (data not shown). These findings suggests that while TcaR appears to be a negative regulator of ica transcription, an effect on PNAG expression in the tcaR deletant strains is not detected by these methods. The effect of the tcaR deletion might be masked under normal growth conditions by either a post-transcriptional regulatory mechanism, or possibly by an additional negative regulator of transcription.

Figure 11:
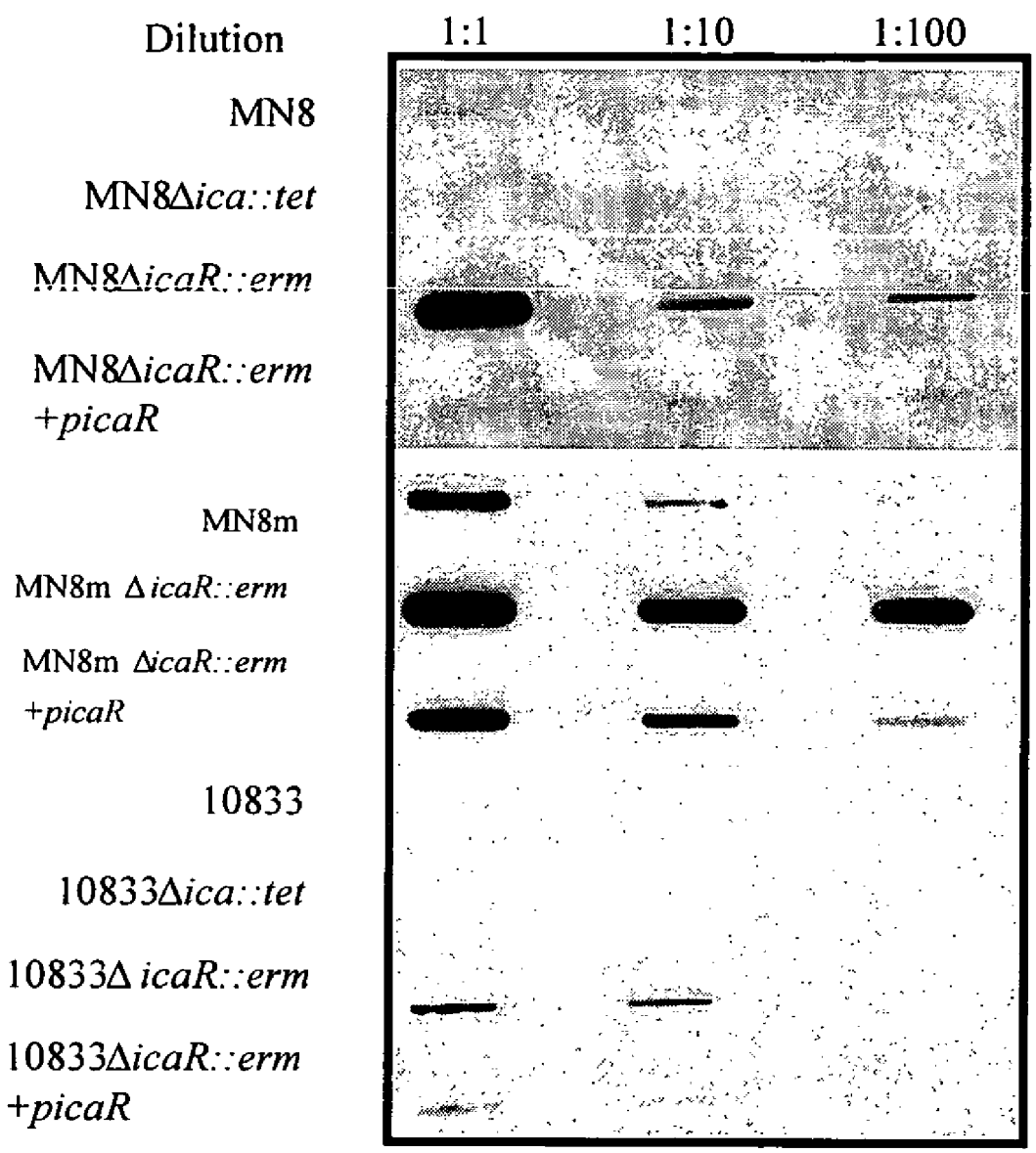
FIG. 11 shows that deletion of icaR augments icaADBC transcription in MN8, MN8m, and 10833. Total RNA was isolated from the indicated strains, serial dilutions of the RNA were made, and 10 μg, 0.4 μg, or 8 ng of MN8 and 10833 RNA or 2 μg, 0.4 μg, 0.08μg of MN8m RNA was immobilized onto nylon membranes using a slot-blot apparatus. The blots were probed with a single-stranded DNA probe specific for the icaAD transcript labeled with horseradish peroxidase. A chemiluminescent substrate was added and bands were visualized by autoradiography. Blots representative of 3 separate experiments are shown.

Effect of IcaR on icaADBC transcript levels. It has been reported that IcaR is a repressor of icaADBC transcription in *S. epidermidis* (3) although in this report, deletion of icaR did not affect biofilm formation. It was previously demonstrated by DNaseI protection and electrophoretic mobility shift analysis that IcaR binds to the *S. aureus* ica promoter but direct evidence that it is a repressor of ica transcription in *S. aureus* has not yet been presented (11). In order to confirm that IcaR acts as a repressor of ica transcription in *S. aureus*, the icaR gene was inactivated within three *S. aureus* strains, MN8, MN8m, and 10833 by allelic replacement with an erythromycin resistance cassette. Total RNA from 16 hr TSB+1% glucose cultures of the resulting strains, MN8ΔicaR::erm, MN8mΔicaR::erm, and 10833ΔicaR::erm, were subjected to Northern slot blot analysis using the icaAD-specific probe. All blots were also analyzed with a DNA gyrase-specific probe to ensure equal loading (data not shown). As explained above, only 2 μg of RNA from the MN8m and MN8mΔicaR::erm strains was analyzed whereas 10 μg of RNA from the MN8 and 10833 strains was analyzed. In all three strains inactivation of icaR increased the level of the icaA,D transcript (FIG. 11). This increase was estimated to be at least 100-fold as measured by densitometric analysis using NIH image software (data not shown). These results demonstrate that in *S. aureus*, IcaR is a repressor of ica transcription and that it is functional even in the. PNAG-overproducing strain MN8m. The finding that the negative regulatory effects of both IcaR and TcaR are unaffected by the 5-bp deletion within the ica promoter of MN8m is somewhat surprising considering that PNAG expression is so high in this strain. This suggests that MN8m may have lost a requirement for a positive regulator, or that the 5-bp deletion somehow increases the efficiency of transcriptional initiation by the RNA polymerase complex at this promoter.

Figure 12:
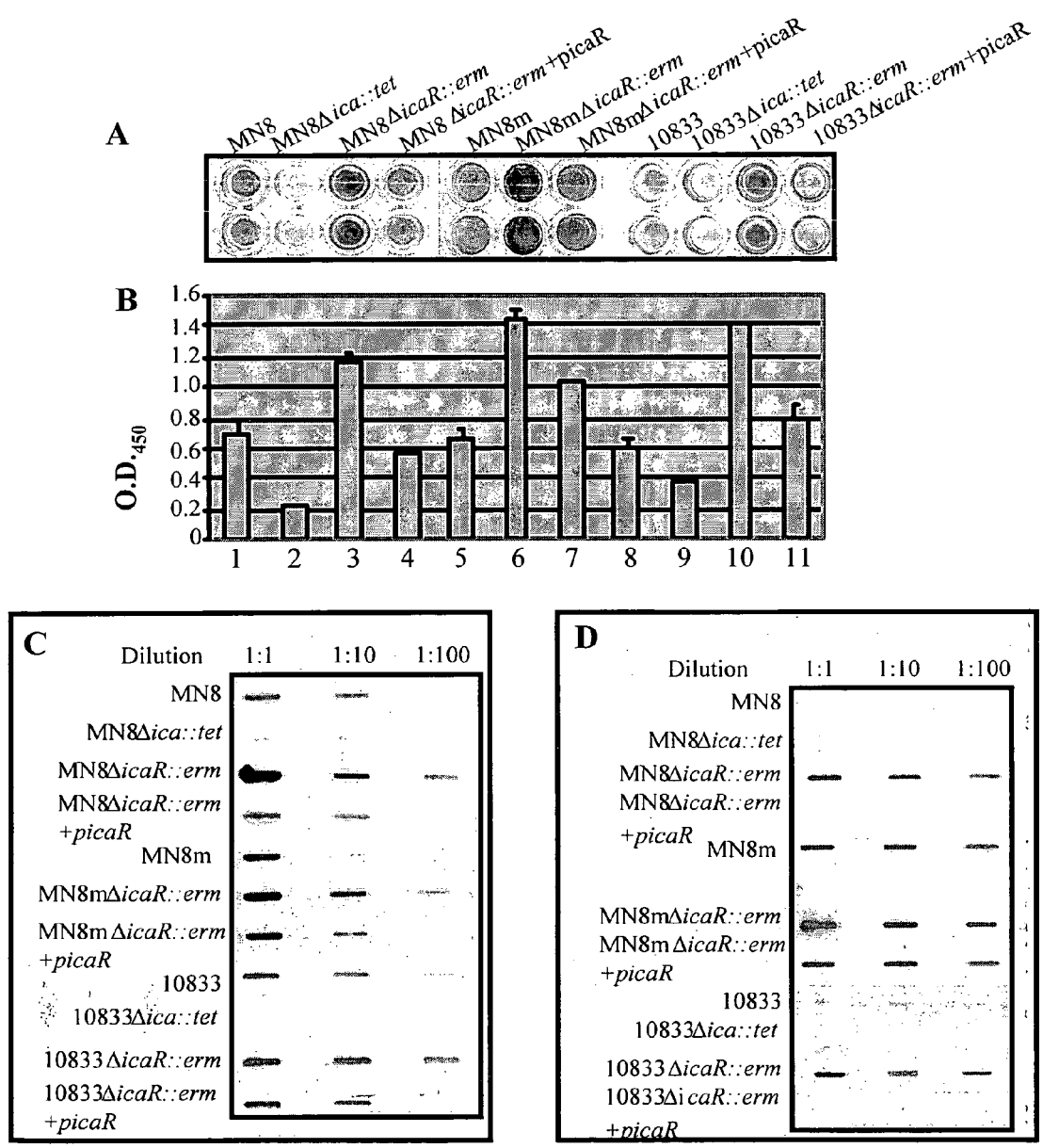
FIG. 12A shows that deletion of the icaR gene augments PNAG production and adherence in *S. aureus*. Bacteria were grown in TSB+1% glucose overnight. Strains MN8 and 10833 were diluted to $OD_{650}$ 2.0, MN8m strains were diluted to $OD_{650}$ 2.0 and 200 μl of each culture was added to wells in polystyrene microtiter plate. The wells were washed with PBS and adherent cells stained with safranin.
FIG. 12B. Following staining, 200 μl PBS was added to each microtiter well and the bacteria were homogenized by sonication. Bars reflect the mean $OD_{450}$ of eight samples and error bars, the standard deviations.
FIG. 12C. Bacteria were grown in TSB+1% glucose overnight. Cultures were diluted to $OD_{650}$ 1.0 and 1 ml was centrifuged to pellet the cells. Cell surface extracts were made by resuspending bacteria in 50 μl 5N NaOH. Extracts were cleared by centrifugation, diluted with 250 μl TBS, and serial 10-fold dilutions of 100 μl of MN8 and 10833 extracts or of 1 μl of MN8m extract were immobilized on nitrocellulose membranes. The blots were blocked with 5% milk, probed with PNAG-specific rabbit antiserum and polyclonal goat anti-rabbit alkaline phosphatase conjugate. A chemiluminescent substrate was added to the blots and bands were visualized by autoradiography.

Effect of icaR on PNAG production. To assess PNAG production in the icaR mutants the adherence assay was again used. As described above, strains MN8 and 10833 are low-level PNAG producers, and a high inoculum ($OD_{650}$ 2.0) was added to microtiter wells in order to produce a visible biofilm whereas MN8m is a high-level PNAG producer and a low inoculum ($OD_{650}$ 0.2) was added to wells for MN8m and the MN8mΔicaR::erm. The bacteria were allowed to adhere to the plastic wells for 1 hour after which non-adherent cells were removed by repeated washes and adherent cells were stained with safranin. Adherence was assessed by visual inspection of the dry, stained biofilms and by optical density of resuspended, stained bacteria (11). As shown in FIGS. 12A and 12B, the icaR knockout strains exhibited increased adherence to the polystyrene microtiter wells with respect to their parent strains. There was an approximately two fold increase in the $OD_{450}$ of the MN8ΔicaR::erm, MN8mΔicaR::erm, and 10833ΔicaR::erm constructs when compared to strains MN8, MN8m, and 10833 respectively. Complementation of the icaR deletions in trans restored the wild-type phenotypes confirming that the increase in adherence was a result of deleting icaR (FIGS. 12A, 12B). It is notable that strain MN8m, which normally produces copious quantities of PNAG, exhibited even greater adherence and was more aggregative in the absence of IcaR. On TSA plates MN8mΔicaR::erm formed small tight colonies that were even more sticky that MN8m colonies and when grown in TSB the bacteria were so aggregative that they formed a single compact pellet (data not shown). This suggests that despite the PNAG-hyperproducing phenotype of strain MN8m, IcaR-mediated repression of ica is still effective in this strain.

PNAG production was also measured in the icaR mutant strains. FIG. 12C shows that at 37° C. in TSB+1% glucose PNAG synthesis was approximately 10-fold higher in the icaR deletants than in the respective wild-type strains, substantiating the findings with the adherence assays. To confirm that the increase in PNAG production was a direct result of inactivating icaR, 10833ΔicaR::erm, MN8ΔicaR::erm, and MN8mΔicaR::erm were complemented with a plasmid carrying an inducible copy of the icaR gene (picaR). Complementation of the icaR gene in trans reduced PNAG expression to wild-type levels (FIG. 12C). This supports the role for IcaR as a repressor and together these findings confirm that IcaR is functional in MN8m and that constitutive hyperproduction of PNAG by MN8m is not due to a loss of the negative regulatory effect of IcaR.

It was noted when working with the MN8m strains that while the wild-type, MN8m was not mucoid in TSB made without glucose, MN8mΔicaR::erm was still extremely sticky even in the absence of glucose. PNAG blots were performed on the strains and icaR deletants grown in TSB without any glucose. The strains were first grown overnight in the absence of glucose, then diluted the following day 1:100 in TSB without glucose and grown to late log phase. FIG. 12D shows that deletion of icaR significantly augments PNAG production in the absence of glucose. In fact, in strains MN8 and 10833 PNAG production was undetectable by these methods in the absence of glucose but was strong in the icaR knockout strains. These findings demonstrate that IcaR is a negative regulator of PNAG production in *S. aureus* and suggest that it plays an important role in the suppression on PNAG production in the absence of glucose.

Discussion

It has been reported that IcaR is a repressor of ica transcription in *S. epidermidis*, although an influence of IcaR on PNAG production and biofilm formation has not been previously demonstrated (3). Here it has been shown that IcaR is also a repressor of ica transcription in *S. aureus* and that deletion of icaR results in a substantial increase in PNAG elaboration. Evidence is also presented that IcaR plays a role in the supportive effect that glucose has on PNAG production. Dobinsky et al. reported that despite elevated transcription of the icaADBC genes, *S. epidermidis* is PNAG-negative in the absence of glucose. In the presence of glucose, the level of icaADBC transcript was very low but PNAG was produced. The most intuitive explanation for this dissociation between ica transcription and PNAG production is that glucose is required as a substrate for factors involved in PNAG production. Further evidence is provided that in *S. aureus* the glucose-mediated increase in PNAG is due, at least in part, to alleviation of IcaR-mediated repression and a subsequent increase in ica transcription. When icaR is deleted in strains MN8, 10833m and MN8m ica transcription is elevated and PNAG production is greatly increased even in the absence of any exogenous glucose source. This strongly suggests that the positive effect that glucose has on PNAG expression is a result of alleviation of IcaR-mediated repression and transcriptional activation of ica.

TcaR proved to have a strong interaction with the ica promoter in vitro. Although Northern analysis of tcaR knockout strains suggested that it is a negative regulator of ica transcription, deletion of tcaR did not have a significant impact on PNAG production. As discussed above icaADBC transcript levels and PNAG production are not always directly related;

in *S. epidermidis*, Conlon et al. demonstrated an increase in icaADBC transcript levels but found no significant effect on biofilm formation in their icaR deletant (3), and Dobinsky et al. found a dissociation between ica transcription and PNAG production when the bacteria were grown in the presence or absence of glucose (6). It is possible that the discrepancy between ica transcription and PNAG production noted in these reports and in the tcaR deletion mutants is due to a post-transcriptional regulatory mechanism. A search for a transcriptional start site within the ica promoter using the Neural Network Promoter Prediction program, suggested the presence of multiple transcriptional start sites (23). Therefore, alternate promoter usage may result in incomplete transcription of the ica locus or in post-transcriptional control mechanisms. Alternatively, IcaR or some other negative regulator may repress PNAG synthesis in the absence of TcaR.

REFERENCES

1. Beenken, K. E., J. S. Blevins, and M. S. Smeltzer. 2003. Mutation of sarA in *Staphylococcus aureus* limits biofilm formation. Infect. Immun. 71:4206-4211.
2. Brückner, R. 1997. Gene replacement in *Staphylococcus carnosus* and *Staphylococcus xylosus*. FEMS Microbiol. Lett. 151:1-8.
3. Conlon, K. M., H. Humphreys, and J. P. O'Gara. 2002. icaR encodes a transcriptional repressor involved in. environmental regulation of ica operon expression and biofilm formation in *Staphylococcus epidermidis*. J. Bacteriol. 184:4400-4408.
4. Cramton, S. E., C. Gerke, N. F. Schnell, W. W. Nichols, and F. Götz. 1999. The intercellular adhesion (ica) locus is present in *Staphylococcus aureus* and is required for biofilm formation. Infect. Immun. 67:5427-33.
5. Cramton, S. E., M. Ulrich, F. Götz, and G. Döring. 2001. Anaerobic conditions induce expression of polysaccharide intercellular adhesin in *Staphylococcus aureus* and *Staphylococcus epidermidis*. Infect. Immun. 69:4079-85.
6. Dobinsky, S., K. Kiel, H. Rohde, K. Bartscht, J. K. Knobloch, M. A. Horstkotte, and D. Mack. 2003. Glucose-related dissociation between icaADBC transcription and biofilm expression by *Staphylococcus epidermidis*: evidence for an additional factor required for polysaccharide intercellular adhesin synthesis. J. Bacteriol. 185:2879-86.
7. Fournier, B., R. Aras, and D. C. Hooper. 2000. Expression of the multidrug resistance transporter NorA from *Staphylococcus aureus* is modified by a two-component regulatory system. J. Bacteriol. 182:664-71.
8. Galdbart, J. O., J. Allignet, H. S. Tung, C. Ryden, and N. El Solh. 2000. Screening for *Staphylococcus epidermidis* markers discriminating between skin-flora strains and those responsible for infections of joint prostheses. J. Infect. Dis. 182:351-5.
9. Götz, F., C. Heilmann, and S. E. Cramton. 2000. Molecular basis of catheter associated infections by staphylococci. Adv. Exp. Med. Biol. 485:103-11.
10. Heilmann, C., O. Schweitzer, C. Gerke, N. Vanittanakom, D. Mack, and F. Götz. 1996. Molecular basis of intercellular adhesion in the biofilm-forming *Staphylococcus epidermidis*. Mol. Microbiol. 20:1083-91.
11. Jefferson, K. K., S. E. Cramton, F. Götz, and G. B. Pier. 2003. Identification of a 5-nucleotide sequence that controls expression of the ica locus in *Staphylococcus aureus* and characterization of the DNA-binding properties of IcaR. Mol. Microbiol. 48:889-899.
12. Kasatiya, S. S., and J. N. Baldwin. 1967. Nature of the determinant of tetracycline resistance in *Staphylococcus aureus*. Can. J. Microbiol. 13:1079-86.
13. Knobloch, J. K., K. Bartscht, A. Sabottke, H. Rohde, H. H. Feucht, and D. Mack. 2001. Biofilm formation by *Staphylococcus epidermidis* depends on functional RsbU, an activator of the sigB operon: differential activation mechanisms due to ethanol and salt stress. J. Bacteriol. 183:2624-33.
14. Lee, J. C. 1993. Electrotransformation of Staphylococci, vol. 47. Humana Press Inc., Totowa, N.J.
15. Leid, J. G., J. W. Costerton, M. E. Shirtliff, M. S. Gilmore, and M. Engelbert. 2002. Immunology of Staphylococcal biofilm infections in the eye: new tools to study biofilm endophthalmitis. DNA Cell Biol. 21:405-13.
16. Lowy, F. D. 1998. *Staphylococcus aureus* infections. New Eng. J. Med. 339:520-32.
17. Maira-Litran, T., A. Kropec, C. Abeygunawardana, J. Joyce, G. Mark, 3rd, D. A. Goldmann, and G. B. Pier. 2002. Immunochemical properties of the staphylococcal poly-N-acetylglucosamine surface polysaccharide. Infect. Immun. 70:4433-40.
18. McKenney, D., J. Hubner, E. Muller, Y. Wang, D. A. Goldmann, and G. B. Pier. 1998. The ica locus of *Staphylococcus epidermidis* encodes production of the capsular polysaccharide/adhesin. Infect. Immun. 66:4711-20.
19. McKenney, D., K. L. Pouliot, Y. Wang, V. Murthy, M. Ulrich, G. Döring, J. C. Lee, D. A. Goldmann, and G. B. Pier. 1999. Broadly protective vaccine for *Staphylococcus aureus* based on an in vivo-expressed antigen. Science 284:1523-7.
20. Peacock, S. J., C. E. Moore, A. Justice, M. Kantzanou, L. Story, K. Mackie, G. O'Neill, and N. P. Day. 2002. Virulent combinations of adhesin and toxin genes in natural populations of *Staphylococcus aureus*. Infect. Immun. 70:4987-96.
21. Rachid, S., K. Ohlsen, U. Wallner, J. Hacker, M. Hecker, and W. Ziebuhr. 2000. Alternative transcription factor sigma(B) is involved in regulation of biofilm expression in a *Staphylococcus aureus* mucosal isolate. J. Bacteriol. 182:6824-6.
22. Rachid, S., K. Ohlsen, W. Witte, J. Hacker, and W. Ziebuhr. 2000. Effect of subinhibitory antibiotic concentrations on polysaccharide intercellular adhesin expression in biofilm-forming *Staphylococcus epidermidis*. Antimicrob. Agents Chemother. 44:3357-63.
23. Reese, M. G. 2001. Application of a time-delay neural network to promoter annotation in the *Drosophila melanogaster* genome. Comput. Chem. 26:51-56.
24. Sandaltzopoulos, R., and P. B. Becker. 1994. Solid phase DNase I footprinting: quick and versatile. Nucleic Acids Res. 22:1511-2.
25. Valle, J., A. Toledo-Arana, C. Berasain, J. M. Ghigo, B. Amorena, J. R. Penades, and I. Lasa. 2003. SarA and not sigma(B) is essential for biofilm development by *Staphylococcus aureus*. Mol. Microbiol. 48:1075-1087.

Equivalents

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. An isolated nucleic acid molecule selected from the group consisting of
    (a) a nucleic acid molecule which hybridizes under stringent conditions at 65° C. in hybridization buffer, washing at room temperature with 0.15 M sodium chloride, 0.015 M sodium citrate, pH 7 (SSC) and at 68° C. with 0.1-0.5×SSC, 0.1 sodium dodecyl sulphate to a nucleic acid molecule having the sequence of SEQ ID NO:2 and thereby spans nucleotides 23 and 29 of SEQ ID NO.:2, has an addition, deletion or substitution of at least two nucleotides in a TATTT sequence when compared to SEQ ID NO:2, is at least 48 nucleotides in length, and enhances production of poly-N-acetyl glucosamine when operably linked to an ica nucleic acid comprising nucleotides 2330-5745 of SEQ ID NO:3 that encode IcaA, IcaD, IcaB and IcaC, relative to the level of poly-N-acetyl glucosamine produced when SEQ ID NO:2 is operably linked to the ica nucleic acid, and
    (b) the complement thereof.

2. An expression vector comprising the isolated nucleic acid molecule of claim 1, operably linked to an ica nucleic acid.

3. A host cell transformed or transfected with the expression vector of claim 2.

4. An isolated nucleic acid molecule selected from the group consisting of
    (a) a fragment of a nucleic acid molecule consisting of the sequence of SEQ ID NO:1, and
    (b) the complements of (a),
    wherein the fragment spans nucleotides 23 and 24 of SEQ ID NO.:1, is at least 48 nucleotides in length, and enhances production of poly-N-acetyl glucosamine when operably linked to an ica nucleic acid comprising nucleotides 2330-5745 of SEQ ID NO:3 that encode IcaA, IcaD, IcaB and IcaC, relative to the level of poly-N-acetyl glucosamine produced when SEQ ID NO:2 is operably linked to the ica nucleic acid.

5. The isolated nucleic acid molecule of claim 1, wherein the isolated nucleic acid molecule consists of the sequence of SEQ ID NO:1.

6. The isolated nucleic acid molecule of claim 1, wherein the isolated nucleic acid molecule comprises the nucleotide sequence between and including nucleotides 9 and 38 of SEQ ID NO:1.

7. The isolated nucleic acid molecule of claim 1, wherein the isolated nucleic acid molecule comprises a deletion, addition or substitution of at least three, at least four or at least five nucleotides in the TATTT sequence.

8. The isolated nucleic acid molecule of claim 1, wherein the isolated nucleic acid molecule comprises a five nucleotide non-wildtype substitution of the TATTT sequence.

9. The isolated nucleic acid molecule of claim 8, wherein the five nucleotide non-wildtype substitution has a sequence of ATAAA.

10. The isolated nucleic acid molecule of claim 4, wherein the fragment has the nucleotide sequence between and including nucleotides 9 and 38 of SEQ ID NO:1.

11. An isolated nucleic acid molecule, selected from the group consisting of
   a) a nucleic acid molecule which
      (i) which varies from the sequence of SEQ ID NO:2 by having an addition, deletion or substitution of at least two nucleotides between and including nucleotides 24 and 28 of SEQ ID NO: 2, and which is at least 48 nucleotides in length, and
      (ii) enhances production of poly-N-acetyl glucosamine when operably linked to an ica nucleic acid comprising nucleotides 2330-5745 of SEQ ID NO:3 that encode IcaA, IcaD, IcaB and IcaC, relative to the level of poly-N-acetyl glucosamine produced when SEQ ID NO:2 is operably linked to the ica nucleic acid, and
   b) the complement thereof.

12. An isolated nucleic acid molecule comprising the nucleotide sequence of SEQ ID NO:1.

13. An isolated nucleic acid molecule consisting of the nucleotide sequence of SEQ ID NO:1.

14. A method of making a polysaccharide over-producing bacterium comprising introducing into a bacterium an ica nucleic acid operably linked to an ica regulatory nucleic acid,
   wherein the ica regulatory nucleic acid is the isolated nucleic acid molecule of claims 1, 4, 11, 12 or 13.

15. A recombinant polysaccharide over-producing bacterium comprising an ica nucleic acid operably linked to an ica regulatory nucleic acid,
   wherein the ica regulatory nucleic acid is the isolated nucleic acid molecule of claims 1, 4, 11, 12 or 13, and wherein the bacterium is not MN8m.

16. A method of producing a bacterial polysaccharide comprising culturing the polysaccharide over-producing bacterium of claim 15 in a growth medium, and
   harvesting the bacterial polysaccharide from the culture.

17. A method of over-producing a protein in a bacterium comprising
   introducing into a bacterium a nucleic acid operably linked to an ica regulatory nucleic acid,
   wherein the ica regulatory nucleic acid is the isolated nucleic acid of claims 1, 4, 11, 12 or 13, and wherein the nucleic acid encodes a protein to be over-produced.

* * * * *

UNITED STATES PATENT AND TRADEMARK OFFICE
CERTIFICATE OF CORRECTION

PATENT NO. : 7,723,087 B2  Page 1 of 1
APPLICATION NO. : 10/712391
DATED : May 25, 2010
INVENTOR(S) : Gerald B. Pier et al.

It is certified that error appears in the above-identified patent and that said Letters Patent is hereby corrected as shown below:

In the Claims:

At column 61, Claim 11, line 7, please delete "(i) which varies" and insert -- (i) varies --
At column 62, Claim 14, line 5, please delete "claims" and insert -- claim --
At column 62, Claim 15, line 10, please delete "claims" and insert -- claim --
At column 62, Claim 17, line 21, please delete "claims" and insert -- claim --

Signed and Sealed this

Tenth Day of August, 2010

David J. Kappos
*Director of the United States Patent and Trademark Office*

```
                         SEQUENCE LISTING

<160> NUMBER OF SEQ ID NOS: 20

<210> SEQ ID NO 1
<211> LENGTH: 55
<212> TYPE: DNA
<213> ORGANISM: Staphylococcus aureus

<400> SEQUENCE: 1
gaaaattaag ttgcaattac aaaccgttaa ttataacaac aatctattgc aaatt         55

<210> SEQ ID NO 2
<211> LENGTH: 60
<212> TYPE: DNA
<213> ORGANISM: Staphylococcus aureus

<400> SEQUENCE: 2
gaaaattaag ttgcaattac aaatatttcc gttaattata acaacaatct attgcaaatt    60

<210> SEQ ID NO 3
<211> LENGTH: 6520
<212> TYPE: DNA
<213> ORGANISM: Staphylococcus aureus

<400> SEQUENCE: 3
ggtaccgagc tcgctaatag gtgactttgg ttgttcatgg acaattaaac ttgatgtact    60
tcttcgtgta ttcgtcatgg taattcctcg taaattaaaa tttttgtatt gaacctaaaa   120
taggtaatcc tagttgcgat tcaacatctt cttctgtctt aatacgctta tctaataatt   180
cttttaagaa aataatcaat attgctaaaa caataccaac aataatgctg ataactaagt   240
tgacagatac tattggagat acttttacgg cattatcatg tgctgaggaa agtatcgtaa   300
cattatcaac actcataatt ttaggcatgt catgagcaaa aactttagat attttattaa   360
caattttgtc agattcagat ttattcccag tggtaactga tacagtaata atttgagagt   420
ttgtttgatt ggttactttt aaaaatgaat tcaactcagc tgttgaatac tgaccatcaa   480
attctctaga tactttatct agaattctag acttttgat aatttccgta tatgtattaa    540
cagactgcaa actactttga acattttgga aagctaaatc acttgaggac ttttcatgt    600 tcactaatat ttgagtagaa gcagtatatt tgtcaggcat aacaaaaaag gttaatgccg    660
cacttactac aagacatatt gccggtaaaa taagcaataa tttaatattc ttctttagaa    720
tatttaatag ttttactaaa tcaaacttttt ctttcatggt ttcctccaca taatcaatca   780
ttgtattcat tatgtatgtt ttataaatcg dacaattata tctagtttaa cgaccacaaa    840
acatacacaa ctcatttttc tctaattatt tatataaata ttttatcgtt taaaattata    900
tcatgattct ctaccattat gtataactta tttatatttt tgcacaagat ataatattgt    960
ccaactttaa atatccaaac ctattaataa taaaactaga taccatcgta ctctgtcatg   1020
gctttcttat aatcgagtag aagcatcatc attacttgat tatttgctct ttacaacacc   1080
gagcgtgccc gtactcggta attcaatacc ttgcgtaacc cgtcactgtg agttgggtta   1140
atgataataa agcccacacc ttttaaaaag atgtgggtaa tttatataat ttttatttac   1200
atttttaact tataaaaaaa agcgcctatg tcatgattta ccatcacata ggcgcttatc   1260
```

```
aataaattat tacttattac tttccatttc atctaattta tgcggattcc ctgtaattag    1320 atgcaactt attcttttca ggggaacatt acacttttat aatatgttca aagacaaact    1380
taaccattca caaatataaa gaataatatt atcaaatcat tgaacaaatc gtattttgca    1440
acaattgata tttatattaa tgtattgcat ttaatttata aaattcatat acatcttaat    1500
attctcaata tcgatttgta ttgtcaactt tatatagatt taaaaaaata atctcatgtc    1560
tttttttaca aaagtaagtt aattattaca aactagtaac aaaaattatt tcttcaaaaa    1620
tatatttagt agcgaataca cttcatcttt gaattgactt ttactttctt ccactgctcc    1680 aaattttgc gaaaaggatg ctttcaaata ccaactttca agaaacagca atattaaatt    1740
ctgaaagtct tcttttgtca tctttatctt tgattcatca tagaattttg ctatctcttt    1800
acttaatgat tgatttaaat cttgtatttg tccgtaaata tttccagaaa attcctcagg    1860
cgtattagat aattgaacgt acattctaat ataccttct tcgatgtcga aaataaactc    1920
aaataagaat tgatataaag catcaattga atagttcgat ttattttgat tcatcataat    1980
aatattatta aggtaatcaa acaacatttt aacactttgt tcgtaaatac tttttttcga    2040
gtcaaaatgg taatataaac tcgctttctt tatatttaca cttttagcta tatcatcaag    2100
tgttgtaccg tcatacccct tctctgaaaa taaggttatt gcgttatcaa taatcttatc    2160
cttcaatttt tataaccccc tactgaaaat taatcacact atgttacagg aaaattaagt    2220
tgcaattaca aatatttccg tttaattata acaacaatct attgcaaatt aaaatactat    2280
caattaccat atggcttaca acctaactaa cgaaaggtag gtaaagaaat tgcaatttt    2340 taacttttg ctttttatc ctgtatttat gtctatttac tggattgtcg gttcaattta    2400
tttctatttc accagagaaa ttagatattc attgaacaag aagcctgaca taaatgtgga    2460
tgaattagaa ggcattacat tttacttgc ctgttataac gaaagtgaaa cgattgaaga    2520
tacgttgtct aatgttcttg cactcaaata cgagaagaaa gaaattatta tcattaatga    2580
tggaagttca gataatacag cagaactcat ctataaaatc aaagaaaata atgactttat    2640
tttcgtcgat ttacaagaaa acagaggtaa agccaacgca ctcaatcaag gcattaaaca    2700
ggcttcatat gattatgtaa tgtgcttgga tgcagatact atcgttgatc aagatgcacc    2760
atattatatg attgagaatt tcaaacatga tccaaaactt ggtgcggtta caggtaatcc    2820
tagaattcga aataagagtt ctattttagg taaaattcaa acgatagaat atgcaagttt    2880
aattggctgt attaagcgaa gtcagacact tgctggcgca gtcaatacta tttcgggtgt    2940
cttcactcta tttaaaaaaa gtgcagttgt cgacgttggc tactgggata ctgatatgat    3000
taccgaagat attgcagttt cttggaaatt gcatttacgt ggatatcgta ttaagtatga    3060
accgcttgcc atgtgttgga tgttggttcc agaaacattg ggaggtcttt ggaagcaacg    3120
cgtgagatgg gctcaagggg gacacgaagt attactacga gactttttta gcacaatgaa    3180
aacgaaaagg tttcctttat atattttgat gtttgagcaa atcatctcga ttttatgggt    3240
atatatagtg cttctatatt taggctattt gttcataaca gcaaacttct tagactatac    3300
atttatgaca tatagttttt caatatttct actatcatca tttactatga cttttataaa    3360
cgttattcaa tttacagtcg cactcttat tgatagtcgc tacgagaaaa agaatatggc    3420
tggactcata tttgtaagtt ggtatccgac agtatactgg attattaacg cagcagtagt    3480
tcttgtcgca tttccaaaag cattaaaacg taagagaggt ggttacgcaa catggtcaag    3540
cccagacaga gggaatacc aacgctaaaa tcatcgctaa atattgtaag agaaacagca    3600
cttatcgcta tatcttgtgt cttttggata tattgtttag ttgttctact cgtttatatt    3660
```

```
ggtactatat ttgaaattca tgacgaaagt atcaatacaa tacgtgttgc tttaaacatt   3720
gaaaatactg aaattttaga tatatttgaa actatgggca ttttcgcgat tatcatttt    3780 gtattttta caattagcat attgattcaa aaatggcaga gagggagaga atcgtgaagt    3840
atagaaaatt tataattta gtgttgagta tcttgatcat attgcctgta agcacactgg    3900
atggtcatca tattgcaaat gcagatgacg attcacctaa aaaactgaaa tataaagaaa   3960
atagtgctct ggcattaaat tatcaccgtg taagaaaagc gaattttctg aataatttta   4020
tttacttctt ttctagtagt aaagaaatta aaattatag tgttagtcaa tcacaatttg    4080
aatctcaaat aaaatggcta aaatcacatg atgctaaatt tttaaccttg aaagaatttt   4140
tatattacaa gaaaaaaggt aagtttccaa acgaagtga gtgggttaac tttgatgata    4200
tggatgaaac tatttatgaa aatgcttatc caatcttaaa aaaatataaa ataccggcga   4260
ctgggtttat tatcacaggt catgttgggg gggaaaactt tcacaacctc gatatgatta   4320
gtaaaaaaga actaaagaa atgtataaaa ctgggttatg ggaatttgaa acacataccc   4380
acgatttgca taacttatct aaaaataata agtcaaaatt aatgaaagct tctgaagcta   4440
caatcataaa agatttaaac aaaagtgaaa aatatctaac taaaaacttt aaaaagtcgc   4500
agaaaactat agcctatcct tatggcttga tgaatgacga taaattaccg gtaatcaaaa   4560
aagctgggtt aaaatacggt ttttcattag aggaaaaagc agtcactccg aactccaatg   4620
attattacat ccctagaata ttaattagtg atgatgcttt tgagcattta attaagagat   4680
gggacggatt ccatgaaaaa gattagactt gaactcgtat atttacgtgc tattatatgt   4740
gcaattatta ttatcacaca tttacttaca caaattactt taaaacatga aaatatggag   4800
ggtgggtcct tagtgttaca attttacatt cgtaatattg tgattttttgg tacaccttgc   4860 tttattatct tgtcacagtt actgacaacc ttgaattacc aaaaagtcac ctatagatac    4920
ttaactacac gcgtaaaata tacttatt ccttacatat taatgggatt gttttacagt     4980
tatagtgaat cattattaac agattcaagt ttcaataaac aattcattga aaatgtccta   5040
ttaggtcaat ggtatggcta ttttatcgtt gttatcatgc aattctttat tttgagttat    5100 atcatttta aaattaacta taacctattc aacagtaaaa tattattatt gttatctttt    5160
attttacagc aatcatttt tatattcttt acgaacaaca cagcgtttca cgataccgtg    5220
ctacactatt atccccttaag tgaaaatact ataatattcg gatggatttt ttatttcttc   5280
ttaggtgcat atatgggtta taactacgaa cgtgtattaa atttcttaga acgttattta   5340
gttattatga ttgtattagc tgtagctact tatttgtgt ttattgcgtt agcaaatgga    5400
gactattgga acgttaccag cttttcatat tcattaacac catataatag tattatgttt    5460
attgttatct tgggtatttg cacgcatttt aaaacaatgt tatttaatac gattcaaatg   5520
attagtgctt tctcattctt tatttattta ttacatccaa tcattctaga ctcattgttt    5580
gcatatacaa atatatttga ggataataca atggtctttc tagcgatatc actactattc   5640
attttaggat tatgtatagg tgtcggcatg atattgcgtg aattctatat ctttaggttt   5700
attattggaa acaaccata taaattgaac attaatgctt attaattatt aagctatgtt    5760
aaaaacacgc ggtgggcgaa atcagtttga attgactgac ttcgttttac cgcgtgttta   5820
atattgttat acatatattc taattgcaca tttaaacttc gtaaatgcca atgggagtgg   5880
gacagaaatg atattttcgc aaaatttatt tcgtcgtccc accccaactt gcacattatt   5940
gtaacctgac tttccgccag cttctatgtt ggggccccgc caacttgcac attattgtaa   6000
```

```
gctgactttc cgccagcttc tttgttgggg ccccgccaac ttgcattgtt tgtagaattt    6060
cttttcgaaa ttctttatgt tggggcctcg cccaatgttt tacttgaata attcttttag    6120
aattctaaat aatgatccga ttaattgaaa gaagtctgca gtcattatta attcctccct    6180
ttactttata aattatgctt gcttagtatc agtcagcttt tcagttttca ctaaatcgtc    6240
tgctaaatga tgccaaaaat cttgtaattc ttctcttgtg cgcactgtat cagaactgtc    6300
ttgtcctaca aagtcaacat gatcccaatc atgttttgta ggcgtcactt gccaaatgcc    6360
tttttgaatt ttatctgtcg cttttgtata agcttgatta aatggatgtt gagaagaaat    6420
aacggatact aaaccatcgt tttctcgcca ttcttttca gtagctttac cgattaagtt     6480
accagtaatc acaaatggga aaacatatt taagtctgct                           6520
```

<210> SEQ ID NO 4
<211> LENGTH: 5
<212> TYPE: DNA
<213> ORGANISM: Staphylococcus aureus

<400> SEQUENCE: 4

```
tattt                                                                    5
```

<210> SEQ ID NO 5
<211> LENGTH: 33
<212> TYPE: DNA
<213> ORGANISM: Artificial sequence
<220> FEATURE:
<223> OTHER INFORMATION: Oligonucleotide

<400> SEQUENCE: 5

```
tttcttcaaa aatatattta gtagcgaata cac                                    33
```

<210> SEQ ID NO 6
<211> LENGTH: 29
<212> TYPE: DNA
<213> ORGANISM: Artificial sequence
<220> FEATURE:
<223> OTHER INFORMATION: Oligonucleotide

<400> SEQUENCE: 6

```
aaggataaga ttattgataa cgcaataac                                         29
```

<210> SEQ ID NO 7
<211> LENGTH: 28
<212> TYPE: DNA
<213> ORGANISM: Artificial sequence
<220> FEATURE:
<223> OTHER INFORMATION: Oligonucleotide

<400> SEQUENCE: 7

```
ccgtttaatt ataacaacaa tctattgc                                          28
```

<210> SEQ ID NO 8
<211> LENGTH: 30
<212> TYPE: DNA
<213> ORGANISM: Artificial sequence
<220> FEATURE:
<223> OTHER INFORMATION: Oligonucleotide

<400> SEQUENCE: 8

```
tttgtaattg caacttaatt ttcctgtaac                                        30
```

<210> SEQ ID NO 9
<211> LENGTH: 34

<212> TYPE: DNA
<213> ORGANISM: Artificial sequence
<220> FEATURE:
<223> OTHER INFORMATION: Oligonucleotide

<400> SEQUENCE: 9
ataaaccgtt taattataac aacaatctaa ttgc                                      34

<210> SEQ ID NO 10
<211> LENGTH: 53
<212> TYPE: DNA
<213> ORGANISM: Artificial sequence
<220> FEATURE:
<223> OTHER INFORMATION: Oligonucleotide

<400> SEQUENCE: 10
ctatgttaca ggaaaattaa gttgcaatta caaatatttc cgtttaatta taa                 53

<210> SEQ ID NO 11
<211> LENGTH: 53
<212> TYPE: DNA
<213> ORGANISM: Artificial sequence
<220> FEATURE:
<223> OTHER INFORMATION: Oligonucleotide

<400> SEQUENCE: 11
ctatgttaca ggaaaattaa gttgcaatta caaaataaac cgtttaatta taa                 53

<210> SEQ ID NO 12
<211> LENGTH: 48
<212> TYPE: DNA
<213> ORGANISM: Artificial sequence
<220> FEATURE:
<223> OTHER INFORMATION: Oligonucleotide

<400> SEQUENCE: 12
ctatgttaca ggaaaattaa gttgcaatta caaaccgttt aattataa                       48

<210> SEQ ID NO 13
<211> LENGTH: 27
<212> TYPE: DNA
<213> ORGANISM: Artificial sequence
<220> FEATURE:
<223> OTHER INFORMATION: Oligonucleotide

<400> SEQUENCE: 13
attgcgttat caataatctt atccttc                                              27

<210> SEQ ID NO 14
<211> LENGTH: 24
<212> TYPE: DNA
<213> ORGANISM: Artificial sequence
<220> FEATURE:
<223> OTHER INFORMATION: Oligonucleotide

<400> SEQUENCE: 14
ttgcaatttc tttacctacc tttc                                                 24

<210> SEQ ID NO 15
<211> LENGTH: 198
<212> TYPE: DNA
<213> ORGANISM: Artificial sequence
<220> FEATURE:
<223> OTHER INFORMATION: Oligonucleotide

<400> SEQUENCE: 15

```
attgcgttat caataatctt atccttcaat ttttataacc ccctactgaa aattaatcac      60
actatgttac aggaaaatta agttgcaatt acaaatattt ccgtttaatt ataacaacaa     120
tctattgcaa attaaaatac tatcaattac catatggctt acaacctaac taacgaaagg     180
taggtaaaga aattgcaa                                                   198

<210> SEQ ID NO 16
<211> LENGTH: 193
<212> TYPE: DNA
<213> ORGANISM: Artificial sequence
<220> FEATURE:
<223> OTHER INFORMATION: Oligonucleotide

<400> SEQUENCE: 16
attgcgttat caataatctt atccttcaat ttttataacc ccctactgaa aattaatcac      60
actatgttac aggaaaatta agttgcaatt acaaaccgtt taattataac aacaatctat     120
tgcaaattaa aatactatca attaccatat ggcttacaac ctaactaacg aaaggtaggt     180
aaagaaattg caa                                                        193

<210> SEQ ID NO 17
<211> LENGTH: 53
<212> TYPE: DNA
<213> ORGANISM: Artificial sequence
<220> FEATURE:
<223> OTHER INFORMATION: Oligonucleotide

<400> SEQUENCE: 17
ctatgttaca ggaaaattaa gttgcaatta caaatatttc cgtttaatta taa             53

<210> SEQ ID NO 18
<211> LENGTH: 48
<212> TYPE: DNA
<213> ORGANISM: Artificial sequence
<220> FEATURE:
<223> OTHER INFORMATION: Oligonucleotide

<400> SEQUENCE: 18
ctatgttaca ggaaaattaa gttgcaatta caaaccgttt aattataa                   48

<210> SEQ ID NO 19
<211> LENGTH: 561
<212> TYPE: DNA
<213> ORGANISM: Staphylococcus aureus

<400> SEQUENCE: 19
ttgaaggata agattattga taacgcaata accttatttt cagagaaggg gtatgacggt      60
acaacacttg atgatatagc taaaagtgta aatataaaga aagcgagttt atattaccat     120
tttgactcga aaaaagtat ttacgaacaa agtgttaaat gttgttttga ttaccttaat     180
aatattatta tgatgaatca aaataaatcg aactattcaa ttgatgcttt atatcaattc     240
ttatttgagt ttattttcga catcgaagaa aggtatatta aatgtacgt tcaattatct     300 aatacgcctg aggaattttc tggaaatatt tacggacaaa tacaagattt aaatcaatca     360
ttaagtaaag atagcaaaa attctatgat gaatcaaaga taaagatgac aaaagaagac     420
tttcagaatt taatattgct gtttcttgaa agttggtatt tgaaagcatc cttttcgcaa     480
aaatttggag cagtggaaga aagtaaaagt caattcaaag atgaagtgta ttcgctacta     540
aatatatttt tgaagaaata a                                               561
```

-continued

```
<210> SEQ ID NO 20
<211> LENGTH: 186
<212> TYPE: PRT
<213> ORGANISM: Staphylococcus aureus

<400> SEQUENCE: 20

Met Lys Asp Lys Ile Ile Asp Asn Ala Ile Thr Leu Phe Ser Glu Lys
1               5                   10                  15

Gly Tyr Asp Gly Thr Thr Leu Asp Ile Ala Lys Ser Val Asn Ile
            20                  25                  30

Lys Lys Ala Ser Leu Tyr Tyr His Phe Asp Ser Lys Lys Ser Ile Tyr
            35                  40                  45

Glu Gln Ser Val Lys Cys Cys Phe Asp Tyr Leu Asn Asn Ile Ile Met
        50                  55                  60

Met Asn Gln Asn Lys Ser Asn Tyr Ser Ile Asp Ala Leu Tyr Gln Phe
65                  70                  75                  80

Leu Phe Glu Phe Ile Phe Asp Ile Glu Glu Arg Tyr Ile Arg Met Tyr
                85                  90                  95

Val Gln Leu Ser Asn Thr Pro Glu Glu Phe Ser Gly Asn Ile Tyr Gly
            100                 105                 110

Gln Ile Gln Asp Leu Asn Gln Ser Leu Ser Lys Glu Ile Ala Lys Phe
        115                 120                 125

Tyr Asp Glu Ser Lys Ile Lys Met Thr Lys Glu Asp Phe Gln Asn Leu
    130                 135                 140

Ile Leu Leu Phe Leu Glu Ser Trp Tyr Leu Lys Ala Ser Phe Ser Gln
145                 150                 155                 160

Lys Phe Gly Ala Val Glu Glu Ser Lys Ser Gln Phe Lys Asp Glu Val
                165                 170                 175

Tyr Ser Leu Leu Asn Ile Phe Leu Lys Lys
            180                 185
```